US 6,313,094 B1

(12) United States Patent
Mimoto et al.

(10) Patent No.: US 6,313,094 B1
(45) Date of Patent: *Nov. 6, 2001

(54) β-AMINO-α-HYDROXYCARBOXYLIC ACID DERIVATIVES AND HIV PROTEASE INHIBITORS

(75) Inventors: Tsutomu Mimoto; Naoko Hattori, both of Saitama; Makoto Shintani, Tokyo; Yuuichi Nagano, Saitama; Yoshiaki Kiso, Osaka, all of (JP)

(73) Assignee: Japan Energy Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 08/246,843

(22) Filed: May 20, 1994

Related U.S. Application Data

(63) Continuation of application No. 08/044,043, filed on Apr. 8, 1993, now abandoned, which is a continuation-in-part of application No. 07/804,590, filed on Dec. 10, 1991, now abandoned.

(30) Foreign Application Priority Data

| Dec. 11, 1990 | (JP) | 2-409673 |
| Jan. 25, 1991 | (JP) | 3-025755 |
| Mar. 28, 1991 | (JP) | 3-089976 |
| Jun. 14, 1991 | (JP) | 3-167174 |
| Oct. 23, 1991 | (JP) | 3-304043 |

(51) Int. Cl.$^7$ .................................................. C07K 5/08
(52) U.S. Cl. .................. 514/18; 514/16; 514/17; 514/19; 530/329; 530/330; 530/331; 530/332
(58) Field of Search .................. 514/16–19; 530/329, 530/330, 331, 332

(56) References Cited

U.S. PATENT DOCUMENTS

| 4,240,975 | 12/1980 | Umezawa et al. | 558/273 |
| 4,656,269 | 4/1987 | Iizuka et al. | 544/139 |
| 4,711,958 | 12/1987 | Iizuka et al. | 544/139 |
| 4,841,067 | 6/1989 | Iizuka et al. | 548/338.1 |
| 4,853,463 | 8/1989 | Iizuka et al. | 530/323 |
| 4,857,650 | 8/1989 | Iizuka et al. | 548/314.7 |
| 4,870,183 | 9/1989 | Iizuka et al. | 546/210 |
| 5,342,922 | 8/1994 | Marshall et al. | 530/329 |
| 5,932,550 | 8/1999 | Kato et al. | 514/19 |
| 5,962,640 | 10/1999 | Kato et al. | 530/337 |

FOREIGN PATENT DOCUMENTS

| 2015070 | 10/1990 | (CA) . |
| 337714 | 10/1989 | (EP) . |
| 357332 | 3/1990 | (EP) . |
| 372537 | 6/1990 | (EP) . |
| 373497 | 6/1990 | (EP) . |
| 373549 | 6/1990 | (EP) . |
| 0 498 680A1 | 2/1992 | (EP) . |
| 05178824A | 6/1992 | (EP) . |
| 0 539 192 A1 | 4/1993 | (EP) . |
| 0 587 311 A1 | 3/1994 | (EP) . |
| 0 751 145 A2 | 1/1997 | (EP) . |
| 61-186366 | 8/1986 | (JP) . |
| 61-200970 | 9/1986 | (JP) . |
| 62-004286 | 1/1987 | (JP) . |
| 62-033156 | 2/1987 | (JP) . |
| 62-120370 | 6/1987 | (JP) . |
| 63-017867 | 1/1988 | (JP) . |
| 63-275552 | 11/1988 | (JP) . |
| 2101098 | 4/1990 | (JP) . |
| 05294993A | 10/1991 | (JP) . |
| WO93/13066 | 7/1993 | (WO) . |

OTHER PUBLICATIONS

Swain et al. (1990) "X–ray Crystallographic . . . ," *PNAS, USA* 87:8805–8809.
Nishizawa et al. (1977) "Synthesis and Structure–Activity," *J. Med. Chem.* 20:510–515.
Iizuka et al. (1990) "Orally Potent Human Renin," *J. Med. Chem.* vol. 33, 10:2707–2714.
Iizuka et al. (1988) "New Human Renin Inhibitory . . . ," *Chem. Pharm. Bull.* 36:2278–2281.
Iizuka et al. (1988) "New Human Renin Inhibitory . . . ," *J. of Med. Chem.* vol. 31, 4:701–704.
Iizuka et al. (1989) "Design and Synthesis . . . ," *J. Chem. Soc., Chem. Chem. Commun*, pp. 1678–1880.
Harada et al. (1989) "A Simple Diastereoselective . . . ," *Chem. Pharm. Bull.* vol. 37, 9:2570–2572.
Harada et al. (1990) "A Practical Synthesis . . . ," *J. Chem. Soc. Perkins Trans.* pp. 2497–2500.
Iizuka et al. (1990) "Synthesis and Structure . . . ," *Chem. Pharm. Bull.* vol. 38, 9:2487–2493.
Ashorn et al. (1990) "An Inhibitor of the Protease . . . ," *PNAS, USA* 87:7472–7476.
Harada et al. (1990) "Synthesis of Human Renin . . . ," *Chem. Pharm. Bull.* vol. 38, 11:3042–3047.
Mimoto et al. (1991) "Design and Synthesis of HIV . . . ," *Pharm. Soc. of Japan, 111th Ann. Meeting* 30V:10–047.
Peter et al. (1991) "Detection of Antibodies to HIV–1 . . . ," *12th Amer. Peptide Symposium* p. 433.
Mimoto et al. (1991) *Chem. Pharm. Bull.* vol. 39, 9:2465–2467.

(List continued on next page.)

*Primary Examiner*—Christopher S. F. Low
*Assistant Examiner*—David Lukton
(74) *Attorney, Agent, or Firm*—Testa, Hurwitz, & Thibeault, LLP

(57) ABSTRACT

β-Amino-α-hydroxycarboxylic acid derivatives represented by the following formula and salts thereof which are useful as human immunodeficiency virus (HIV) protease inhibitors:

$$A-B^1-B^2-B^3-NH-\underset{\underset{R^1}{|}}{CH}-\underset{\underset{OH}{|}}{CH}-\underset{\underset{O}{\|}}{C}-N\underset{CH-C-B^5-B^6-XR^2R^3}{\overset{R^6}{\diagdown}}\overset{O}{\underset{\|}{}}$$

The compounds are effective for treating a patient suffering from AIDS and AIDS related diseases.

42 Claims, 6 Drawing Sheets

OTHER PUBLICATIONS

Mimoto et al. (1991) "Design and Synthesis . . . ," *29th Symposium on Peptide Chemistry* 2P-17.

Raju et al. (1991) "Substrate Analog Inhibitors . . . ," *Biochem. & Biophys. Res. Commun.* vol. 180, 1:181–186.

Raju et al. (1991) "Investigating the Stereochemistry . . . ," *Biochem. & Biophys. Res. Commun.* vol. 180, 1:187–190.

Kiso et al. (1991) "Development of Protease Inhibitors . . . ," *Bio. Ind.* vol. 8, 10:704–710.

Mimoto et al. (1991) "KN1–102, A Novel . . . ," *Chem. Pharm. Bull.* vol. 39, 11:3–88–3090.

Mimoto et al., *1st Ann. Meeting of Division of Medicinal Chemistry* (1991) p. 29.

Overton et al. (1990) "Effect of Two Novel Inhibitors . . . ," *Virology* 179:508–511.

Baboonian et al. (1991) "HIV–1 Proteinase . . . ," *Biochem. & Biophys. Res. Commun.* vol. 179, 1:17–24.

Meek et al. (1990) "Inhibition of HIV–1 . . . ," *Nature* 343:90–92.

Roberts et al. (1990) "Rational Design . . . ," *Science* 248:358–361.

Rich et al. (1980) "Synthesis of (2S, 3R) . . . " *J. Org. Chem.* 45:2288–2290.

Kiso et al. (1992) *Farumashia* 28(2):151–155.

Mimoto et al. (1992) "Design and Synthesis . . . ," *Peptide Chem. Protein* pp. 395–400.

Kiso et al. (1992) *Pharmaceutical Society of Japan 112th Ann. Meeting*, 30ZF 3–1, 3–2, 3–3, 3–4, 3–5.

Kiso et al. (1992) *VIII Intl. Conf. on AIDS/III STD World Congr.*, Poster Abstracts 19–24.

Mimoto et al. (1992) "Kynostatin (KNI)–227 . . . ," *Chem. Pharm. Bull.*, 40(8) 2251–2253.

Kiso et al. (1992) "Structure–Activity Relationships . . . ," *Eur. Peptide Symposium*, p. 246, P337.

Mimoto et al. (1992) *2nd Japan Symposium on Peptide Chemistry*, p. 105, p. 125.

Mimoto et al. (1992) "Design and Synthesis of the . . . ," *2nd Ann. Meeting of Div. of Med. Chemistry*, p. 1.

Mimoto et al. (1993) *Pharm. Soc. of Japan 113th Ann. Meeting*, 31CC 11–2, 30FC 15–1.

Abstract, "XI International Conference on AIDS, Vancouver, Jul. 7–12, 1996," vol. 1, p. 77 (Ref. No. Mo.B. 1132); published Jul. 6, 1996; presented Jul. 8, 1996.

Ashorn et al. (1990), "An Inhibitor of the Protease Blocks Maturation of Human and Simian Immunodeficiency Viruses and Spread of Infection," 87 *Proc. Natl. Acad. Sci. USA* 7472–7476.

Debouck et al. (1990), "Human Innumodeficiency Virus Protease: A Target For AIDS Therapy," 21 *Drug Dev. Res.* 1–17.

Meek et al. (1990), "Inhibition of HIV–1 Protease In Infected T–lymphocytes by Synthetic Peptide Analogues," 343 *Nature* 90–92.

McCune et al. (1990), "Suppression of HIV Infection in AZT–Treated SCID–hu Mice," 247 *Science* 564–566.

Roberts et al. (1990), "Rational Design of Peptide–Based HIV Proteinase Inhibitors," 248 *Science* 358–361.

Kaneshima et al. (1991), "Human Immunodeficiency Virus Infection of Human Lymph Nodes in the SCID–hu Mouse," 88 *Proc. Natl. Acad. Sci. USA* 4523–4527.

McCune et al. (1991), "Preclinical Evaluation of Human Hematolymphoid Function in the SCID–hu Mouse," 124 *Immunolog. Rev.* 45–62.

Mimoto et al. (1991), "Rational Design and Synthesis of a Novel Class of Active Site–Targeted HIV Protease Inhibitors Containing a Hydroxymethylcarbonyl Isostere. Use of Phenylnorstatine or Allophenylnorstatine As A Transition-State Mimic," 39 *Chem. Pharm. Bull.* 9:2465–2467.

Romero et al. (1991), "Nonnucleoside Reverse Transcriptase Inhibitors That Potently and Specifically Block Human Immunodeficiency Virus Type 1 Replication," 88 *Proc. Natl. Acad. Sci. USA* 8806–8810.

Shih et al. (1991), "Postexposure Prophylaxis With Zidovudine Suppresses Human Immunodeficiency Virust Type 1 Infection in SCID–hum Mice in a Time–Dependent Manner," 163 *J. Infect. Dis.* 625–627.

Kageyama et al. (1992), "In Vitro Inhibition of Human Immunodeficiency Virus (HIV) Type 1 Replication by $C_2$ Symmetry–Based HIV Protease Inhibitors As Single Agents or in Combination," 36 *Antimicrob. Agents Chem.* 5:926–931.

Meek (1992), "Inhibitors of HIV–1 Protease," 6 *J. Enzyme Inhib.* 65–98.

Mimoto et al. (1992), "Kynostatin (KNI)–227 and –272, Highly Potent Anti–HIV Agents: Conformationally Constrained Tripeptide Inhibitors of HIV Protease Containing Allophenylnorstatine," 40 *Chem. Pharm. Bull.* *:2251–2253.

Kageyama et al. (1993), "In Vitro Anti–Human Immunodeficiency Virus (HIV) Activities of Transition State Mimetic HIV Protease Inhibitors Containing Allophenylnorstatine," 37 *Antimicrob. Agents Chem.* 4:810–817.

Ussery et al. (1995), "In Vivo Antibacterial Activity of the Protease Inhibitor KNI–272 in the HIV–Infected HuPBMC-SCID Mouse Model," 35th Interscience Conference on Antimicrobial Agents and Chemotherapy, Annual Meeting of The American Society For Microbiology, Abstract No. 125, p. 227.

"Japan Energy To Test AIDS Drug In Britain," Press Release Dec. 4, 1995; Jiji Press Ticker Service, Tokyo, Japan.

"Japan Energy Starts Clinical Testing of AIDS Drug in UK," Press Release Dec. 5, 1995; Jiji Press Ticker Service, Tokyo, Japan.

"Anti–AIDS Drug Tests Go To Britain," Press Release Dec. 5, 1995; *Japan Times*, Tokyo, Japan.

Debouck et al. (1990), "Human Immunodeficiency Virus Protease: A Target for AIDS Therapy," *Drug Development Research*, No. 21, pp. 1–17.

McCune et al. (1990), Suppression of HIV Infection in AZT–Treated SCID–hu Mice, *Science*, vol. 247, pp. 564–566.

Kaneshima et al. (1991), "Human Immunodeficiency Virus Infection of Human Lymph Nodes in the SCID–hu Mouse," *Proc. Natl. Acad. Sci.*, vol. 88, pp. 4523–4527.

McCune et al. (1991), "Preclinical Evaluation of Human Hematolymphoid Function in the SCID–hu Mouse," *Immunological Reviews*, No. 124, pp. 45–62.

Romero et al. (1991), "Nonnucleoside Reverse Transcriptase Inhibitors that Potently and Specifically Block Human Immunodeficiency Virus Type 1 Replication," *Proc. Natl. Acad. Sci.*, vol. 88, pp. 8806–8810.

Shih et al. (1991), "Postexposure Prophylaxis with Zidovudine Suppresses Human Immunodeficiency Virus Type 1 Infection in SCID–hu Mice in a Time–Dependent Manner," *Journal of Infectious Diseases*, No. 163, pp. 625–627.

Kageyama et al. (1992), "In Vitro Inhibition of Human Immunodeficiency Virus (HIV) Type 1 Replication by $C_2$ Symmetry–Based HIV Protease Inhibitors as Single Agents or in Combinations," *Antimicrob. Agents and Chemother.*, vol. 36, No. 5, pp. 926–933.

Meek (1992), "Inhibitors of HIV–1 Protease," *J. Enzyme Inhibition*, vol. 6, pp. 65–98.

Communications to the Editor (1992), "Intriguing Structure-Activity Relations Underlie the Potent Inhibition of HIV Protease by Norstatine–Based Peptides," *Journal of Medicinal Chemistry*, vol. 35, No. 7, pp. 1318–1320.

Robins et al. (1993), "HIV Protease Inhibitors: Their Anti-HIV Activity and Potential Role in Treatment," *Journal of Acquired Immune Deficiency Syndromes*, vol. 6, No. 2, pp. 162–170.

(Example 82)

(Example 86)

(Example 100)

(Example 106)

(Example 130)

(Example 193)

β-AMINO-α-HYDROXYCARBOXYLIC ACID DERIVATIVES AND HIV PROTEASE INHIBITORS

REFERENCE TO RELATED APPLICATIONS

This application is a continuation of U.S. Ser. No. 08/044,043 filed Apr. 8, 1993, now abandoned which is a continuation-in-part of U.S. Ser. No. 07/804,590 filed Dec. 10, 1991, now abandoned.

BACKGROUND OF THE INVENTION

1. Field of the Invention

The present invention relates to β-Amino-α-hydroxycarboxylic acid derivatives and salts thereof which are useful as human immunodeficiency virus (HIV) protease inhibitors and/or as intermediates for synthesizing the inhibitors.

2. Description of the Related Art

Heretofore, various efforts for the therapy of acquired immunodeficiency syndrome (AIDS) and the prevention of infection of the human immunodeficiency virus (HIV) by inhibiting the HIV protease have been performed. Some peptide derivatives have been proposed as the inhibitor, for example, Japanese Unexamined Patent Publication Nos. 117615, 209854, 202898, 202899, 204475 (1990) and Review: *J. Med. Chem.*, 34, 2305 (1991). Some HIV protease inhibitors involve the use of hydroxy amino acid isosteres, and in addition, a formation of hydrogen bond between the hydroxy group and Asp25 in the active site of HIV protease was proposed.

Also, a renin inhibitor having a β-amino-α-hydroxycarboxylic residue shown by the following general formula (6) as an amino acid isostere in a peptide chain was proposed, for example, in Japanese Unexamined Patent Publication No. 101098 (1990) and the preparation of said carboxylic acid was reported in relation to an anti-cancer agent, for example, in *J. Med. Chem.*, 20, 510, (1977), ibid., 33, 2707 (1990).

Formula (6) has the following structure:

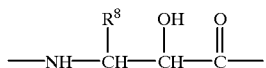

(6)

In the general formula (6), $R^8$ represents a straight or branched lower alkyl group, a cycloalkyl-lower alkyl group, a lower alkoxycarbonyl-lower alkyl group, an amino-lower alkyl group, or an aryl-lower alkyl group.

However, no β-amino-α-hydroxy-carbocyclic acid mentioned above has been used as amino acid isostere in an HIV protease inhibitor.

Further, compounds having the following basic structure represented by general formula (3) and (3') are not known.

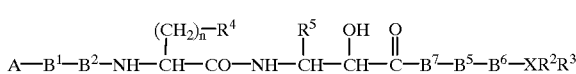

(3)

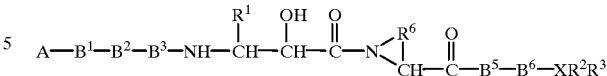

(3')

wherein n represents 1 or 2, A represents a hydrogen atom or a peptide N-terminal protective group, $B^1$, $B^2$, $B^3$, $B^5$, and $B^6$ represents independently a single bond or an amino acid residue, optionally the amino group of said amino acid can be substituted with a hydrocarbon residue having 12 or less carbon atoms, $B^7$ represents a single bond or an amino acid residue represented by following formula (4) with a proviso that $XR^2R^3$ represents the following general formula (4') when $B^7$ is a single bond, X represents a nitrogen atom or an oxygen atom, $R^1$ represents a lower alkyl group, an alicyclic hydrocarbon group, an aromatic hydrocarbon group or a heterocyclic group optionally substituted with an amino group, a mercapto group, a hydroxy group, a carboxy group, a carbamoyl group, an alicyclic hydrocarbon group, an aromatic hydrocarbon group or a heterocyclic group, $R^2$ and $R^3$ each represents a hydrogen atom or an optionally substituted hydrocarbon group having 12 or less carbon atoms which form cycles by forming bonds between said carbon atoms which may optionally be replaced with an oxygen, nitrogen or sulfur atom with the proviso that no $R^3$ is present when X represents oxygen atom, $R^4$ represents a carbamoyl group, a carboxy group, a cyano group, an alkoxycarbonyl group, a hydroxy group, a lower alkoxy group, a lower alkylthio group, a lower alkanesulfonyl group, a sulfonyl group, a lower alkanesulfinyl group or a sulfamoyl group, $R^5$ represents an optionally substituted arylmethyl group, and $R^6$ has the same meaning as that in the following general formula (4):

(4)

(4')

wherein $R^6$ and $R^7$ represent a bivalent hydrocarbon group forming a 5–7 membered ring optionally substituted or fused with the other 5–7 membered ring, and a part of carbon atoms in said rings optionally replaced with hetero atoms.

SUMMARY OF THE INVENTION

It is an object of the present invention to provide novel HIV protease inhibitors.

Another object of the invention is to provide novel compounds with excellent inhibitory action having a β-Amino-α-hydroxycarboxylic acid residue as an amino acid isostere.

The object of the present invention has been attained by the following HIV protease inhibitors:

Human immunodeficiency virus (HIV) protease inhibitors comprising a compound represented by the following general formula (1) or a pharmaceutically acceptable salt thereof:

(1)

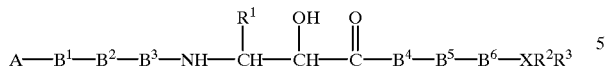

wherein A represents a hydrogen atom or a peptide N-terminal protective group, $B^1$, $B^2$, $B^3$, $B^4$, $B^5$, and $B^6$ represent independently a single bond or amino acid residue in which the amino group is optionally substituted with a hydrocarbon group having 12 or less carbon atoms, with a proviso that the presence of at least one of said $B^1$ through $B^6$ is necessary, $R^1$ represents a lower alkyl group, an alicyclic hydrocarbon group, an aromatic hydrocarbon group or a heterocyclic group, each optionally substituted with an amino group, a mercapto group, a hydroxy group, a carboxy group, a carbamoyl group, an alicyclic hydrocarbon group, an aromatic hydrocarbon group or a heterocyclic group, X represents a nitrogen atom or an oxygen atom, and $R^2$ and $R^3$ each represents a hydrogen atom or a hydrocarbon group having 12 or less carbon atoms which may form cycles of which carbon atoms may optionally be replaced with an oxygen, nitrogen or sulfur atom, with the proviso that no $R^3$ is present when X represents an oxygen atom.

Another object of the present invention has been attained by novel compounds represented by the following general formula (3) or (3'), and the HIV protease inhibitors containing said compound or pharmaceutically acceptable salt compounds thereof:

(3)

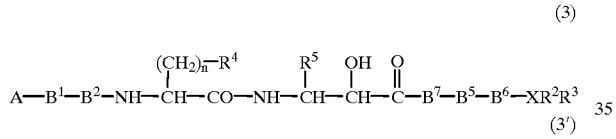

(3')

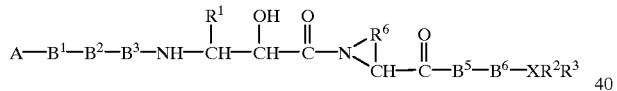

wherein n represents 1 or 2, A represents a hydrogen atom or a peptide N-terminal protective group, $B^1$, $B^2$, $B^3$, $B^5$, and $B^6$ represents independently a single bond or an amino acid residue, optionally the amino group of said amino acid can be substituted with a hydrocarbon residue having 12 or less carbon atoms, $B^7$ represents a single bond or an amino acid residue represented by the following formula (4), with a proviso that $XR^2R^3$ represents the following general formula (4') when $B^7$ is a single bond, X represents a nitrogen atom or an oxygen atom, $R^1$ represents a lower alkyl group, an alicyclic hydrocarbon group, an aromatic hydrocarbon group or a heterocyclic group optionally substituted with an amino group, a mercapto group, a hydroxy group, a carboxy group, a carbamoyl group, an alicyclic hydrocarbon group, an aromatic hydrocarbon group or a heterocyclic group, $R^2$ and $R^3$ each represents a hydrogen atom or an optionally substituted hydrocarbon group having 12 or less carbon atoms which form cycles by forming bonds between said carbon atoms which may optionally be replaced with an oxygen, nitrogen or sulfur atom, with the proviso that no $R^3$ is present when X represents an oxygen atom, $R^4$ represents a carbamoyl group, a carboxy group, a cyano group, an alkoxycarbonyl group, a hydroxy group, a lower alkoxy group, a lower alkylthio group, a lower alkanesulfonyl group, a sulfonyl group, a lower alkanesulfinyl group or a sulfamoyl group, $R^5$ represents an optionally substituted arylmethyl group, and $R^6$ has the same meaning as that in the following general formula (4):

(4)

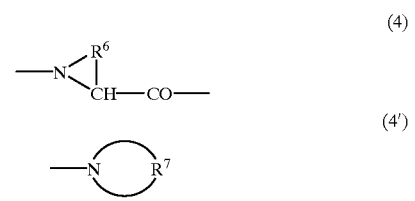

(4')

wherein $R^6$ and $R^7$ represent a bivalent hydrocarbon group forming a 5–7 membered ring optionally substituted or fused with the other 5–7 membered ring, and a part of carbon atoms in said rings optionally replaced with hetero atoms.

DETAILED DESCRIPTION OF THE INVENTION

Figure 1:
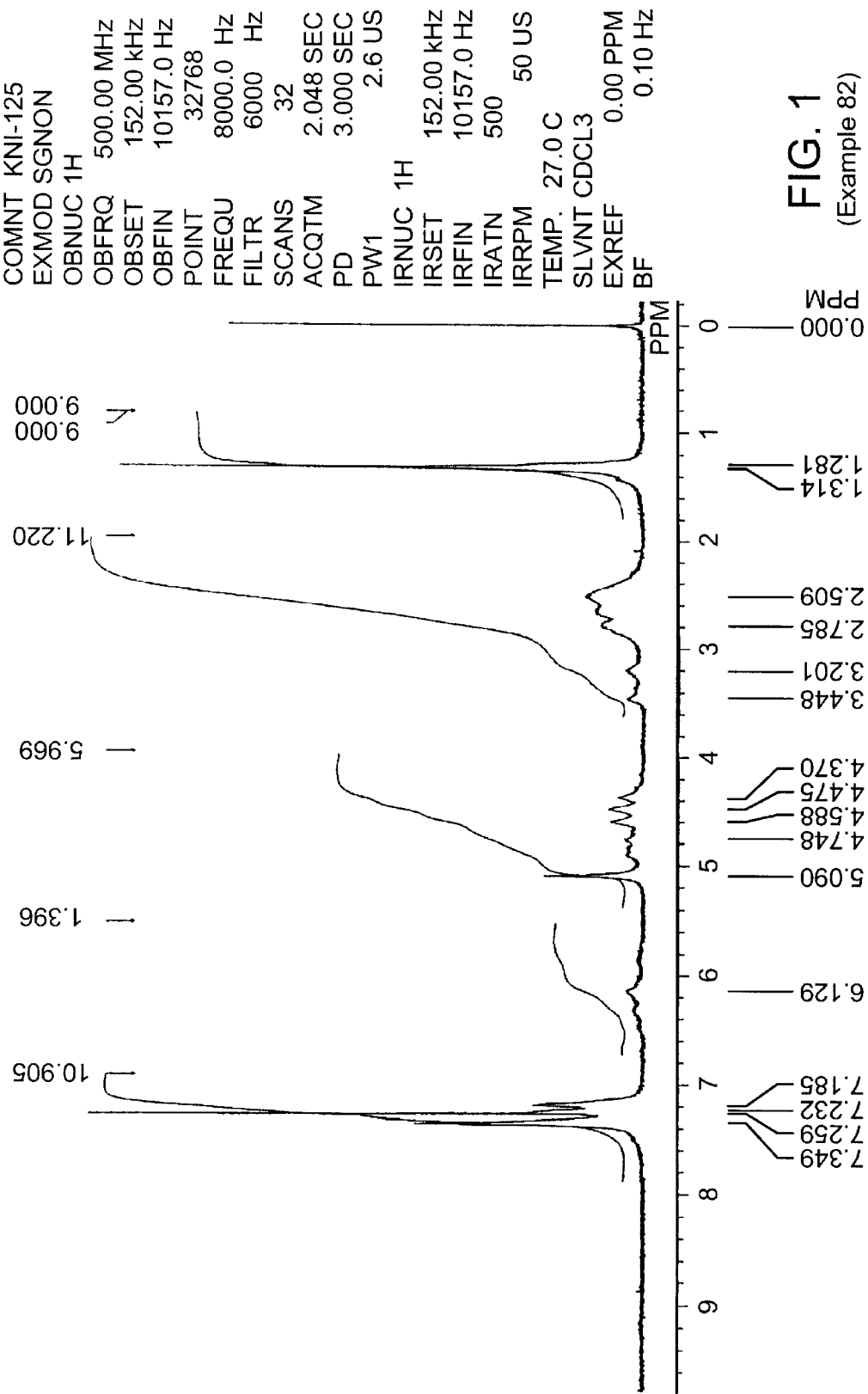
FIGS. 1–6 show NMR spectra of the compounds of Examples 82, 86, 100, 106, 130 and 193, respectively.

The inventors investigated the development of novel HIV protease inhibitors and found that peptide derivatives having an amino acid isostere of a β-amino-α-hydroxycarboxylic acid residue represented by following general formula (8), especially (8'), exhibit a marked inhibition of HIV protease and thus completed the present invention.

Formula (8) and (8'):

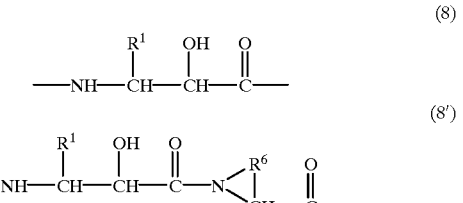

In the general formula (8) and (8'), $R^1$ represents a lower alkyl group, an alicyclic hydrocarbon group, an aromatic hydrocarbon group or a heterocyclic group optionally substituted with an amino group, a mercapto group, a hydroxy group, a carboxy group, a carbamoyl group, an alicyclic hydrocarbon group, an aromatic hydrocarbon group or a heterocyclic group. The inhibitory activity may be derived from a hydrogen bond formed between a hydroxy group of the above-mentioned β-amino-α-hydroxycarboxylic acid residue and Asp25 in the active site of HIV protease, and also from the other hydrogen bond formation by a carbonyl group in the active site. The inhibitory activity is presumed to be obtained by fixing the conformation of the neighboring amino acid residue by said carbonyl group through the amide bond.

One embodiment of the present invention relates to a human immunodeficiency virus (HIV) protease inhibitor peptide derivative represented by the following general formula (9) or a pharmaceutically acceptable salt thereof.

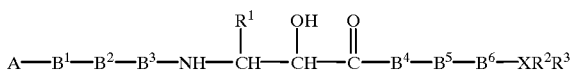

(9)

In the general formula (9), A represents a hydrogen atom or a peptide N-terminal blocking group. The N-terminal blocking group includes groups such as an acetyl group (Ac-), a propionyl group, a butyryl group, an isobutyryl group, a valeryl group, an isovaleryl group, a pivaloyl group, a hexanoyl group, a heptanoyl group, an octanoyl group, a benzyl group (Ph—CH$_2$—), a benzoyl group, a phenylacetyl group (Ph—CH$_2$—CO—), a 3-phenylpropionyl group (Ph—(CH$_2$)$_2$—CO—), a phenylpropenoyl group, a pyridinecarbonyl group (Pyridine-CO—), a quinoline-2-carbonyl group (Quinoline-CO—), a phenoxyacetyl group (Ph—O—CH$_2$—CO—), an o-chlorophenoxyacetyl group (oCl—Ph—O—CH$_2$—CO—), an m-chlorophenoxyacetyl group (mCl—Ph—O—CH$_2$— CO—), a p-chlorophenoxyacetyl group (pCl—Ph—O—CH$_2$—CO—), an o-phenylphenoxyacetyl group (oPh—Ph—O—CH$_2$—CO—), an m-phenylphenoxyacetyl group (mPh—Ph—O—CH$_2$—CO—), a p-phenylphenoxyacetyl group (pPh—Ph—O—CH$_2$—CO—), a 1-naphthoxyacetyl group (1Nap—O—CH$_2$—CO—), a 2-naphthoxyacetyl group (2Nap—O—CH$_2$—CO—), an N-(1-naphthyl)aminoacetyl group (1Nap—NH—CH$_2$—CO—), a glutaryl group {—CO—(CH$_2$)$_3$—CO}, a succinyl group {—CO—(CH$_2$)$_2$—CO—}, a 3-(p-methylbenzyl)thiopropionyl group, a diphenylmethyloxyacetyl group {(C$_6$H$_5$)$_2$CH—O—CH$_2$—CO—}, a bis(p-chloropohenyl)methyloxyacetyl group {(p—ClPh)$_2$CH—O—CH$_2$—CO—}, a (5-isoquinolyloxy)acetyl group (5Isoquinoline-O—CH$_2$—CO—), a naphthalenecarbonyl group, an isoquinoline-1-carbonyl group (1-Isoquinoline-CO—), a furancarbonyl group (furan-CO—), a thiophenecarbonyl group (thiophene-CO—), a methoxycarbonyl group, an ethoxycarbonyl group, a propoxycarbonyl group, a tert-butoxycarbonyl group (Boc-), a benzyloxycarbonyl group (Ph—CH$_2$—O—CO—), a 1-naphthylmethyloxycarbonyl group (1Nap—CH$_2$—O—CO—), a 9-fluorenylmethoxycarbonyl group (Fmoc-), a naphthalene-1-sulfonyl group (1Nap—SO$_2$—), a benzofurancarbonyl group (Benzofuran-CO—), an (E)-4-phenyl-3-butenyl group {(E)Ph—CH=CH—CH$_2$—CO—}, an m-(isopropyloxy)phenyloxyacetyl group {m-(iPrO)-Ph—O—CH$_2$—CO—}, a 5,6,7,8-tetrahydro-1-naphthyloxyacetyl group (1-Tna—O—CH$_2$—CO—), an m-(N-phenylamino)phenyloxyacetyl group {m-(Ph—NH)—Ph—O—CH$_2$—CO}, an m-(morpholinocarbonyl) phenyloxyacetyl group {m-(Morph-CO)—Ph—O—CH$_2$—CO—}, an m-(piperidinocarbonyl)phenyloxyacetyl group {m-(Piper-CO)—Ph—O—CH$_2$—CO—}, a 2,3-dimethylphenyloxyacetyl group (2,3-diMe-Ph—O—CH$_2$—CO—), a 8-quinolyloxyacetyl group (8-Qoa), a 2-pyridyloxyacetyl group (2Pyridine-O—CH$_2$—CO—), a 3-pyridyloxyacetyl group (3Pyridine-O—CH$_2$—CO—) and a 4-pyridyloxacetyl group (4Pyridine-O—CH$_2$—CO—). Among them, aryloxyacetyl groups such as a m-chlorophenoxyacetyl group, an m-phenylphenoxyacetyl group, a 1-naphthoxyacetyl group, a (5-isoquinolyloxy) acetyl group, an m-(N-phenylamino)phenyloxyacetyl group are particularly preferable for the marked elevation of HIV protease inhibitory activity. In addition, the abbreviations used in the above parentheses are used as abbreviations hereinbelow in the remaining portion of the specification.

$B^1$, $B^2$, $B^3$, $B^4$, $B^5$, and $B^6$ represent amino acid residues and include independently naturally occurring or non-naturally occurring amino acid residues and the corresponding amino acids include, for example, glycine (Gly), alanine (Ala), valine (Val), leucine (Leu), isoleucine (Ile), serine (Ser), threonine (Thr), cysteine (Cys), methionine (Met), asparagine (Asn), glutamine (Gln), phenylalanine (Phe), tyrosine (Tyr), tryptophan (Try), aspartic acid (Asp), glutamic acid (Glu), histidine (His), lysine (Lys), arginine (Arg), proline (Pro), β-acetylalanine (Aca), phenylglycine (Phg), α-allylglycine (Alg), α-propargylglycine (Prg), N-cyclohexylmethylglycine {(cHexm)Gly}, N-benzylglycine {(Bzl)Gly}, β-alanine, (βAla), β-cyclohexylalanine, β-(naphthyl)alanine, β-cyanoalanine, β-(cyanomethyl)alanine, β-(sulfonylmethyl)alanine, β-(methanesulfonyl)alanine (Msa), β-(methanesulfonylmethyl)alanine {Met(O)$_2$}, β-sulfanylalanine, β-(methanesulfinyl)alanine {Smc(O)}, sulfanylmethylalanine, β-sulfamoylalanine (Sma), β-methylthioalanine (Mta), β-(dimethylsulfonio)alanine {Mta$^+$(Me)}, D-valine (D-Val), norvaline (Nva), β-(methanesulfonyl)valine (Msv), β-(methylthio)valine (Mtv), norleucine, tert-leucine (Tle), homoserine (Hse), O-methylserine {Ser(Me)}, O-methylthreonine {Thr(Me)}, D-phenylalanine (D-Phe), O-methylaspartic acid, β-hydrazinoaspartic acid {Asp(NHNH$_2$)}, O-methylglutamic acid, hydroxyproline (Hyp), 4-benzyloxypyrrolidine-2-carboxylic acid {Hyp(Bzl)}, 4-methoxypyrrolidine-2-carboxylic acid {Hyp(Me)}, 4-ethoxypyrrolidine-2-carboxylic acid {Hyp(Et)}, 4-allyloxypyrrolidine-2-carboxylic acid {Hyp(Allyl)}, cis-4-cyclohexylpyrrolidine-2-carboxylic acid (Ccp), trans-4-cyclohexylpyrrolidine-2-carboxylic acid (Tcp), 4-benzylpyrrolidine-2-carboxylic acid, 3-phenylpyrrolidine-2-carboxylic acid (Php), cis-4-phenylpyrrolidine-2-carboxylic acid (Cpp), 4-hydroxy-4-phenylpyrrolidine-2-carboxylic acid (Hpp), 4-phenyl-2,5-dihydropyrrole-2-carboxylic acid (Pdp), 4-methylthiopyrrolidine-2-carboxylic acid, 4-phenylthiopyrrolidine-2-carboxylic acid, 4-fluoropyrrolidine-2-carboxylic acid, 4,4-di(methylthio) pyrrolidine-2-carboxylic acid {Pro(SMe)$_2$}, 3,3-dimethylpyrrolidine-2-carboxylic acid (Dmp), 2-aminooctanoic acid, 2-aminoheptanoic acid, indoline-2-carboxylic acid (Inc), octahydroindole-2-carboxylic acid (Oic), octahydrocyclo-penta{b}pyrrole-2-carboxylic acid, L-pipecolic acid {(L)-Pip}, D-pipecolic acid {(D)-Pip}, L-1,2,3,4-tetrahydroisoquinoline-3-carboxylic acid {(L)-Tic}, D-1,2,3,4-tetrahydroisoquinoline-3-carboxylic acid {(D)-Tic}, decahydroisoquinoline-3-carboxylic acid (3Dic), decahydroisoquinoline-1-carboxylic acid (1Dic), 5,5-dimethyl-1,3-thiazolidine-4-carboxylic acid (Dtc), β-amino isobutyric acid (BAIB), β-amino butyric acid (BANB), γ-aminobutyric acid (GABA) and 1,3-thiazolidine-4-carboxylic acid (Thz). In addition, the abbreviations used in the above parentheses are used as abbreviations hereinbelow in the remaining portion of the specification.

The amino group in these amino acids may be substituted with a hydrocarbon group having 12 or less carbon atoms. Such hydrocarbon groups include such groups as methyl, ethyl, benzyl and cyclohexylmethyl groups.

The presence of at least one of the $B^1$, $B^2$, $B^3$, $B^4$, $B^5$ and $B^6$ is sufficient for the definition of general formula, and the presence of $B^3$ and $B^4$, especially $B^3$, is preferable for HIV protease inhibitory activity. The preferred amino acid residues of $B^3$ are residues of valine, leucine, isoleucine, and residues represented by the general formula (10).

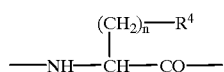

(10)

In general formula (10), n represents 1 or 2, $R^4$ represents a carbamoyl group, a carboxy group, a cyano group, an alkoxycarbonyl group, a hydroxy group, a lower alkoxy group, a lower alkylthio group, a lower alkylsulfonyl group, a sulfonyl group and a sulfamoyl group. Their corresponding amino acids include asparagine, glutamine, aspartic acid, glutamic acid, cyanoalanine, cyanomethylalanine, O-methylaspartic acid, O-methylglutamic acid, serine, O-methylserine, β-methylthioalanine, methionine, β-methanesulfonylalanine, β-(methanesulfonylmethyl)alanine, β-sulfonylalanine, β-sulfonylmethylalanine, β-sulfamoylalanine and β-sulfamoylmethylalanine.

Among them, valine, asparagine, β-methylthioalanine and β-methanesulfonylalanine are particularly preferable.

Furthermore, amino acid residues having $B^4$ represented by the following general formula (11) are also preferable for the improvement of HIV protease inhibitory activity.

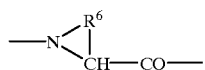

(11)

In the general formula (11), $R^6$ represents a bivalent hydrocarbon group forming a 5–7 membered ring and optionally substituted or fused with the other 5–7 membered ring, and one of which carbon atoms in said rings may be replaced with hetero atoms. The corresponding amino acids include, for example, proline, 4-hydroxypyrrolidine-2-carboxylic acid, 4-benzyloxypyrrolidine-2-carboxylic acid, 4-cyclohexylpyrrolidine-2-carboxylic acid, 4-phenylpyrrolidine-2-carboxylic acid, 3-phenylpyrrolidine-2-carboxylic acid, 4-benzyl pyrrolidine-2-carboxylic acid, 4-methylthiopyrrolidine-2-carboxylic acid, 4-phenylthiopyrrolidine-2-carboxylic acid, 4-fluoropyrrolidine-2-carboxylic acid, 4,4-bis(methylthio)pyrrolidine-2-carboxylic acid, 3,3-dimethylpyrrolidine-2-carboxylic acid, 1,3-thiazolidine-4-carboxylic acid, 5,5-dimethyl-1,3-thiazolidine-4-carboxylic acid, indoline-2-carboxylic acid, octahydroindole-2-carboxylic acid, octahydrocyclopenta{b}pyrrole-2-carboxylic acid, pipecolinic acid, 1,2,3,4-tetrahydroisoquinoline-3-carboxylic acid, 1,2,3,4-tetrahydroisoquinoline-1-carboxylic acid, decahydroisoquinoline-3-carboxylic acid, and decahydroisoquinoline-1-carboxylic acid. Among them, proline, 3,3-dimethylpyrrolidine-2-carboxylic acid, 1,3-thiazolidine-4-carboxylic acid and 5,5-dimethyl-1,3-thiazolidine-4-carboxylic acid are particularly preferable.

The number of peptide bonds in the molecule is preferably decreased for the membrane permeability and in vivo stability, thus the absence of $B^1$ and $B^2$ is preferable, particularly the absence of $B^1$, $B^2$, $B^5$ and $B^6$ is more preferable.

The group represented by $R^1$ includes a lower alkyl group, an alicyclic hydrocarbon group, an aromatic hydrocarbon group or a heterocyclic group. The lower alkyl group includes, for example, a methyl group, a propyl group, an isopropyl group, a butyl group, an isobutyl group, a sec-butyl group, a pentyl group, and a hexyl group. The alicyclic hydrocarbon group includes, for example, a cyclopentyl group and a cyclohexyl group. The aromatic hydrocarbon group includes, for example, a phenyl group, a 4-hydroxyphenyl group and a methoxyphenyl group. The heterocyclic group includes, for example, an imidazolyl group and an indolyl group. The lower alkyl group, alicyclic hydrocarbon group, aromatic hydrocarbon group, and heterocyclic group may be substituted by an amino group, a mercapto group, a hydroxy group, a hydroxyphenyl group, an alkoxyphenyl group, a carboxy group, a carbamoyl group, an alicyclic hydrocarbon group, an aromatic hydrocarbon group or a heterocyclic group. The substituted lower alkyl group includes, for example, a hydroxymethyl group, a mercaptomethyl group, a 1-hydroxyethyl group, a 2-carbamoylethyl group, a 2-carboxyethyl group, a carbamoylmethyl group, a carboxymethyl group, a benzyl group, a (4-hydroxyphenyl)methyl group, a (4-methoxyphenyl)methyl group, a cyclohexylmethyl group, a naphthylmethyl group, an imidazolylmethyl group, an indolylmethyl group, a 2-methylthioethyl group and a 4-aminobutyl group. Said alicyclic hydrocarbon group includes, for example, a cyclopentyl group and a cyclohexyl group. Among them, compounds having an optionally substituted arylmethyl group as $R^1$ are preferable, particularly a benzyl group as $R^1$ is more preferable for the marked elevation of HIV protease inhibitory activity.

In the partial formula —$XR^2R^3$ of formula (9), X represents a nitrogen atom or an oxygen atom, and $R^2$ and $R^3$ represent independently a hydrogen atom or a hydrocarbon group having 12 or less carbon atoms, optionally replaced with an oxygen atom, a nitrogen atom or a sulfur atom, and when X represents an oxygen atom, no $R^3$ exits. The hydrocarbon group in $R^2$ and $R^3$ represents, for example, a methyl group (-Me), an isopropyl group (-iPr), an isobutyl group (-iBu), a sec-butyl group (-sBu), a 2-pentyl group, a 1-ethylpropyl group, a tert-butyl group (-tBu), a neopentyl group, a tert-amyl group (tAmyl), a 3-methyl-2-butyl group, a 2,3-dimethyl-2-butyl group, a cyclohexyl group (—$C_6H_{11}$), a cyclohexylmethyl group (—$CH_2$—$C_6H_{11}$), a cyclopropyl group, a cyclopentyl group, a phenyl group (-Ph), a benzyl group, a naphthyl group and a naphthylmethyl group. The substituted hydrocarbon group includes, for example, a 3-hydroxy-2-methyl-2-propyl group, a 1,1-bis(hydroxymethyl)ethyl group, a 1-hydroxymethyl-2-methylpropyl group, a 1-hydroxy-2-methylbutyl group, a 2-hydroxy-1-phenylethyl group, a 2-hydroxycyclohexyl group (-chex-ol), an o-hydroxyphenyl group (-Ph(o-OH)), an m-hydroxyphenyl group (-Ph(m-OH)) and a p-hydroxyphenyl group (Ph(p-OH)). Furthermore, when X represents a nitrogen atom, said —$NR^2R^3$ group may bind to form a ring, and may be replaced with an oxygen atom, a nitrogen atom or a sulfur atom. These groups include, for example, a 1,2,3,4-tetrahydroisoquinolin-2-yl group, a decahydroquinolin-1-yl group, a decahydroisoquinolin-2-yl group (-Diq), a 1-indolyl group, an octahydroindol-1-yl group, a 2-isoindolyl group, an octahydroisoindol-2-yl group, a 1-pyrrolidinyl group, a 1-piperidinyl group (-piperidine), a 1-morpholinyl group, a 1,3-thiazolidin-3-yl group, a 5,5-dimethyl-1,3-thiazolidine-3-yl group, a etrahydro-1,4-thiazin-3-yl group and a hexahydroazepin-1-yl group. In addition, the abbreviations used in the above parentheses are used as abbreviations hereinbelow in the remaining portion of the specification.

The pharmaceutically acceptable salts of the β-amino-α-hydroxycarboxylic acid derivatives represented by the general formula (9) include, for example, inorganic acid addition salts such as hydrochloride, sulfate, and phosphate, organic acid addition salts such as acetate, oxalate, maleate, metal salts such as sodium, potassium and calcium salt, and organic amine salts such as triethylamine salt.

Another embodiment of the present invention relates to novel β-amino-α-hydroxycarboxylic acid derivatives and salts thereof represented by the following general formula (12) or (12').

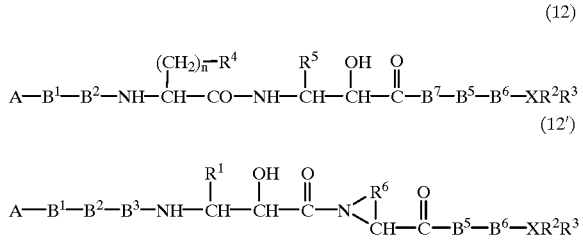

In the general formula (12) and (12'), n represents 1 or 2, A represents a hydrogen atom or a peptide N-terminal protective group, $B^1$, $B^2$, $B^3$, $B^5$, and $B^6$ represents independently single bonds or an amino acid residue optionally the amino group of said amino acid may be substituted with a hydrocarbon residue having 12 or less carbon atoms, $B^7$ represents a single bond or an amino acid residue represented by the following formula (13) with a proviso that $XR^2R^3$ represents the following general formula (13') when $B^7$ is a single bond, X represents a nitrogen atom or an oxygen atom, $R^1$ represents a lower alkyl group, an alicyclic hydrocarbon group, an aromatic hydrocarbon group or a heterocyclic group optionally substituted with an amino group, a mercapto group, a hydroxy group, a carboxy group, a carbamoyl group, an alicyclic hydrocarbon group, an aromatic hydrocarbon group or a heterocyclic group, $R^2$ and $R^3$ each represents a hydrogen atom or an optionally substituted hydrocarbon group having 12 or less carbon atoms which form cycles by forming bonds between said carbon atoms which may optionally be replaced with an oxygen atom, nitrogen or a sulfur atom, with the proviso that no $R^3$ is present when X represents an oxygen atom, $R^4$ represents a carbamoyl group, a carboxy group, a cyano group, an alkoxycarbonyl group, a hydroxy group, a lower alkoxy group, a lower alkylthio group, a lower alkanesulfonyl group, a sulfonyl group, a lower alkanesulfinyl group or a sulfamoyl group, $R^5$ represents an optionally substituted arylmethyl group, and $R^6$ has the same meaning as that in the following general formula (13):

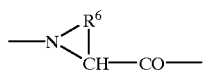

(13)

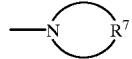

(13')

wherein $R^6$ and $R^7$ represents a bivalent hydrocarbon group forming a 5–7 membered ring optionally substituted or fused with the other 5–7 membered ring, and a part of carbon atoms in said rings optionally replaced with hetero atoms.

The β-amino-α-hydroxycarboxylic acid residue having the structure represented by the general formula (8) can be synthesized by conventional methods. For example, the amino group of the amino acid represented by the general formula (14) is first protected by a known protecting such as a tert-butoxycarbonyl group.

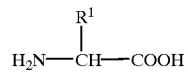

(14)

In the general formula (14), $R^1$ has the same meanings as in the general formula (9). And then, the carboxy group of the protected amino acid is esterified a and hydroxymethyl group is introduced by reduction.

Said hydroxymethyl group is converted into a formyl group by the reaction with an oxidant such as dimethylsulfoxide, which is caused to react with sodium cyanide to make a cyanohydrin compound. The resultant compound is hydrolyzed, for example, with hydrochloric acid to give said β-amino-α-hydroxy-carboxylic acid. The groups of general formula (8) have two asymmetric carbon atoms and therefore, compounds having the residue represented by general formula (8) are often obtained as a mixture of (2S,3S) and (2R,3S) compounds from a starting material of an optically active compound represented by the general formula (14), for example, an S-type compound. In the present invention those mixtures can be used but isomers obtained by a separation with conventional methods such as silica gel column chromatography are preferred. For the separation, a suitable protecting group may be introduced to an amino group or a carboxy group. For example, a compound with general formula (8), such as (2RS,3S)-3-amino-2-hydroxy-4-phenyl-butanoic acid can be separated into (2R,3S) and (2S,3S) isomers by the protection of an amino group with tert-butoxycarbonyl group and a carboxy group with benzyl ester, followed by silica gel column chromatography.

The peptide derivatives represented by general formula (9) of the present invention, including pharmaceutically acceptable salts thereof, inhibit cleavage of a peptide substrate, for example, Ac-Arg-Ala-Ser-Gln-Asn-Tyr-Pro-Val-Val-NH$_2$ (Biochem. Biophys. Res. Comm., 159, 420 (1989)) by chemically synthesized HIV protease, in which two cysteine residues in the reported sequence (Science, 230, 949 (1985)) were replaced with alanine residues, or recombinant HIV protease (Biochemistry, 29, 264 (1990)). Especially, β-amino-α-hydroxycarboxylic acid derivatives represented by general formula (12') exhibit little inhibition against other protease such as pepsin or renin. Therefore, the peptide derivatives of the present invention can be used as a selective inhibitor of HIV protease and may be used for the therapy and prevention of AIDS and AIDS related diseases.

The peptide derivatives represented by general formula (9) can be prepared from amino acid derivatives having the residue represented by general formula (8) by conventional methods in peptide chemistry. L-type amino acid residues are preferred for $B^1$, $B^2$, $B^3$, $B^4$, $B^5$ and $B^6$ in general formula (9). The configuration in the amino acid residue represented by general formula (8) varies with the neighboring amino acid residue. For example, the preferred configuration in the amino acid residue represented by general formula (8) means (2R,3S) when $B^4$ represents a phenylalanine residue, and the preferred configuration means (2S,3S) when $B^4$ represents an amino acid residue in the general formula (11). This may be caused by changes in the conformation of the peptide chain due to the ring structure of amino acid residue in $B^4$ in general formula (11). Separation of isomers may be carried out after peptide bond formation started from isomeric mixture of the amino acid derivatives having a group represented by the general formula (8).

The preferred peptide derivatives represented by the general formula (9) are illustrated in the Tables. The example numbers in Tables 1,2,3,4,5,6 and 7 represent a series of compounds.

Table 8 sets forth the SEQUENCE ID NOS. and peptide sequences corresponding to those peptide derivatives in Tables 1–7 which contain an unbranched sequence of four or more L-amino acids.

TABLE 1

| Example | Chemical Formula | Residual Activity (%) 1 mM | Residual Activity (%) 5 μM |
|---|---|---|---|
| 1 | Boc-Asn-(2R,3S)-AHPBA-NH—CH$_2$—C$_6$H$_{11}$ | 32.8 | |
| 2 | Boc-Phe-Asn-(2R,3S)-AHPBA-NH—CH$_2$—C$_6$H$_{11}$ | 19.5 | |
| 3 | Boc-Asn-(2S,3S)-AHPBA-NH—CH$_2$—C$_6$H$_{11}$ | 52.9 | |
| 4 | Boc-Phe-Asn-(2S,3S)-AHPBA-NH—CH$_2$—C$_6$H$_{11}$ | 20.3 | |
| 5 | Boc-Ser-(2R,3S)-AHPBA-NH—CH$_2$—C$_6$H$_{11}$ | 82.9 | |
| 6 | Boc-Phe-Ser-(2R,3S)-AHPBA-NH—CH$_2$—C$_6$H$_{11}$ | 33.3 | |
| 7 | Boc-Ser-(2S,3S)-AHPBA-NH—CH$_2$—C$_6$H$_{11}$ | 15.6 | |
| 8 | Boc-Phe-Ser-(2S,3S)-AHPBA-NH—CH$_2$—C$_6$H$_{11}$ | 47.0 | |
| 9 | H-Asn-(2R,3S)-AHPBA-NH—CH$_2$—C$_6$H$_{11}$ | 92.1 | |
| 10 | H-Phe-Asn-(2R,3S)-AHPBA-NH—CH$_2$—C$_6$H$_{11}$ | 43.4 | |
| 11 | H-Phe-Asn-(2S,3S)-AHPBA-NH—CH$_2$—C$_6$H$_{11}$ | 16.4 | |
| 12 | H-Ser-(2R,3S)-AHPBA-NH—CH$_2$—C$_6$H$_{11}$ | 89.7 | |
| 13 | H-Phe-Ser-(2R,3S)-AHPBA-NH—CH$_2$—C$_6$H$_{11}$ | 58.9 | |
| 14 | H-Ser-(2S,3S)-AHPBA-NH—CH$_2$—C$_6$H$_{11}$ | 95.5 | |
| 15 | H-Phe-Ser-(2S,3S)-AHPBA-NH—CH$_2$—C$_6$H$_{11}$ | 23.8 | |
| 16 | PhCH$_2$CH$_2$CO-Asn-(2S,3S)-AHPBA-Pro-Ile-Val-NH$_2$ | | 7.0 |
| 17 | PhCH$_2$CH$_2$CO-Asn-(2R,3S)-AHPBA-Pro-Ile-Val-NH$_2$ | 1.5 | 19.3 |
| 18 | H-Val-Val-(2R,3S)-AHPBA-Phe-Val-Val-NH$_2$ | 1.0 | 5.6 |
| 19 | H-Val-Val-(2S,3S)-AHPBA-Phe-Val-Val-NH$_2$ | 5.1 | 32.1 |
| 20 | PhCH$_2$CO-Ser(2R,3S)-AHPBA-Pro-Ile-Val-NH$_2$ | 2.8 | 42.8 |
| 21 | PhCH$_2$CO-Ser-(2R,3S)-AHPBA-Pro-Ile-Val-NH$_2$ | 27.7 | 80.9 |
| 22 | H-Val-Val-(2S,3S)-AHPBA-(D)-Phe-(D)-Val-(D)-Val-NH$_2$ | 52.9 | |
| 23 | H-Val-Val-(2R,3S)-AHPBA-(D)-Phe-(D)-Val-(D)-Val-NH$_2$ | 28.3 | |
| 24 | H-Val-Val-(2S,3S)-AHPBA-(Bzl)Gly-Val-Val-NH$_2$ | 30.4 | |
| 25 | H-Val-Val-(2r,3S)-AHPBA-(Bzl)Gly-Val-Val-NH$_2$ | 2.3 | |
| 26 | PhCH$_2$CH$_2$CO-Ser-(2R,3S)-AHPBA-Pro-Ile-Val-NH$_2$ | 15.7 | 83.1 |
| 27 | PhCH$_2$CH$_2$CO-Asn-(2S,3S)-AHPBA-Pro-MeIle-Val-NH$_2$ | | 92.9 |
| 28 | Boc-(2S,3S)-AHPBA-Pro-Ile-O—C$_6$H$_{11}$ | 63.9 | |
| 29 | Boc-(2R,3S)-AHPBA-Pro-Ile-O—C$_6$H$_{11}$ | 88.3 | |
| 30 | Boc-(2S,3S)-AHPBA-Pro-Ile-NH—CH$_2$—C$_6$H$_{11}$ | 23.4 | |
| 31 | Boc-(2R,3S)-AHPBA-Pro-Ile-NH—CH$_2$—C$_6$H$_{11}$ | 47.4 | |
| 32 | PhCH$_2$-O—CO-Asn-(2S,3S)-AHPBA-Pro-Ile-NH—CH$_2$—C$_6$H$_{11}$ | | 4.0 |
| 33 | Boc-(2S,3S)-AHPBA-(cHexm)Gly-Ile-NH—CH$_2$—C$_6$H$_{11}$ | 85.6 | |

TABLE 2

| Example | Chemical Formula | Residual Activity (%) 1 mM | Residual Activity (%) 5 μM |
|---|---|---|---|
| 34 | Boc-(2R,3S)-AHPBA-(cHexm)Gly-Ile-NH—CH$_2$—C$_2$H$_{11}$ | 87.8 | |
| 35 | PhCH$_2$CH$_2$CO-Asn-(2S,3S)-AHPBA-Pro-β Ala-NH$_2$ | | 60.9 |
| 36 | PhCH$_2$CH$_2$CO-Gln-(2S,3S)-AHPBA-Pro-Ile-Val-NH$_2$ | | 20.6 |
| 37 | PhCH$_2$CH$_2$CO-Asp(NMe2)-(2S,3S)-AHPBA-Pro-Ile-Val-NH$_2$ | | 76.5 |
| 38 | PhCH$_2$CH$_2$CO-Asn-(2S,3S)-AHPBA-Pro-Val-Val-NH$_2$ | | 7.2 |
| 39 | PhCH$_2$CH$_2$CO-Asn-(2S,3S)-AHPBA-Pro-Leu-Val-NH$_2$ | | 48.2 |
| 40 | PhCH$_2$CH$_2$CO-(2S,3S)-AHPBA-Pro-Ile-Val-NH$_2$ | | 74.2 |
| 41 | PhO—CH$_2$CO-Asn-(2S,3S)-AHPBA-Pro-Ile-Val-NH$_2$ | | 1.2 |
| 42 | Pyridine-CO-Asn-(2S,3S)-AHPBA-Pro-Ile-Val-NH$_2$ | | 6.4 |
| 43 | Quinoline-CO-Asn-(2S,3S)-AHPBA-Pro-Ile-Val-NH$_2$ | | 0.8 |
| 44 | H-Ser-Phe-Asn-(2S,3S)-AHPBA-Pro-Ile-Val-NH$_2$ | | 2.2 |
| 45 | H-Ser-Phe-Asn-(2R,3S)-AHPBA-Pro-Ile-Val-NH$_2$ | | 3.2 |
| 46 | Boc-Asn-(2S,3S)-AHPBA-Pro-Ile-NH—CH$_2$—C$_6$H$_{11}$ | | 51.9 |
| 47 | PhCH$_2$CH$_2$CO-Asn-(2S,3S)-AHPBA-Pro-Ile-NH—CH$_2$—C$_6$H$_{11}$ | | 13.2 |
| 48 | Boc-(2S,3S)-AHPBA-Pro-NH—CH$_2$—C$_6$H$_{11}$ | 57.5 | |
| 49 | PhCH$_2$-O—CO-Asn-(2S,3S)-AHPBA-Pro-NH—CH$_2$—C$_6$H$_{11}$ | | 51.9 |
| 50 | Boc-(2S,3S)-AHPBA-Pro-Gln-NH—CH$_2$—C$_6$H$_{11}$ | 62.9 | |
| 51 | Boc-Asn-(2S,3S)-AHPBA-Pro-Ile-NH-iBu | | 85.3 |
| 52 | Boc-Val-(2R,3S)-AHPBA-Phe-Val-NH-iBu | | 94.6 |
| 53 | PhCH$_2$-O—CO-Val-(2R,3S)-AHPBA-Phe-Val-NH-iBu | | 83.4 |
| 54 | PhCH$_2$-O—CO-Val-(2R,3S)-AHPBA-Phe-NH-iBu | | 84.9 |
| 55 | PhCH$_2$-O—CO-Asn-(2S,3S)-AHPBA-Pro-NH-tBu | | 3.5 |
| 56 | PhCH$_2$-O—CO-Asn-(2R,3S)-AHPBA-Pro-NH-tBu | | 95.1 |
| 57 | PhCH$_2$CH$_2$CO-Asn-(2S,3S)-ACHBA-Pro-Ile-Val-NH$_2$ | | 25.7 |
| 58 | PhCH$_2$CH$_2$CO-Asn-(2R,3S)-ACHBA-Pro-Ile-Val-NH$_2$ | | 81.3 |
| 59 | PhCH$_2$CH$_2$CO-His-(2S,3S)-AHPBA-Pro-Ile-Val-NH$_2$ | | 18.2 |
| 60 | PhCH$_2$CH$_2$CO-Ser(Me)-(2S,3S)-AHPBA-Pro-Ile-Val-NH$_2$ | | 10.6 |
| 61 | PhCH$_2$CH$_2$CO-Smc(O)-(2S,3S)-AHPBA-Pro-Ile-Val-NH$_2$ | | 90.9 |
| 62 | PhCH$_2$CH$_2$CO-Msa-(2S,3S)-AHPBA-Pro-Ile-Val-NH$_2$ | | 3.2 |
| 63 | Fmoc-Asn-(2S,3S)-AHPBA-Pro-Ile-Val-NH$_2$ | | 1.0 |
| 64 | 1Nap-O—CH$_2$CO-Asn-(2S,3S)-AHPBA-Pro-Ile-Val-NH$_2$ | | 0.5 |
| 65 | Furan-CO-Asn-(2S,3S)-AHPBA-Pro-Ile-Val-NH$_2$ | | 9.3 |
| 66 | Pyrazine-CO-Asn-(2S,3S)-AHPBA-Pro-Ile-Val-NH$_2$ | | 6.2 |
| 67 | Thiopen-CO-Asn-(2S,3S)-AHPBA-Pro-Ile-Val-NH$_2$ | | 4.9 |
| 68 | H-Inc-Asn-(2S,3S)-AHPBA-Pro-Ile-Val-NH$_2$ | | 5.5 |
| 69 | H-(D)-Tic-Asn-(2S,3S)-AHPBA-Pro-Ile-Val-NH$_2$ | | 29.0 |

TABLE 3

| Example | Chemical Formula | Residual Activity (%) 5 μM | Residual Activity (%) 50 nM |
|---|---|---|---|
| 70 | H-(L)-Tic-Asn-(2S,3S)-AHPBA-Pro-Ile-Val-NH$_2$ | 3.4 | |
| 71 | PhCH$_2$CH$_2$CO-Asn-(2S,3S)-AHPBA(OMe)-Pro-Ile-Val-NH$_2$ | 95.5 | |
| 72 | PhCH$_2$CH$_2$CO-Met(O)$_2$-(2S,3S)-AHPBA-Pro-Ile-Val-NH$_2$ | | 96.8 |
| 73 | PhCH$_2$CH$_2$CO-Ser-(2S,3S)-AHPBA-Pro-Ile-Val-NH$_2$ | 21.5 | |
| 74 | PhCH$_2$CH$_2$CO-Leu-(2S,3S)-AHPBA-Pro-Ile-Val-NH$_2$ | 31.3 | |
| 75 | PhCH CH$_2$CO-Asn-(2S,3S)-AHPBA-Pro-Gln-Ile-NH$_2$ | 62.0 | |
| 76 | PhCH$_2$CH$_2$CO-Asn-(2S,3S)-AHPBA-Pro-Val-NH$_2$ | 39.1 | |
| 77 | PhCH$_2$CH$_2$CO-Asn-(2S,3S)-AHPBA-Pro-Ile-NH$_2$ | 57.0 | |
| 78 | PhCH$_2$—O—CO-Asn-(2S,3S)-AHPBA-(L)-Pip-NH-tBu | 11.7 | |
| 79 | PhCH$_2$—O—CO-Asn-(2S,3S)-AHPBA-(D)-Pip-NH-tBu | 84.0 | |
| 80 | Boc-Asn-(2S,3S)-AHPBA-Pro-NH-tBu | 68.8 | |
| 81 | 1Nap-CH$_2$—O—CO-Asn-(2S,3S)-AHPBA-Pro-NH-tBu | 1.4 | |
| 82 | PhCH$_2$—O—CO-Asn-(2S,3S)-AHPBA-Thz-NH-tBu | 1.3 | |
| 83 | PhCH$_2$—O—CO-Asn-(2S,3S)-AHPBA-Pro-NH-CH$_2$-C(Me)$_3$ | 12.4 | |
| 84 | PhCH$_2$—O—CO-Asn-(2S,3S)-AHPBA-Pro-NH-C$_6$H$_{11}$ | 9.6 | |
| 85 | PhCH$_2$—O—CO-Asn-(2S,3S)-AHPBA-Pro-NH-iPr | 10.0 | |
| 86 | PhCH$_2$—O—CO-Asn-(2S,3S)-AHPBA-Pro-O-tBu | 12.6 | |
| 87 | PhCH$_2$-C-CO-Asn-(2S,3S)-AHPBA-Pro-NH-tAmyl | 5.8 | |
| 88 | PhCH$_2$—O—CO-Asn-(2S,3S)-AHPBA-Pro-NH-cyclopropyl | <10 | |
| 89 | PhCH$_2$—O—CO-Asn-(2S,3S)-AHPBA-Pro-NH-CH(C$_2$H$_5$)$_2$ | <10 | |
| 90 | 1Nap-CH$_2$—O—CO-Msa-(2S,3S)-AHPBA-Pro-NH-tBu | 1.5 | |
| 91 | 1Nap-O—CH$_2$CO-Asn-(2S,3S)-AHPBA-Pro-NH-tBu | | 20.5 |
| 92 | Fmoc-Asn-(2S,3S)-AHPBA-Pro-NH-tBu | | 53.5 |

TABLE 4

| Example | Chemical Formula | Residual Activity (%) 5 μM | Residual Activity (%) 50 nM |
|---|---|---|---|
| 93 | PhCH$_2$-O—CO-Asn-(2S,3S)-AHPBA-Pro-Aib-NH$_2$ | <10 | |
| 94 | (p-ClPh)$_2$CH—O—CH$_2$CO-Asn-(2S,3S)-AHPBA-Pro-NH-tBu | | 37.0 |
| 95 | PhCH$_2$—O—CO-Asn-(2S,3S)-AHPBA-Hyp(Bzl)-NH-tBu | 34.6 | |
| 96 | PhCH$_2$—O—CO-Asn-(2s,3s)-AHPBA-Inc-NH-tBu | 95.2 | |
| 97 | Boc-Sma-(2S,3S)-AHPBA-Pro-NH-tBu | 92.9 | |
| 98 | 1Nap-O—CH$_2$CO-Sma-(2S,3S)-AHPBA-Pro-NH-tBu | | 70.5 |
| 99 | PhCH$_2$—O—CO-Asn-(2S,3S)-AHPBA-Pro-NH-C(Me)$_2$CH$_2$OH | | 62.2 |
| 100 | 1Nap-O—CH$_2$CO-Msa-(2S,3S)-AHPBA-Thz-NH-tBu | | 6.1 |
| 101 | 1Nap-O—CH$_2$CO-Asn-(2S,3S)-AHPBA-Thz-NH-tBu | | 8.7 |
| 102 | PhCH$_2$—O—CO-Asn-(2S,3S)-AHPBA-(L)-Tic-NH-tBu | | 89.2 |

TABLE 4-continued

| Example | Chemical Formula | Residual Activity (%) 5 μM | Residual Activity (%) 50 nM |
|---|---|---|---|
| 103 | PhCH$_2$—O—CO-Asn-(2S,3S)-AHPBA-(D)-Tic-NH-tBu | | 91.4 |
| 104 | PhCH$_2$—O—CO-Asn-(2S,3S)-AHPBA-(L)-Dtc-NH-tBu | | 3.8 |
| 105 | 1Nap-O—CH$_2$CO-Msa-(2S,3S)-AHPBA-Dtc-NH-tBu | | 1.0 |
| 106 | 1Nap-O—CH$_2$CO-Asn-(2S,3S)-AHPBA-Dtc-NH-tBu | | 1.1 |
| 107 | 1Nap-O—CH$_2$-O—CO-Asn-(2S,3S)-AHPBA-Dtc-NH-tBu | | 1.6 |
| 108 | (E)-Ph—CH=CH—CH$_2$CO-Asn-(2S,3S)-AHPBA-Dtc-NH-tBu | | 3.7 |
| 109 | oCl-Ph—O—CH$_2$CO-Asn-(2S,3S)-AHPBA-Dtc-NH-tBu | | 2.7 |
| 110 | oPh-Ph—O—CH$_2$CO-Asn-(2S,3S)-AHPBA-Dtc-NH-tBu | | 3.0 |
| 111 | mPh-Ph-O—CH$_2$CO-Asn-(2S,3S)-AHPBA-Dtc-NH-tBu | | 1.1 |
| 112 | pPh-Ph—O—CH$_2$CO-Asn-(2S,3S)-AHPBA-Dtc-NH-tBu | | 2.0 |
| 113 | mCl-Ph—O—CH$_2$CO-Asn-(2S,3S)-AHPBA-Dtc-NH-tBu | | 2.3 |
| 114 | 1Tna-O—CH$_2$CO-Asn-(2S,3S)-AHPBA-Dtc-NH-tBu | | 2.1 |
| 115 | 5-Isoquinoline-O—CH$_2$CO-Asn-(2S,3S)-AHPBA-Dtc-NH-tBu | | 2.4 |
| 116 | m-(Ph-NH)-Ph-O—CH$_2$CO-Asn-(2S,3S)-AHPBA-Dtc-NH-tBu | | 0.9 |
| 117 | 8Qoa-Asn-(2S,3S)-AHPBA-Dtc-NH-tBu | | 44.1 |
| 118 | Quinoline-CO-Asn-(2S,3S)-AHPBA-Dtc-NH-tBu | | 1.8 |
| 119 | 1Nap-O—CH$_2$CO-Mta-(2S,3S)-AHPBA-Dtc-NH-tBu | | 0.7 |
| 120 | 8Qoa-Mta-(2S,3S)-AHPBA-Dtc-NH-tBu | | 9.5 |
| 121 | 1Nap-O—CH$_2$CO-Mta$^+$(Me)-(2S,3S)-AHPBA-Dtc-NH-tBu.AcO$^-$ | | 32.0 |
| 122 | 1Nap-O—CH$_2$CO-Mta-(2S,3S)-AHPBA-Pro-NH-tBu | | 6.9 |
| 123 | 1Nap-NH—CH$_2$CO-Msa-(2S,3S)-AHPBA-Pro-NH-tBu.AcOH | | 44.6 |
| 124 | 1Nap-NH—CH$_2$CO-Msa-(2S,3S)-AHPBA-Thz-NH-tBu.AcOH | | 28.2 |
| 125 | 1Nap-O—CH$_2$CO-Msa-(2S,3S)-AHPBA-Thz-NH—C(Me)$_2$CH$_2$OH | | 8.2 |

TABLE 5

| Example | Chemical Formula | Residual Activity (%) 5 μM | Residual Activity (%) 50 nM |
|---|---|---|---|
| 126 | 1Nap-O—CH$_2$CO-Msa-(2S,3S)-AHPBA-Pro-NH—C(CH$_2$OH)$_2$Me | | 67.9 |
| 127 | 1Nap-O—CH$_2$CO-Asn-(2S,3S)-AHPBA-Thz-piperidine | <10 | |
| 128 | 1Nap-O—CH$_2$CO-Asn-(2S,3S)-AHPBA-Thz-NH-cyclopropyl | | 10.5 |
| 129 | mPh-Ph—O—CH$_2$CO-Mta-(2S,3S)-AHPBA-Dtc-NH-tBu | | 0.8 |
| 130 | 5-Isoquinoline-O—CH$_2$CO-Mta-(2S,3S)-AHPBA-Dtc-NH-tBU | | 0.9 |
| 131 | 2Nap-O—CH$_2$CO-Msa-(2S,3S)-AHPBA-Pro-NH-tBu | | 28.8 |
| 132 | 1Nap-O—CH$_2$CO-Hse-(2S,3S)-AHPBA-Thz-NH-tBu | | |
| 133 | 1Nap-O—CH$_2$CO-Thr-(2S,3S)-AHPBA-Thz-NH-tBu | | 54.7 |
| 134 | 1Nap-O—CH$_2$CO-Tle-(2S,3S)-AHPBA-Thz-NH-tBu | | 22.6 |
| 135 | 1Nap-O—CH$_2$CO-Msa-(2S,3S)- | | 19.3 |

TABLE 5-continued

| Example | Chemical Formula | Residual Activity (%) 5 μM | Residual Activity (%) 50 nM |
|---|---|---|---|
| 136 | AHPBA-Thz-NH—CH(iPr)CH₂OH Benzofuran-CO-Msa-(2S,3S)-AHPBA-Thz-NH-tBu | | 19.5 |
| 137 | 1Nap-O—CH₂CO-Msa-(2S,3S)-AHPBA-Thz-NH—CH(sBu)CH₂OH | | <10 |
| 138 | Quinoline-CO-Asn-(2S,3S)-AHPBA-Pro-NH-tBu | | 27.3 |
| 139 | 1Nap-CH₂—O—CO-Asp(NHNH₂)-(2S,3S)-AHPBA-Pro-NH-tBu.AcOH | | 27.2 |
| 140 | 1-Isoquinoline-CO-Asn-(2S,3S)-AHPBA-Pro-NH-tBu | | 72.8 |
| 141 | 1Nap-SO₂-Asn-(2S,3S)-AHPBA-Pro-NH-tBu | | 88.2 |
| 142 | 1Nap-O—CH₂CO-Msa-(2S,3S)-AHPBA-Thz-NH-tAmyl | | 11.7 |
| 143 | Biphenyl-CO-Msa-(2S,3S)-AHPBA-Thz-NH-tBu | | <10 |
| 144 | 1Nap-O—CH₂CO-Msa-(2S,3S)-AHPBA-3Dic-NH-tBu | | 95.9 |
| 145 | 1Nap-O—CH₂CO-Msa-(2S,3S)-AHPBA-1Dic-NH-tBu | | 96.6 |
| 146 | 1Nap-O—CH₂CO-Msa-(2S,3S)-AHPBA-Oic-NH-tBu | | 97.5 |
| 147 | 1Nap-O—CH₂CO-Msa-(2S,3S)-AHPBA-Pro-NH—Ph(o-OH) | | 96.7 |
| 148 | 1Nap-O—CH₂CO-Msa-(2S,3S)-AHPBA Pro-NH—Ph(m-OH) | | 88.9 |
| 149 | 1Nap-O—CH₂CO-Msa-(2S,3S)-AHPBA-Pro-NH—Ph(p-OH) | | <10 |
| 150 | 1Nap-O—CH₂CO-Msa-(2S,3S)-AHPBA-Hyp-NH-tBu | | 31.6 |
| 151 | 1Nap-O—CH₂CO-Msa-(2S,3S)-AHPBA-Hyp(Me)-NH-tBu | | 74.8 |
| 152 | 1Nap-O—CH₂CO-Msa-(2S,3S)-AHPBA-Hyp(Et)-NH-tBu | | 91.2 |
| 153 | 1Nap-O—CH₂CO-Msa-(2S,3S)-AHPBA-Hyp(Allyl)-NH-tBU | | 70.6 |
| 154 | 1Nap-O—CH₂CO-Mtv-(2S,3S)-AHPBA-Thz-NH-tBu | | 35.4 |
| 155 | 1Nap-O—CH₂CO-Msv-(2S,3S)-AHPBA-Thz-NH-tBu | | 7.3 |

TABLE 6

| Example | Chemical Formula | Residual Activity (%) 5 μM | Residual Activity (%) 50 nM |
|---|---|---|---|
| 156 | 1Nap-O—CH₂CO-Msa-(2S,3S)-AHPBA-Thz-NH—CH(Ph) CH₂OH | | 94.5 |
| 157 | 1Nap-O—CH₂CO-Msa-(2S,3S)-AHPBA-Thz-Phg-NH₂ | | 93.9 |
| 158 | 1Nap-O—CH₂CO-Msa-(2S,3S)-AHPBA-Thz-NH—chex-ol | | <10 |
| 159 | 1Nap-O—CH₂CO-Msa-(2S,3S)-AHPBA-Thz-Pip-OMe | | 90.8 |
| 160 | 1Nap-O—CH₂CO-Phg-(2S,3S)-AHPBA-Thz-NH-tBu | | 54.8 |
| 161 | 1Nap-O—CH₂CO-Ile-(2S,3S)-AHPBA-Thz-NH-tBu | | 7.0 |
| 162 | 1Nap-O—CH₂CO-Mta-(2S,3S)-AHPBA-Thz-NH-tBu | | 2.9 |
| 163 | 1Nap-O—CH₂CO-Thr(Me)-(2S,3S)-AHPBA-Thz-NH-tBu | | 5.7 |
| 164 | PhCH₂-O-CO-Asn-(2S,3S)-AHPBA-Pdp-NH-tBu | | 49.8 |
| 165 | 1Nap-O—CH₂CO-Nva-(2S,3S)-AHPBA-Thz-NH-tBu | | 10.7 |
| 166 | m-(iPr-O)-Ph—O—CH₂CO-Msa-(2S,3S)-AHPBA-Dtc-NH-tBu | | 2.0 |
| 167 | m-(Piper-CO)-Ph—O—CH₂CO-Msa-(2S,3S)-AHPBA-Thz-NH-tBu | | 25.4 |
| 168 | m-(Morph-CO)-Ph—O—CH₂CO-Msa-(2S,3S)-AHPBA-Thz-NH-tBu | | 44.5 |
| 169 | m-(iPr-O)-Ph—O—CH₂CO-Asn-(2S,3S)-AHPBA-Dtc-NH-tBu | | 1.4 |
| 170 | 1Nap-O—CH₂CO-Alg-(2S,3S)-AHPBA-Thz-NH-tBu | | 7.3 |
| 171 | 2,3-diMe-Ph—O—CH₂CO-Asn-(2S,3S)-AHPBA-Dtc-NH-tBu | | 2.9 |
| 172 | 1Nap-O—CH₂CO-Msa-(2S,3S)-AHPBA-Thz-Gly-NH₂ | | 77.9 |
| 173 | 1Nap-O—CH₂CO-Msa-(2S,3S)-AHPBA-Thz-GABA-NH₂ | | 65.0 |
| 174 | 1Nap-O—CH₂CO-Msa-(2S,3S)-AHPBA-Thz-BAIB-NH₂ | | 46.6 |
| 175 | 1Nap-O—CH₂CO-Msa-(2S,3S)-AHPBA-Thz-BANB-NH₂ | | 33.0 |
| 176 | PhCH₂—O—CO-Asn-(2S,3S)-AHPBA-Pro-NH-sBu | | 82.6 |
| 177 | PhCH₂—O—CO-Asn-(2S,3S)-AHPBA-Pro-NH₂ | | 74.2 |
| 179 | 1Nap-O—CH₂CO-Val-(2S,3S)-AHPBA-Thz-NH-tBu | | 5.5 |
| 180 | 1Nap-O—CH₂CO-Prg-(2S,3S)-AHPBA-Thz-NH-tBu | | 26.0 |
| 181 | 1Nap-O—CH₂CO-Aca-(2S,3S)-AHPBA-Thz-NH-tBu | | 73.0 |
| 182 | PhCH₂—O—CO-Asn-(2S,3S)-AHPBA-Dmp-NH-tBu | | 26.8 |
| 183 | 1Nap-O—CH₂CO-Msa-(2S,3S)-AHPBA-Dmp-NH-tBu | | 4.3 |
| 184 | PhCH₂—O—CO-Asn-(2S,3S)-AHPBA-Php-NH-tBu | | 16.8 |
| 185 | PhCH₂—O—CO-Asn-(2S,3S)-AHPBA-Cpp-NH-tBu | | 96.0 |
| 186 | PhCH₂—O—CO-Asn-(2S,3S)-AHPBA-Tcp-NH-tBu | | 99.5 |
| 187 | PhCH₂—O—CO-Asn-(2S,3S)-AHPBA-Ccp-NH-tBu | | 99.0 |
| 188 | PhCH₂—O—CO-Asn-(2S,3S)-AHPBA-Dmp-NH₂ | | 98.1 |

TABLE 7

| Example | Chemical Formula | Residual Activity (%) 50 nM |
|---|---|---|
| 193 | 5Isoquinoline-O—CH₂—CO-Mta-(2S,3S)-AHPBA-Thz-NH-tBu | 8.4 |
| 194 | 5Isoquinoline-O—CH₂—CO-Val-(2S,3S)-AHPBA-Pro-NH-tBu | 31.0 |
| 195 | 3Pyridine-O—CH₂—CO-Val-(2S,3S)-AHPBA-Thz-NH-tBu | 47.2 |
| 196 | 5Isoquinoline-O—CH₂—CO-Val-(2S,3S)-AHPBA-Thz-NH-tBu | 11.5 |

TABLE 8

| EX. # | PG. # | TABLE # | SEQUENCE | Xaa | SEQ. ID # | PROTECTIVE GROUP |
|---|---|---|---|---|---|---|
| — | 20 (line 2) | — | Arg-Ala-Ser-Gln-Asn-Tyr-Pro-Val-Val | NOT APPLICABLE | 1 | NOT APPLICABLE |
| 16 | 34 | 1 | Asn-Xaa-Pro-Ile-Val | Xaa = (2S,3S)-3-amino-2-hydroxy-4-phenylbutanoic acid | 2 | $PhCH_2CH_2CO-$ |
| 17 | 36 | 1 | Asn-Xaa-Pro-Ile-Val | Xaa = (2R,3S)-3-amino-2-hydroxy-4-phenylbutanoic acid | 2 | $PhCH_2Ch_2CO-$ |
| 18 | 36 | 1 | Val-Val-Xaa-Phe-Val-Val | Xaa = (2R,3S)-3-amino-2-hydroxy-4-phenylbutanoic acid | 3 | NONE |
| 19 | 36 | 1 | Val-Val-Xaa-Phe-Val-Val | Xaa = (2S,3S)-3-amino-2-hydroxy-4-phenylbutanoic acid | 3 | NONE |
| 20 | 37 | 1 | Ser-Xaa-Pro-Ile-Val | Xaa = (2S,3S)-3-amino-2-hydroxy-4-phenylbutanoic acid | 4 | $PhCH_2CO-$ |
| 21 | 37 | 1 | Ser-Xaa-Pro-Ile-Val | Xaa = (2R,3S)-3-amino-2-hydroxy-4-phenylbutanoic acid | 4 | $PhCH_2CO-$ |
| 24 | 38 | 1 | Val-Val-Xaa$_1$-Xaa$_2$-Val-Val | Xaa$_1$ = (2S,3S)-3-amino-2-hydroxy-4-phenylbutanoic acid<br>Xaa$_2$ = N-benzylglycine | 5 | NONE |
| 25 | 38 | 1 | Val-Val-Xaa$_1$-Xaa$_2$-Val-Val | Xaa$_1$ = (2R,3S)-3-amino-2-hydroxy-4-phenylbutanoic acid<br>Xaa$_2$ = N-benzylglycine | 5 | NONE |
| 26 | 38 | 1 | Ser-Xaa-Pro-Ile-Val | Xaa = (2R,3S)-3-amino-2-hydroxy-4-phenylbutanoic acid | 4 | $PhCH_2CH_2CO-$ |
| 27 | 38 | 1 | Asn-Xaa$_1$-Pro-Ile-Val | Xaa$_1$ = (2S,3S)-3-amino-2-hydroxy-4-phenylbutanoic acid<br>Ile$_4$ = MeIle | 2 | $PhCH_2CH_2CO-$ |
| 32 | 43 | 1 | Asn-Xaa-Pro-Ile | Xaa = (2S,3S)-3-amino-2-hydroxy-4-phenylbutanoic acid | 6 | $PhCH_2-O-CO-$ |
| 35 | 46 | 2 | Asn-Xaa$_1$-Pro-Ala | Xaa$_1$ = (2S,3S)-3-amino-hydroxy-4-phenylbutanoic acid<br>Ala$_4$ = beta alanine | 7 | $PhCH_2CH_2CO-$ |
| 36 | 46 | 2 | Gln-Xaa-Pro-Ile-Val | Xaa = (2S,3S)-3-amino-2-hydroxy-4-phenylbutanoic acid | 8 | $PhCH_2CH_2CO-$ |
| 37 | 47 | 2 | Xaa$_1$-Xaa$_2$-Pro-Ile-Val | Xaa$_1$ = dimethyl aspartic acid<br>Xaa$_2$ = (2S,3S)-3-amino-2-hydroxy-4-phenylbutanoic acid | 9 | $PhCH_2CH_2CO-$ |
| 38 | 47 | 2 | Asn-Xaa-Pro-Val-Val | Xaa = (2S,3S)-3-amino-2-hydroxy-4-phenylbutanoic acid | 10 | $PhCH_2CH_2CO-$ |
| 39 | 47 | 2 | Asn-Xaa-Pro-Leu-Val | Xaa = (2S,3S)-3-amino-2-hydroxy-4-phenylbutanoic acid | 11 | $PhCH_2CH_2CO-$ |
| 40 | 47 | 2 | Xaa-Pro-Ile-Val | Xaa = (2S,3S)-3-amino-2-hydroxy-4-phenylbutanoic acid | 12 | $PhCH_2CH_2CO-$ |
| 41 | 48 | 2 | Asn-Xaa-Pro-Ile-Val | Xaa = (2S,3S)-3-amino-2-hydroxy-4-phenylbutanoic acid | 2 | $PhO-CH_2CO-$ |
| 42 | 48 | 2 | Asn-Xaa-Pro-Ile-Val | Xaa = (2S,3S)-3-amino-2-hydroxy-4-phenylbutanoic acid | 2 | Pyridine-CO— |
| 43 | 48 | 2 | Asn-Xaa-Pro-Ile-Val | Xaa = (2S,3S)-3-amino-2-hydroxy-4-phenylbutanoic acid | 2 | Quinoline-CO— |
| 44 | 49 | 2 | Ser-Phe-Asn-Xaa-Pro-Ile-Val | Xaa = (2S,3S)-3-amino-2-hydroxy-4-phenylbutanoic acid | 13 | NONE |
| 45 | 49 | 2 | Ser-Phe-Asn-Xaa-Pro-Ile-Val | Xaa = (2R,3S)-3-amino-2-hydroxy-4-phenylbutanoic acid | 13 | NONE |
| 46 | 49 | 2 | Asn-Xaa-Pro-Ile | Xaa = (2S,3S)-3-amino-2-hydroxy-4-phenylbutanoic acid | 6 | Boc |
| 47 | 50 | 2 | Ser-Asn-Xaa-Pro-Ile | Xaa = (2S,3S)-3-amino-2-hydroxy-4-phenylbutanoic acid | 20 | $PhCH_2CH_2CO-$ |
| 51 | 53 | 2 | Asn-Xaa-Pro-Ile | Xaa = (2S,3S)-3-amino-2-hydroxy-4-phenylbutanoic acid | 6 | Boc |
| 52 | 55 | 2 | Val-Xaa-Phe-Val | Xaa = (2S,3S)-3-amino-2-hydroxy-4-phenylbutanoic acid | 14 | Boc |
| 53 | 57 | 2 | Val-Xaa-Phe-Val | Xaa = (2R,3S)-3-amino-2-hydroxy-4-phenylbutanoic acid | 14 | $PhCH_2-O-CO$ |
| 57 | 61 | 2 | Asn-Xaa-Pro-Ile-Val | Xaa = (2S,3S)-3-N-t-butoxycarbonyl-amino-4-cyclohexyl-2-hydroxybutanoic acid | 2 | $PhCH_2CH_2CO-$ |
| 58 | 62 | 2 | Asn-Xaa-Pro-Ile-Val | Xaa = (2R,3S)-3-N-t-butoxycarbonyl-amino-4-cyclohexyl-2-hydroxybutanoic acid | 2 | $PhCH_2CH_2CO-$ |
| 59 | 63 | 2 | His-Xaa-Pro-Ile-Val | Xaa = (2S,3S)-3-amino-2-hydroxy-4-phenylbutanoic acid | 15 | $PhCH_2CH_2CO-$ |
| 60 | 63 | 2 | Xaa$_1$-Xaa$_2$-Pro-Ile-Val | Xaa$_1$ = O-methylserine<br>Xaa$_2$ = (2S,3S)-3-amino-2-hydroxy-4-phenylbutanoic acid | 9 | $PhCH_2CH_2CO-$ |
| 61 | 64 | 2 | Xaa$_1$-Xaa$_2$-Pro-Ile-Val | Xaa$_1$ = beta-(methanesulfinyl)alanine<br>Xaa$_2$ = (2S,3S)-3-amino-2-hydroxy-4-phenylbutanoic acid | 9 | $PhCH_2CH_2CO-$ |
| 62 | 65 | 2 | Xaa$_1$-Xaa$_2$-Pro-Ile-Val | Xaa$_1$ = beta-(methanesulfonyl)alanine<br>Xaa$_2$ = (2S,3S)-3-amino-2-hydroxy-4-phenylbutanoic acid | 9 | $PhCH_2CH_2CO-$ |
| 63 | 66 | 2 | Asn-Xaa-Pro-Ile-Val | Xaa = (2S,3S)-3-amino-2-hydroxy-4-phenylbutanoic acid | 2 | Fmoc- |
| 64 | 66 | 2 | Asn-Xaa-Pro-Ile-Val | Xaa = (2S,3S)-3-amino-2-hydroxy-4-phenylbutanoic acid | 2 | $1Nap-O-CH_2CO-$ |
| 65 | 67 | 2 | Asn-Xaa-Pro-Ile-Val | Xaa = (2S,3S)-3-amino-2-hydroxy-4-phenylbutanoic acid | 2 | Furan-CO— |
| 66 | 67 | 2 | Asn-Xaa-Pro-Ile-Val | Xaa = (2S,3S)-3-amino-2-hydroxy-4-phenylbutanoic acid | 2 | Pyrazine-CO |
| 67 | 67 | 2 | Asn-Xaa-Pro-Ile-Val | Xaa = (2S,3S)-3-amino-2-hydroxy-4-phenylbutanoic acid | 2 | Thiophen-CO |
| 68 | 67 | 2 | Xaa$_1$-Asn-Xaa$_2$Pro-Ile-Val | Xaa$_1$ = indoline-2-carboxylic acid<br>Xaa$_2$ = (2S,3S)-3-amino-2-hydroxy-4-phenylbutanoic acid | 16 | NONE |
| 70 | 68 | 3 | Xaa$_1$-Asn-Xaa$_2$-Pro-Ile-Val | Xaa$_1$ = L-1,2,3,4-tetrahydroiso-quinoline-3-carboxylic acid<br>Xaa$_2$ = (2S,3S)-3-amino-2-hydroxy-4-phenylbutanoic acid | 16 | NONE |
| 71 | 68 | 3 | Asn-Xaa-Pro-Ile-Val | Xaa = (2S,3S)-3-amino-2-hydroxy-4-(p-methylphenyl)butanoic acid | 2 | $PhCH_2CH_2CO-$ |
| 72 | 68 | 3 | Xaa$_1$-Xaa$_2$-Pro-Ile-Val | Xaa$_1$ = beta-(methanesulfonylmethyl)alanine<br>Xaa$_2$ = (2S,3S)-3-amino-2-hydroxy-4-phenylbutanoic acid | 9 | $PhCH_2CH_2CO-$ |
| 73 | 69 | 3 | Ser-Xaa-Pro-Ile-Val | Xaa = (2S,3S)-3-amino-2-hydroxy-4-phenylbutanoic acid | 4 | $PhCH_2CH_2CO-$ |
| 74 | 69 | 3 | Leu-Xaa-Pro-Ile-Val | Xaa = (2S,3S)-3-amino-2-hydroxy-4-phenylbutanoic acid | 17 | $PhCH_2CH_2CO-$ |
| 75 | 69 | 3 | Asn-Xaa-Pro-Gln-Ile | Xaa = (2S,3S)-3-amino-2-hydroxy-4-phenylbutanoic acid | 18 | $PhCH_2CH_2CO-$ |
| 76 | 70 | 3 | Asn-Xaa-Pro-Val | Xaa = (2S,3S)-3-amino-2-hydroxy-4-phenylbutanoic acid | 19 | $PhCH_2CH_2CO-$ |
| 77 | 70 | 3 | Asn-Xaa-Pro-Ile | Xaa = (2S,3S)-3-amino-2-hydroxy-4-phenylbutanoic acid | 6 | $PhCH_2CH_2CO-$ |
| 93 | 84 | 4 | Asn-Xaa$_1$-Pro-Xaa$_2$ | Xaa$_1$ = (2S,3S)-3-amino-2-hydroxy-4-phenylbutanoic acid<br>Xaa$_2$ = Aib | 7 | $PhCH_2-O-CO-$ |
| 157 | 164 | 6 | Xaa$_1$-Xaa$_2$-Xaa$_3$-Xaa$_4$ | Xaa$_1$ = beta-(methanesulfonyl)alanine<br>Xaa$_2$ = (2S,3S)-3-amino-2-hydroxy-4-phenylbutanoic acid<br>Xaa$_3$ = 1,3-thiazolidine-4-carboxylic acid<br>Xaa$_4$ = phenylglycine | 21 | $1Nap-O-CH_2CO-$ |
| 159 | 169 | 6 | Xaa$_1$-Xaa$_2$-Xaa$_3$-Xaa$_4$ | Xaa$_1$ = beta-(methanesulfonyl)alanine<br>Xaa$_2$ = (2S,3S)-3-amino-2-hydroxy-4-phenylbutanoic acid<br>Xaa$_3$ = 1,3-thiazolidine-4-carboxylic acid<br>Xaa$_4$ = L-pipecolic acid (or D-pipecolic acid; see p. 169) | 21 | $1Nap-O-CH_2CO-$ |
| 172 | 188 | 6 | Xaa$_1$-Xaa$_2$-Xaa$_3$-Gly | Xaa$_1$ = beta-(methanesulfonyl)alanine<br>Xaa$_2$ = (2S,3S)-3-amino-2-hydroxy-4-phenylbutanoic acid<br>Xaa$_3$ = 1,3-thiazolidine-4-carboxylic acid | 22 | $1Nap-O-CH_2CO-$ |

TABLE 8-continued

| EX. # | PG. # | TABLE # | SEQUENCE | Xaa | SEQ. ID # | PROTECTIVE GROUP |
|---|---|---|---|---|---|---|
| 173 | 190 | 6 | $Xaa_1$-$Xaa_2$-$Xaa_3$-$Xaa_4$ | $Xaa_1$ = beta-(methanesulfonyl)alanine<br>$Xaa_2$ = (2S,3S)-3-amino-2-hydroxy-4-phenylbutanoic acid<br>$Xaa_3$ = 1,3-thiazolidine-4-carboxylic acid<br>$Xaa_4$ = gamma-aminobutyric acid | 21 | 1Nap-O—$CH_2$CO— |
| 174 | 192 | 6 | $Xaa_1$-$Xaa_2$-$Xaa_3$-$Xaa_4$ | $Xaa_1$ = beta-(methanesulfonyl)alanine<br>$Xaa_2$ = (2S,3S)-3-amino-2-hydroxy-4-phenylbutanoic acid<br>$Xaa_3$ = 1,3-thiazolidine-4-carboxylic acid<br>$Xaa_4$ = beta-aminoisobutyric acid | 21 | 1Nap-O—$CH_2$CO— |
| 175 | 194 | 6 | $Xaa_1$-$Xaa_2$-$Xaa_3$-$Xaa_4$ | $Xaa_1$ = beta-(methanesulfonyl)alanine<br>$Xaa_2$ = (2S,3S)-3-amino-2-hydroxy-4-phenylbutanoic acid<br>$Xaa_3$ = 1,3-thiazolidine-4-carboxylic acid<br>$Xaa_4$ = beta-aminobutyric acid | 21 | 1Nap-O—$CH_2$CO— |

EX. # refers to the Example number in Tables 1–7.
PG. # refers to the specification page on which the Example appears.
TABLE # refers to the Table in which the Example appears.
SEQUENCE refers to the amino acid sequence corresponding to the peptide of the Example indicated.
Xaa is a description of the unusual or modified amino acid which appears in the corresponding sequence.
SEQ ID # refers to the sequence identifier which appears in the Sequence Listing.
PROTECTIVE GROUP refers to the capping group at the N-terminal end of the peptide corresponding to the Example indicated.

The compounds represented by the general formula (9) and pharmaceutically acceptable salts thereof can be prepared as HIV protease inhibitors by conventional methods with conventional carriers and fillers. For example, tablets, capsules and granules are orally administered and injection preparations are administered intravenously or intramuscularly. Furthermore, adhesive plasters, suppositories, and sprays are used topically.

More specifically, the compounds of the invention can be administered by topical, intravenous, intraperitoneal, oral, and subcutaneous administration. The compounds of the invention may be administered to a domestic animal or to an animal such as a mammal (e.g. mouse, rat or human).

The compounds of the present invention can be made into pharmaceutical compositions by combination with appropriate medical carriers or diluents. For example, the compounds of the present invention can be dissolved in oils, propyleneglycol or other solvents commonly used to prepare injectable solutions. Suitable carriers include physiological saline, polyethylene glycol, ethanol, sesame oil, cremophor and isopropyl myristate. For topical application, the compounds of the invention can be formulated as an ointment or cream.

In terms of composition, compounds should be present between 0.1 to 100%, preferably 1 to 90% based on the total weight of the composition.

The following methods and excipients are merely exemplary and in no way limit the invention.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention may be formulated into preparations for injections by dissolving, suspending, or emulsifying them in aqueous solvents such as normal saline, Dextrose 5%, or non-aqueous solvent, such as vegetable oil, synthetic aliphatic acid glycerides, esters of higher aliphatic acids or propylene glycol; and if desired, with conventional additives such as solubilizers, isotoic agents, suspending agents, emulsifying agents, stabilizers and preservatives.

The compounds of the invention may be combined with other compounds having the desired effect.

The dosage may be suitably determined according to the symptoms, ages, sexes of the patients, and drug form, method and period of administration and doses of 0.001–5 g in a day are generally used for adults in 1–5 divided portions. The most preferable administration is a nasal spray and the effective compound is absorbed through the nasal membrane. In this case, a compound represented by general formula (9) is dissolved in fluorocarbon or saline solution together with preservatives such as benzyl alcohol and an absorption accelerating agent for improved bioavailability and the resultant formulation can be administered by nasal aerosol or inhalation.

The peptide derivatives of the present invention represented by the general formula (9) and pharmaceutically acceptable salts thereof are believed to have no acute toxicity.

The HIV protease inhibitors of the present invention markedly inhibit the HIV protease activity. In addition, they are stable against proteolytic enzymes due to their amino acid isostere. Therefore, the HIV protease inhibitors of the present invention are expected to be useful for the therapy of acquired immunodeficiency syndrome (AIDS) and prevention of HIV infection. More specifically, the compounds may inhibit HIV replication by inhibiting the HIV protease.

The invention will be explained in detail by the following examples:

EXAMPLES

Ref. Example (2RS,3S)-3-N-(t-butoxycarbonyl)amino-2-hydroxy-4-phenylbutanoic acid In 15 ml of purified water, 1.49 g of hydrochloride of (2RS,3S)-3-amino-2-hydroxy-4-phenylbutanoic acid (hereinafter, the amino acid residue thereof is abbreviated as -AHPBA-) was suspended, 1.75 ml of triethylamine was added under ice cooling, then 2.20 g of di-tert-butyl dicarbonate ($Boc_2O$) in 15 ml of tetrahydrofuran (THF) was added, and the resultant mixture was stirred for 14 hr. The reaction mixture was washed with ether and the aqueous layer was condensed to half the volume. The condensate was adjusted to pH 2–3 with citric acid, extracted with ethyl acetate, washed with saturated sodium chloride aqueous solution and dried over anhydrous sodium sulfate. The dried solution was condensed under reduced pressure and hexane was added to the residue to give 1.86 g of crystals of Boc-(2RS,3S)-AHPBA-OH.

Examples 1–8

[Process 1] H-AHPBA-NH—$CH_2$—$C_6H_{11}$.HCl

To a solution of 300 mg (1.15 mmol) of Boc-AHPBA-OH in 2.0 ml of N,N-dimethylformamide (DMF), and 162 μl (1.15 mmol) of cyclohexylmethylamine, 204 mg (1.15 mmol) of N-hydroxynorbornene-2,3-dicarboximide (HONB) and 336 mg (1.73 mmol) of 1-ethyl-3-(3-N,N-dimethylaminopropyl)carbodiimide (EDC) hydrochloride were added, and the mixture was stirred for 14 hr. The reaction mixture was condensed and the residue was dissolved in ethyl acetate and washed successively with 1N-HCl, 5% aqueous solution of sodium hydrogencarbonate and saturated aqueous sodium chloride solution. The washed solution was dried over anhydrous sodium sulfate. The dried solution was evaporated to drynessunder reduced pressure, mixed with 8.65 ml (34.59 mmol) of 4N-HCl dioxane solution under ice cooling and stirred for 60 min. The reaction mixture was condensed and ether was added to the residue to give precipitates. The precipitates were collected and purified using a silica gel column chromatography with $CHCl_3$:MeOH and treated with 4N-HCl dioxane solution to give the title compound (2R,3S: 181 mg, 2S,3S: 132 mg).

[Process 2] Boc-Phe-Asn-OH

In a solution of 10 ml of DMF containing 500 mg (1.38 mmol) of Boc-Phe-succinimide ester (Boc-Phe-Osu), 5 ml of aqueous solution of H-Asn-OH.$Et_3$N [preparation from 365 mg (2.76 mmol) of H-Asn-OH and 384 μl (2.76 mmol) of $Et_3$N] was added under ice cooling and the mixture was stirred for 14 hr. The reaction mixture was evaporated under reduced pressure and the residue was dissolved in ethyl acetate, washed with 1N-HCl and saturated sodium chloride aqueous solution, dried over anhydrous sodium sulfate. The dried solution was condensed under reduced pressure and the oily residue was triturated with ether to give 364 mg of crystals of the title compound with a yield of 70%.

[Process 3] Boc-Phe-Ser-OH

In a 10 ml solution of DMF containing 500 mg (1.38 mmol) of Boc-Phe-OSu was added 5 ml of an aqueous solution of H-Ser-OH.$Et_3$N [preparation from 290 mg (2.76 mmol) of H-Ser-OH and 384 μl (2.76 mmol) of $Et_3$N] and the mixture was stirred for 14 hr. The reaction mixture was evaporated and the residue was dissolved in ethyl acetate and washed with 1N-HCl and saturated sodium chloride aqueous solution, successively, together with salting out. The resultant solution was dried over anhydrous sodium sulfate, evaporated under reduced pressure, and the resulting residue was purified with a silica gel column chromatography ($CHCl_3$:MeOH). The eluate was mixed with ether and n-hexane to give crystals of 150 mg of the title compound with yield of 31%.

[Process 4] Compound of Examples 1–8

In a 2.0 ml solution of DMF containing 20 mg (0.065 mmol) of H-AHPBA-NH—$CH_2$—$C_6H_{11}$ hydrochloride obtained by process 1 were added 9.0 μl (0.065 mmol) of $Et_3$N, 0.065 mmol of an amino acid or a peptide derivative (Boc-Asn-OH: 15.0 mg, Boc-Ser-OH: 13.3 mg, Boc-Phe-Asn-OH: 24.6 mg or Boc-Phe-Ser-OH: 22.8 mg), 11.6 mg (0.065 mmol) of HONB and 18.6 mg (0.097 mmol) of EDC.HCl, successively, and the resultant mixture was stirred for 14 hr. The reaction mixture was evaporated and purified by the following method (a) or (b). The natural amino acids used were the L-form except otherwise stated.

(a) The residue was dissolved in ethyl acetate, washed with 1N-HCl and saturated aqueous sodium chloride solution, and dried over anhydrous sodium sulfate. The dried solution was evaporated under reduced pressure, purified with a silica gel column chromatography ($CHCl_3$:MeOH) and crystallized from ether or n-hexane.

(b) The residue was mixed with water, the formed precipitates were collected by filtration, dried, purified with silica gel column chromatography ($CHCl_3$:MeOH), and crystallized from ether.

Examples 9–15

The compound obtained in Example 1–8 (Process 4) was stirred in 2–3 ml of 4N-HCl in dioxane at room temperature for 60 min, respectively. The reaction mixture was evaporated under reduced pressure, ether was added to the residue and the formed precipitates were collected by centrifugation. The resultant precipitates were dissolved in 1N-acetic acid, purified with reverse-phase column chromatography and lyophilized to give powders of compounds of Examples 9–15, respectively.

Example 16

3-Phenylpropionyl-Asn-(2S,3S)-AHPBA-Pro-Ile-Val-$NH_2$

[Process 1] Diastereomeric separation of Boc-(2RS,3S)-AHPBA-O-benzyl

In 20 ml of DMF, 2.10 g of Boc-(2RS,3S)-AHPBA-OH obtained by the reference Example was dissolved. To the resultant solution were added under ice cooling 1.42 ml of dicyclohexylamine (DCHA) and 1.02 ml of benzyl bromide, successively, and the obtained mixture was stirred for 14 hr. The reaction mixture was filtered and the filtrate was evaporated under reduced pressure. The residue was dissolved in ethyl acetate, washed with 5% aqueous citric acid solution, 5% aqueous sodium hydrogen carbonate solution and saturated aqueous sodium chloride solution, successively, and dried over anhydrous sodium sulfate. The dried solution was evaporated under reduced pressure and the residue was subjected to a flash chromatography using 100 g of silica gel column and eluted with $CHCl_3$ to give 0.87 g of the (2R,3S)-Boc-AHPBA-O-benzyl and 1.20 g of the (2S,3S)-isomer.

TLC: Rf 0.63 for (2R,3S) (chloroform:methanol=60:1)
TLC: Rf 0.41 for (2S,3S) (chloroform:methanol=60:1)

[Process 2] Debenzylation

In 10 ml of ethanol, 1.03 g of Boc-(2S,3S)-AHPBA-O-benzyl obtained by process 1 was dissolved, hydrogen gas was introduced in the presence of 0.10 g of 10% palladium on charcoal and stirred for 60 min. The reaction mixture was filtered, the resultant filtrate was evaporated and crystallized by the addition of hexane to give 0.78 g of Boc-(2S,3S)-AHPBA-OH. Boc-(2R,3S)-AHPBA-OH was obtained from Boc-(2R,3S)-AHPBA-O-benzyl by a similar method.

[Process 3] 3-Phenylpropionyl-Asn-(2S,3S)-AHPBA-Pro-Ile-Val-$NH_2$

Protected amino acids, Boc-Val-OH, Boc-Ile-OH, Boc-Pro-OH, Boc-(2S,3S)-AHPBA-OH and Boc-Asn-OH, and 3-phenylpropionic acid were successively condensed by a solid phase peptide synthetic method [see Peptide Chemistry, 1988, 123 (1989)] using p-methylbenzhydrylamine resin. The resultant protected peptide resin was treated with anhydrous hydrogen fluoride under ice cooling for 60 min in the presence of m-cresol. The hydrogen fluoride was removed, ether was added, the formed precipitates were extracted with 50% aqueous acetic acid solution and the resultant extract was lyophilized. The lyophilized dried powder was dissolved in a mixture of 50% aqueous acetic acid and methanol and the obtained solution was subjected to a reversed-phase HPLC (water-acetonitrile system except otherwise stated and so forth). The fractionated eluate was evaporated and lyophilized to give the title compound.

Analytical HFLC: 23.9 min (The condition was as follows)

Column: YMC AM-302 (4.6×150 mm)

Solvent A: 0.1% trifluoroacetic acid aqueous solution

Solvent B: acetonitrile

Gradient: 10% B for 2 min, then B was increased in 1.67%/min

Flow rate: 0.7 ml/min

FAB-MS: 750 (M+1)

Example 17

3-Phenylpropionyl-Asn-(2R,3S)-AHPBA-Pro-Ile-Val-NH$_2$

The title compound was obtained by a solid phase method similar to Example 16 (Process 3).

Analytical HPLC: 25.3 min (For the condition, see Example 16.)

FAB-MS: 750 (M+1)

Example 18

H-Val-Val-(2R,3S)-AHPBA-Phe-Val-Val-NH$_2$

Example 19

H-Val-Val-(2S,3S)-AHPBA-Phe-Val-Val-NH$_2$

The title compounds were obtained by a solid phase method similar to Example 16 (Process 3) using the protected amino acid, (2RS,3S)-AHPBA-OH. Compounds (2R, 3S) and (2S,3S) were divided during reversed-phase HPLC fractionation.

Analytical HPLC (2R,3S): 20.5 min (For the condition, see: Example 16.)

Analytical HPLC (2S,3S): 21.5 min (For the condition, see: Example 16.)

FAB-MS: 738 (M+1)

Example 20

Phenylacetyl-Ser-(2S,3S)-AHPBA-Pro-Ile-Val-NH$_2$

Example 21

Phenylacetyl-Ser-(2R,3S)-AHPBA-Pro-Ile-Val-NH$_2$

The title compounds were obtained by a solid phase method similar to Example 16 (Process 3). Compounds (2R,3S) and (2S,3S) were divided during reversed-phase HPLC fractionation.

Analytical HPLC (2R,3S): 21.97 min (For the condition, see: Example 16.)

Analytical HPLC (2S,3S): 20.49 min (For the condition, see: Example 16.)

FAB-MS: 709 (M+1)

Example 22

H-Val-Val-(2S,3S)-AHPBA-(D)-Phe-(D)-Val-(D)-Val-NH$_2$

Example 23

H-Val-Val-(2R,3S)-AHFBA-(D)-Phe-(D)-Val-(D)-Val-NH$_2$

The title compounds were obtained by a solid phase method similar to Example 16 (Process 3). Compounds (2R,3S) and (2S,3S) were divided during reversed-phase HFLC fractionation.

Analytical HPLC (2R,3S): 20.48 min (For the condition, see: Example 16.)

Analytical HPLC (2S,3S): 20.98 min (For the condition, see: Example 16.)

FAB-MS: 738 (M+1)

Example 24

H-Val-Val-(2S,3S)-AHPBA-(Bzl)Gly-Val-Val-NH$_2$

Example 25

H-Val-Val-(2R,3S)-AHPBA-(Bzl)Gyl-Val-Val-NH$_2$

The title compounds were obtained by a solid phase method similar to Example 16 (Process 3). Compounds (2R,3S) and (2S,3S) were divided during reversed-phase HPLC fractionation.

Analytical HPLC (2R,3S): 23.09 min (For the condition, see: Example 16.)

Analytical HPLC (2S,3S): 23.45 min (For the condition, see: Example 16.)

FAB-MS: 738 (M+1)

Example 26

3-Phenylpropionyl-Ser-(2R,3S)-AHPBA-Pro-Ile-Val-NH$_2$

The title compound was obtained by a solid phase method similar to Example 16 (Process 3).

Analytical HPLC: 25.96 min (For the condition, see: Example 16.)

FAB-MS: 723 (M+1)

Example 27

3-Phenylpropionyl-Asn-(2S,3S)-APBA-Pro-MeIle-Val-NH$_2$

The title compound was obtained by a solid phase method similar to Example 16 (Process 3).

Analytical HPLC: 16.85 min (For the condition, see: Example 16.)

FAB-MS: 764 (M+1)

Example 28

Boc-(2S,3S)-AHPBA-Pro-Ile-O—C$_6$H$_{11}$

Example 29

Boc-(2R,3S)-AHPBA-Pro-Ile-O—C$_6$H$_{11}$

[Process 1] pMZ-Ile-O—C$_6$H$_{11}$

In a methylene chloride solution of 1.00 g of N-(p-methoxybenzyloxycarbonyl)isoleucine (pMZ-Ile-OH), 0.35 ml of cyclohexanol and 0.84 g of N,N-dicyclohexylcarbodiimide (DCC) were added in the presence of 4 mg of dimethylaminopyridine and the resultant mixture was stirred for 2 hr under ice cooling. The reaction mixture was filtered and the filtrate was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure and the residue was subjected to a silica gel column chromatography (chloroform) to give 1.01 g of pMZ-Ile-O—$C_6H_{11}$.

TLC: Rf 0.56 (chloroform)

[Process 2] Boc-Pro-Ile-O—$C_6H_{11}$

To 207 mg of the protected amino acid obtained by the [process 1], 4 ml of 4N-HCl in dioxane was added in the presence of 100 μl of anisole and the resultant mixture was stirred for 60 min. The reaction mixture was evaporated under reduced pressure and the resultant residue was redissolved in 4 ml of DMF and neutralized with 76 μl of triethylamine under ice cooling. To the neutralized solution, 118 mg of Boc-Pro-OH, 84 mg o N-hydroxybenzotriazol (HOBt) and 126 mg of EDC hydrochloride were added and the obtained mixture was stirred for 14 hr. The reaction mixture was evaporated under reduced pressure and the resultant residue was redissolved in ethyl acetate. The ethyl acetate solution was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure and the residue was subjected to a silica gel column chromatography (chloroform) to give 130 mg of the title compound.

TLC: Rf 0.61 (chloroform:methanol=60:1)

[Process 3] Boc-(2S,3S)-AHPBA-Pro-Ile-O—$C_6H_{11}$ and Boc-(2R,3S)-AHFBA-Pro-Ile-O—$C_6H_{11}$ To 130 mg of the protected peptide obtained by the process 2, 2 ml of 4N-HCl in dioxane was added and the resultant mixture was stirred for 60 min at room temperature. The reaction mixture was evaporated under reduced pressure and the resultant residue was redissolved in 2 ml of DMF and neutralized with 44 μl of triethylamine under ice cooling. To the neutralized solution, 94 mg of Boc-(2RS,3S)-AHPBA-OH, 140 mg of benzotriazol-1-yloxy tris(N,N,-dimethylaminophosphonium)hexafluorophosphate [Bop reagent] and 88 μl of triethylamine were added and the resultant mixture was stirred for 2 hr. The reaction mixture was treated similarly to that in the process 2, except for the chromatography solvent (chloroform:methanol=50:1), to give 54 mg of Boc-(2R,3S)-AHPBA-Pro-Ile-O—$C_6H_{11}$ and 58 mg of Boc-(2S,3S)-AHPBA-Pro-Ile-O—$C_6H_{11}$.

TLC: Rf 0.78, 0.46 (chloroform:methanol=60:1)
FAB-MS: 588 (M+1)

Example 30

Boc-(2S,3S)-AHPBA-Pro-Ile-NH—$CH_2$—$C_6H_{11}$

[Process 1] pMZ-Ile-NH—$CH_2$—$C_6H_{11}$

In a 10 ml of DMF solution containing 1.00 g of HONB ester of pMZ-isoleucine, 0.28 ml of cyclohexylmethylamine and 0.27 ml of N-methylmorpholine were added under ice cooling and the resultant mixture was stirred for 2 hr. The reaction mixture was evaporated under reduced pressure, purified water was added to the residue, the formed precipitates were collected and reprecipitated from DMF and ether to give 0.64 g of the title compound.

TLC: Rf 0.63 (chloroform:methanol=40:1)

[Process 2] H-Ile-NH—$CH_2$—$C_6H_{11}$

In 2 ml of trifluoroacetic acid, 0.50 g of the product obtained by the process 1 was added in the presence of 0.25 ml of anisole under ice cooling and stirred for 60 min. The reaction mixture was evaporated under reduced pressure, redissolved in 5 ml of DMF and neutralized by the addition of triethylamine under ice cooling to prepare a solution of the title compound.

[Process 3] Boc-Pro-Ile-NH—$CH_2$—$C_6H_{11}$

In a solution prepared of 0.33 g of Boc-Pro-OH and 2 ml of DMF, 0.23 ml of triethylamine and 0.22 ml of isobutyl chloro-ormate were added at −15° C. and stirred for 10 min. The reaction solution was added to the entire solution prepared by the process 2 and the resultant mixture was stirred for 60 min. The reaction mixture was treated similarly to that in Example 28 (Process 1) and recrystallized from hexane to give the title compound.

TLC: Rf 0.38 (chloroform:methanol=20:1)

[Process 4] Boc-(2S,3S)-AHPBA-Pro-Ile-NH—$CH_2$—$C_6H_{11}$

Deprotection of 50 mg of the compound obtained by the process 3 was performed similarly to that in Example 28 (Process 3), and the obtained product was dissolved in 3 ml of DMF and neutralized with 17 μl of triethylamine under ice cooling. To the neutralized solution, 35 mg of Boc-(2S,3S)-AHPBA-OH, 52 mg of Bop reagent and 34 μl of triethylamine were added and the resultant mixture was stirred for 2 hr. The reaction mixture was treated similarly to that in Example 28(Process 2), except for the chromatography solvent (chloroform:methanol=30:1), to give 68 mg of the title compound.

TLC: Rf 0.41 (chloroform:methanol=20:1)

Example 31

Boc-(2R,3S)-AHPBA-Pro-Ile-NH—$CH_2$—$C_6H_{11}$

The title compound was synthesized by a similar method of Example 30.

TLC: Rf 0.57 (chloroform:methanol=20:1)
FAB-MS: 601 (M+1)

Example 32

Benzyloxycarbonyl-Asn-(2S,3S)-AHPBA-Pro-Ile-NH—$CH_2$—$C_6H_{11}$

Deprotection of 68 mg of the compound obtained by Example 30 (Process 4) was performed similarly to that in Example 28 (Process 3), and the obtained product was dissolved in 4 ml of DMF and neutralized with 16 μl of triethylamine under ice cooling. To the neutralized solution, 30 mg of N-(benzyloxycarbonyl)asparagine, 17 mg of HOBt, 50 mg of Bop reagent and 39 μl of triethylamine were added and the resultant mixture was stirred for 2 hr. The reaction mixture was treated similarly to that in Example 30 (Process 4) to give 30 mg of the title compound.

TLC: Rf 0.40 (chloroform:methanol=9:1)

FAB-MS: 749 (M+1)

Example 33

Boc-(2S,3S)-AHPBA-(cHexm)Gly-Ile-NH—CH$_2$—C$_6$H$_{11}$

Example 34

Boc-(2R,3S)-AHPBA-(cHexm)Gly-Ile-NH—CH$_2$—C$_6$H$_{11}$

[Process 1] Boc-(cHexm)Gly-OH cyclohexylamine salt

In a methanol solution containing 2.0 g of H-Gly-OMe.HCl, 2.12 ml of cyclohexanecarboxaldehyde was added and the resultant mixture was stirred overnight in H$_2$ atmosphere in the presence of 200 mg of 10% palladium-charcoal. The reaction mixture was filtered and the filtrate was evaporated under reduced pressure to give N-(cyclohexylmethyl)glycine methyl ester [H-(cHexm)Gly-OMe]. The CHCl$_3$ solution of the amino ester obtained above was mixed with 3.32 ml of triethylamine and 4.18 g of Boc$_2$O under ice cooling and the mixture was stirred for 3 hr. The stirred mixture was washed with 5% aqueous citric acid solution, 5N aqueous sodium hydrogencarbonate solution, and saturated aqueous sodium chloride solution, successively, and dried over anhydrous sodium sulfate. The dried solution was evaporated under reduced pressure. The residue was. subjected to a silica gel column chromatography (chloroform) to give oily Boc-(cHexm)Gly-OMe. The oily product was dissolved in methanol and 11.4 ml of 1N-NaOH aqueous solution was added and the resultant solution was stirred for 2 hr at room temperature. The obtained solution was neutralized with citric acid, evaporated and dissolved in ethyl acetate. The ethyl acetate solution was washed with 5% aqueous citric acid solution and saturated aqueous sodium chloride solution, successively, and dried over anhydrous sodium sulfate. The dried solution was evaporated under reduced pressure. The residue was dissolved in methanol and cyclohexylamine was added to the solution, then the resultant solution was evaporated and crystallized from ether to give 1.75 g of the title compound.

TLC: Rf 0.71 (chloroform:methanol:acetic acid=9:1:0.5)

[Process 2] Boc-(cHexm)Gly-Ile-NH—CH$_2$—C$_6$H$_{11}$

Deprotection of 100 mg of the compound obtained by Example 30 (Process 1) was performed similarly to that in Example 28 (Process 3) in the presence of 50 µl of anisol, and the obtained product was dissolved in 5 ml of DMF and neutralized with 36 µl of triethylamine under ice cooling. To the neutralized solution, Boc-(cHexm)Gly-OH obtained from 114 mg of the compound obtained by the process 1, 39 mg of HOBt and 59 mg of EDC hydrochloride were added and the obtained mixture was stirred for 14 hr. The reaction mixture was treated similarly to that in Example 28 (Process 2) to give 115 mg of the title compound.

[Process 3] Boc-(2S,3S)-AHPBA-(cHexm)Gly-Ile-NH—CH$_2$—C$_6$H$_{11}$ and Boc-(2R,3S)-AHPBA-(cHexm)Gly-Ile-NH—CH$_2$—C$_6$H$_{11}$ Deprotection of 50 mg of the compound obtained by the process 2 was performed similarly to that in Example 28 (Process 3), and the obtained product was dissolved in 5 ml of DMF and neutralized with 14 µl of triethylamine under ice cooling. To the neutralized solution, 31 mg of Boc-(2RS,3S)-AHPBA-OH, 46 mg of Bop reagent and 28 µl of triethylamine were added and the resultant mixture was stirred for 2 hr. The reaction mixture was treated similarly to that in Example 28 (Process 2), except for the chromatography solvent (chloroform:methanol=100:1), to give 20.3 mg of Boc-(2S,3S)-AHPBA-(cHexm)Gly-Ile-NH—CH$_2$—C$_6$H$_{11}$ and 9.8 mg of Boc-(2R,3S)-AHPBA-(cHexm)Gly-Ile-NH—CH$_2$—C$_6$H$_{11}$.

TLC: Rf 0.61, 0.46 (chloroform:methanol=20:1)

FAB-MS: 657 (M+1)

Example 35

3-Phenylpropionyl-Asn-(2S,3S)-AHPBA-Pro-β Ala-NH$_2$

The title compound was obtained by a solid phase method similar to Example 16 (Process 3).

Analytical HPLC: 12.33 min (The condition was as follows) Column: YMC AM-302 (4.6×150 mm)

Solvent A: 0.1% trifluoroacetic acid aqueous solution

Solvent B: acetonitrile

Gradient: 20% B for 2 min, then B was increased in 2%/min

Flow rate: 0.7 ml/min

FAB-MS: 609 (M+1)

Example 36

3-Phenylpropionyl-Gln-(2S,3S)-AHPBA-Pro-Ile-Val-NH$_2$

The title compound was obtained by a solid phase method similar to Example 16 (Process 3).

Analytical HPLC: 16.68 min (For the condition, see: Example 35)

FAB-MS: 764 (M+1)

Example 37

3-Phenylpropionyl-Asp(NMe$_2$)-(2S,3S)-AHPB-Pro-Ile-Val-NH$_2$

The title compound was obtained by a solid phase method similar to Example 16 (Process 3).

Analytical HPLC: 18.88 min (For the condition, see: Example 35)

FAB-MS: 778 (M+1)

Example 38

3-Phenylpropionyl-Asn-(2S,3S)-AHPBA-Pro-Val-Val-NH$_2$

The title compound was obtained by a solid phase method similar to Example 16 (Process 3).

Analytical HPLC: 15.97 min (For the condition, see: Example 5)

FAB-MS: 736 (M+1)

Example 39

3-Phenylpropionyl-Asn-(2S,3S)-AHPBA-Pro-Leu-Val-NH$_2$

The title compound was obtained by a solid phase method similar to Example 16 (Process 3).

Analytical HPLC: 17.68 min (For the condition, see: Example 35)

FAB-MS: 750 (M+1)

Example 40

3-Phenylpropionyl-(2S,3S)-AHPBA-Pro-Ile-Val-NH$_2$

The title compound was obtained by a solid phase method similar to Example 16 (Process 3).

Analytical HPLC: 21.84 min (For the condition, see: Example 35)

FAB-MS: 636 (M+1)

Example 41

Phenoxyacetyl-Asn-(2S,3S)-AHPBA-Pro-Ile-Val-NH$_2$

The title compound was obtained by a solid phase method similar to Example 16 (Process 3).

Analytical HFLC: 16.57 min (For the condition, see: Example 35)

FAB-MS: 752 (M+1)

Example 42

2-Pyridinecarbonyl-Asn-(2S,3S)-AHPBA-Pro-Ile-Val-NH$_2$

The title compound was obtained by a solid phase method similar to Example 16 (Process 3).

Analytical HPLC: 13.64 min (For the condition, see: Example 35)

FAB-MS: 723 (M+1)

Example 43

2-Quinolinecarbonyl-Asn-(2S,3S)-AHPBA-Pro-Ile-Val-NH$_2$

The title compound was obtained by a solid phase method similar to Example 16 (Process 3).

Analytical HPLC: 17.81 min (For the condition, see: Example 35)

FAB-MS: 773 (M+1)

Example 44

H-Ser-Phe-Asn-(2S,3S)-AHPBA-Pro-Ile-Val-NH$_2$

The title compound was obtained by a solid phase method similar to Example 16 (Process 3).

Analytical HPLC: 19.13 min (For the condition, see: Example 16)

FAB-MS: 852 (M+1)

Example 45

H-Ser-Phe-Asn-(2R,3S)-AHPBA-Pro-Ile-Val-NH$_2$

The title compound was obtained by a solid phase method similar to Example 16 (Process 3).

Analytical HOLC: 21.54 min (For the condition, see: Example 16)

FAB-MS: 852 (M+1)

Example 46

Boc-Asn-(2S,3S)-AHPBA-Pro-Ile-NH—CH$_2$—C$_6$H$_{11}$

Deprotection of 81 mg of the compound obtained by Example 30 (Process 4) was performed similarly to that in Example 28 (Process 3), and the obtained product was dissolved in 5 ml of DMF and neutralized with 17 µl of triethylamine under ice cooling. To the neutralized solution, 33 mg of Boc-Asn-OH, 22 mg of HOBt and 41 mg of EDC hydrochloride were added and the resultant mixture was stirred for 14 hr. The reaction mixture was treated similarly to that in Example 28 (Process 2), except for the chromatography solvent (chloroform:methanol=20:1) to give 41 mg of the title compound.

TLC: Rf 0.36 (chloroform:methanol=9:1)

Example 47

3-Phenylpropionyl-Asn-(2S,3S)-AHPBA-Pro-Ile-NH—CH$_2$—C$_6$H$_{11}$

Deprotection of 33 mg of the compound obtained by Example 46 was performed similarly to that in Example 28 (Process 3), and the obtained product was dissolved in 4 ml of DMF and neutralized with 6 µl of triethylamine under ice cooling. To the neutralized solution, 7 mg of phenylpropionic acid, 20 mg of Bop reagent and 13 µl of triethylamine were added and the resultant mixture was stirred for 2 hr. The reaction mixture was treated similarly to that in Example 46 to give 6 mg of the title compound.

TLC: Rf 0.82 (chloroform:methanol=9:1)

Analytical HPLC: 24.50 min (For the condition, see Example 16)

FAB-MS: 747 (M+1)

Example 48

Boc-(2S,3S)-AHPBA-Pro-NH—CH$_2$—C$_6$H$_{11}$

[Process 1] Boc-Pro-NH—CH$_2$—C$_6$H$_{11}$

In a DMF solution containing 1.0 g of Boc-Pro-OH, 0.6 ml of cyclohexylmethylamine, 0.83 g of HOBt and 1.07 g of EDC hydrochloride were added under ice cooling, and the resultant mixture was stirred for 14 hr. The reaction mixture was treated similarly to that in Example 46 to give the title compound.

TLC: Rf=0.77 (chloroform:methanol=20:1)

[Process 2] Boc-(2S,3S)-AHPBA-Pro-NH—CH$_2$—C$_6$H$_{11}$

Deprotection of 50 mg of the compound obtained by the process 1 was performed similarly to that in Example 28 (Process 3), and the obtained product was dissolved in 3 ml of DMF and neutralized with 22 µl of triethylamine under ice cooling. To the neutralized solution, 48 mg of Boc-(2S,3S)-AHBPA-OH, 71 mg of Bop reagent and 45 µl of triethylamine were added and the resultant mixture was stirred for 2 hr. The reaction mixture was treated similarly to that in Example 46 to give 62 mg of the title compound.

TLC: Rf 0.57 (chloroform:methanol=9:1)

Example 49

3-Phenylpropionyl-Asn-(2S,3S)-AHPBA-Pro-NH—CH$_2$—C$_6$H$_{11}$

Deprotection of 62 mg of the compound obtained by Example 48 was performed similarly to that in Example 28 (Process 3), and the obtained product was dissolved in 5 ml of DMF and neutralized with 18 µl of triethylamine under ice cooling. To the neutralized solution, 98 mg of p-nitrophenyl ester of benzyloxycarbonyl-Asn-OH

[benzyloxycarbonyl-Asn-ONp], 39 mg of HOBt and 28 μl of N-methylmorpholine were added and the resultant mixture was stirred for 14 hr. The reaction mixture was treated similarly to that in Example 46, except for the chromatography solvent (chloroform:methanol=10:1), and crystallized from ether to give 49 mg of the title compound.

TLC: Rf 0.41 (chloroform:methanol=9:1)

FAB-MS: 636 (M+1)

Example 50

Boc-(2S,3S)-AHPBA-Pro-Gln-NH—$CH_2$—$C_6H_{11}$

[Process 1] pMZ-Gln-NH—$CH_2$—$C_6H_{11}$

In a DMF solution containing 1.0 g of pMZ-Gln-ONp, 0.3 ml of cyclohexylmethylamine and 0.35 ml of triethylamine were added under ice cooling and the resultant mixture was stirred for 14 hr. The reaction mixture was evaporated under reduced pressure and water was added to the resultant residue to give a solid mass. The solid mass was reprecipitated from DMF/ethyl acetate to give 0.71 g of the title compound.

TLC: Rf 0.52 (chloroform:methanol:$H_2O$=8:3:1, lower layer)

[Process 2] Boc-Pro-Gln-NH—$CH_2$—$C_6H_{11}$

Deprotection of 710 mg of the compound obtained by the process 1 was performed similarly to that in Lxampl 30 (Process 2), and the obtained product was dissolved in 3 ml of DMF and neutralized with triethylamine under ice cooling. To the neutralized solution, a mixed anhydride prepared from 452 mg of Boc-Pro-OH, 321 μl of triethylamine and 300 μl of isobutyl chloroformate was added and the resultant mixture was stirred for 1 hr. The reaction mixture was evaporated under reduced pressure and the resultant residue was redissolved in ethyl acetate. The ethyl acetate solution was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure and the, residue was crystallized from ether to give 550 mg of the title compound.

TLC: Rf 0.57 (chloroform:methanol:$H_2O$=8:3:1, lower layer)

[Process 3] Boc-(2S,3S)-AHPBA-Pro-Gln-NH—$CH_2$—$C_6H_{11}$

Deprotection of 100 mg of the compound obtained by the process 2 was performed similarly to that in Example 28 (Process 3), and the obtained product was dissolved in 2 ml of DMF and neutralized with 32 μl of triethylamine under ice cooling. To the neutralized solution, 67 mg of Boc-(2S,3S)-AHPBA-OH, 101 mg of Bop reagent, and 64 μl of triethylamine were added and the resultant mixture was stirred for 2 hr. The reaction mixture was treated similarly to that in Example 46 to give 73 mg of the title compound.

FAB-MS: 616 (M+1)

Example 51

Boc-Asn-(2S,3S)-AHPBA-Pro-Ile-NH—$CH_2$—CH$(CH_3)_2$

[Process 1] Boc-Ile-NH—$CH_2$—$CH(CH_3)_2$

In a DMF solution containing 2.0 g of Boc-Ile-OH, 0.82 ml of isobutylamine, 1.27 g of HOBt and 2.06 g of DCC were added under ice cooling and the resultant mixture was stirred for 14 hr. The reaction mixture, after filtration, was treated similarly to that in Example 50 (Process 2), except for the crystallization solvent (hexane) to give 1.44 g of the title compound.

[Process 2] Boc-Pro-Ile-NH—$CH_2$—$CH(CH_3)_2$

Deprotection of 1.44 g of the compound obtained by the process 1 was performed similarly to that in Example 28 (Process 3), and the obtained product was dissolved in 3 ml of DMF and neutralized with triethylamine under ice cooling. To the neutralized solution, 1.10 g of Boc-Pro-OH, 0.77 g of HOBt and 1.25 g of DCC were added and the resultant mixture was stirred for 14 hr. The reaction mixture was filtered and the filtrate was evaporated under reduced pressure and redissolved in ethyl acetate. The ethyl acetate solution was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure to give 1.00 g of the title compound.

[Process 3] Boc-(2S,3S)-AHPBA-Pro-Ile-NH—$CH_2$—$CH(CH_3)_2$

Deprotection of 50 mg of the compound obtained by the process 2 was performed similarly to that in Example 28 (Process 3), and the obtained product was dissolved in 2 ml of DMF and neutralized with 18 μl of triethylamine under ice cooling. To the neutralized solution, 38 mg of Boc-(2S,3S)-AHPBA-OH, 57 mg of Bop reagent, and 36 μl of triethylamine were added and the resultant mixture was stirred for 2 hr. The reaction mixture was treated similarly to that in Example 46 to give 57 mg of the title compound.

TLC: Rf 0.77 (chloroform:methanol=9:1)

[Process 4] Boc-Asn-(2S,3S)-AHPBA-Pro-Ile-NH—$CH_2$—$CH(CH_3)_2$

Deprotection of 51 mg of the compound obtained by the process 3 was performed similarly to that in Example 28 (Process 3), and the obtained product was dissolved in 5 ml of DMF and neutralized with 13 μl of triethylamine under ice cooling. To the neutralized solution, 64 mg of p-nitrophenyl ester of Boc-Asn-OH, 14 mg of HOBt and 20 μl of N-methylmorpholine were added and the resultant mixture was stirred for 14 hr. The reaction mixture was treated similarly to that in Example 50 (Process 2) to give 45 mg of the title compound.

TLC: Rf 0.39 (chloroform:methanol=9:1)

FAB-MS: 675 (M+1)

Example 52

Boc-Val-(2R,3S)-AHPBA-Phe-Val-NH—$CH_2$—CH$(CH_3)_2$

[Process 1] Boc-Val-NH—$CH_2$—$CH(CH_3)_2$

In a DMF solution containing 2.0 g of Boc-Val-OH, 0.92 ml of isobutylamine, 1.40 g of HOBt and 2.28 g of DCC were added under ice cooling and the resultant mixture was stirred for 14 hr. The reaction mixture was treated similarly to that in Example 51 (Process 1) to give 1.89 g of the title compound.

[Process 2] Boc-Phe-Val-NH—$CH_2$—$CH(CH_3)_2$

Deprotection of 1.89 g of the compound obtained by the process 1 was performed similarly to that in Example 28

(Process 3), and the obtained product was dissolved in 3 ml of DMF and neutralized with triethylamine under ice cooling. To the neutralized solution, 1.85 g of Boc-Phe-OH, 1.06 g of HOBt and 1.72 g of DCC were added and the resultant mixture was stirred for 14 hr. The reaction mixture was filtered and the filtrate was evaporated under reduced pressure and water was added to the residue to give a solid mass. The mass was washed with water and reprecipitated from THF-ether to give 2.20 g of the title compound.

[Process 3] Boc-(2R,3S)-AHPBA-Phe-Val-NH—CH$_2$—CH(CH$_3$)$_2$

Deprotection of 300 mg of the compound obtained by the process 2 was performed similarly to that in Example 28 (Process 3), and the obtained product was dissolved in 10 ml of DMF and neutralized with 99 μl of triethylamine under ice cooling. To the neutralized solution, 211 mg of Boc-(2R, 3S)-AHPBA-OH, 316 mg of Bop reagent, and 198 μl of triethylamine were added and the resultant mixture was stirred for 2 hr. The reaction mixture was treated similarly to that in Example 30 (Process 4) to give 94 mg the title compound.

TLC: Rf 0.41 (chloroform:methanol=9:1)

[Process 4] Boc-Val-(2R,3S)-AHPBA-Phe-Val-NH—CH$_2$—CH(CH$_3$)$_2$

Deprotection of 30 mg of the compound obtained by the process 3 was performed similarly to that in Example 28 (Process 3), and the obtained product was dissolved in 3 ml of DMF and neutralized with 7 μl of triethylamine under ice cooling. To the neutralized solution, 11 mg of Boc-Val-OH, 22 mg of Bop reagent and 14 μl of triethylamine were added and the resultant mixture was stirred for 2 hr. The reaction mixture was treated similarly to that in Example 50 (Process 2) and the obtained precipitates were reprecipitated from DMF-ether to give 17 mg of the title compound.

TLC: Rf 0.88 (chloroform:methanol=9:1)
FAB-MS: 696 (M+1)

Example 53

Benzyloxycarbonyl-Val-(2R,3S)-AHPBA-Phe-Val-NH—CH$_2$—CH(CH$_3$)$_2$

Deprotection of 30 mg of the compound obtained by Example 52 (Process 3) was performed similarly to that in Example 28 (Process 3), and the obtained product was dissolved in 3 ml of DMF and neutralized with 7 μl of triethylamine under ice cooling. To the neutralized solution, 21 mg of benzyloxycarbonyl-Val-OH.DCHA, 22 mg of Bop reagent and 7 μl of triethylamine were added and the resultant mixture was stirred for 2 hr. The reaction mixture was evaporated under reduced pressure and water was added to the resultant residue to give precipitates. The precipitates were washed with water and reprecipitated from THF-ether to give 6 mg of the title compound.

TLC: Rf 0.88 (chloroform:methanol=20:1)
FAB-MS: 730 (M+1)

Example 54

Benzyloxycarbonyl-Val-(2R,3S)-AHPBA-Phe-NH—CH$_2$—CH(CH$_3$)$_2$

[Process 1] Boc-Phe-NH—CH$_2$—CH(CH$_3$)$_2$

In a DMF solution containing a mixed anhydride prepared from 2.0 g oi Boc-Phe-OH, 1.15 ml of triethylamine and 1.08 ml of isobutyl chloroformate, 1.50 ml of isobutylamine was added under ice cooling and the resultant mixture was stirred for 14 hr. The reaction mixture was treated similarly to that in Example 51 (Process 1) to give 1.91 g of the title compound.

TLC: Rf 0.82 (chloroform:methanol=20:1)

[Process 2] Boc-(2R,3S)-AHPBA-Phe-NH—CH$_2$—CH(CH$_3$)$_2$

Deprotection of 100 mg of the compound obtained by the process 1 was performed similarly to that in Example 28 (Process 3), and the obtained product was dissolved in 5 ml of DMF and neutralized with 43 μl of triethylamine under ice cooling. To the neutralized solution, 92 mg of Boc-(2R, 3S)-AHPBA-OH, 138 mg of Bop reagent and 87 μl of triethylamine were added and the resultant mixture was stirred for 2 hr. The reaction mixture was evaporated under reduced pressure and water was added to the resultant residue to give precipitates. The precipitates were washed with water and reprecipitated from DMF-ether to give 98 mg of the title compound.

TLC: Rf 0.86 (chloroform:methanol=9:1)

[Process 3] Benzyloxycarbonyl-Val-(2R,3S)-AHPBA-Phe-NH—CH$_2$—CH(CH$_3$)$_2$

Deprotection of 30 mg of the compound obtained by the process 2 was performed similarly to that in Example 28 (Process 3), and the obtained product was dissolved in 3 ml of DMF and neutralized with 8 μl of triethylamine under ice cooling. To the neutralized solution, 26 mg of benzyloxycarbonyl-Val-OH.DCHA, 27 mg of Bop reagent and 8 μl of triethylamine were added and the resultant mixture was stirred for 2 hr. The reaction mixture was evaporated under reduced pressure and water was added to the resultant residue to give precipitates. The precipitates were washed with water and reprecipitated from THF-ether to give 10 mg of the title compound.

TLC: Rf 0.36 (chloroform:methanol=20:1)
FAB-MS: 631 (M+1)

Example 55

Benzyloxycarbonyl-Asn-(2S,3S)-AHPBA-Pro-NH-tBu

[Process 1] Boc-Pro-NH-tBu

In a DMF solution of 0.50 g of Boc-Pro-OH, 0.24 ml of tert-butylamine, 0.36 g of HOBt and 0.53 g of EDC hydrochloride were added under ice cooling and the mixture was stirred for 14 hr. The reaction mixture was treated similarly to that in Example 28 (Process 2) to give 373 mg of the title compound.

TLC: Rf 0.41 (chloroform:methanol=20:1)

[Process 2] Boc-(2S,3S)-AHPBA-Pro-NH-tBu

Deprotection of 100 mg of the compound obtained by the process 1 was performed similarly to that in Example 28 (Process 3), and the obtained product was dissolved in 5 ml of DMF and neutralized with 52 μl of triethylamine under ice cooling. To the neutralized solution, 100 mg of Boc-(2S, 3S)-AHPBA-OH, 164 mg of Bop reagent, 104 μl of triethylamine were added and the resultant mixture was stirred for 2 hr. The reaction mixture was treated similarly to that in Example 46 and crystallized from hexane to give 69 mg of the title compound.

TLC: Rf 0.38 (chloroform:methanol=9:1)

[Process 3] Benzyloxycarbonyl-Asn-(2S,3S)-AHPBA-Pro-NH-tBu

Deprotection of 30 mg of the compound obtained by the process 2 was performed similarly to that in Example 28 (Process 3), and the obtained product was dissolved in 3 ml of DMF and neutralized with 9.3 μl of triethylamine under ice cooling. To the neutralized solution, 52 mg of benzyloxycarbonyl-Asn-ONp, 21 mg of HOBt and 15 μl of N-methylmorpholine were added and the resultant solution was stirred for 14 hr. The reaction mixture was treated similarly to that in Example 49, except for the crystallization solvent (ether-hexane), to give 22 mg of the title compound.

TLC: Rf 0.29 (chloroform:methanol=9:1)

FAB-MS: 596 (M+1)

Example 56

Benzyloxycarbonyl-Asn-(2R,3S)-AHPBA-Pro-NH-tBu

The title compound was synthesizerd by a similar method with that in Example 55.

Analytical HPLC: 18.36 min (For the condition, see: Example 35).

FAB-MS: 596 (M+1)

Example 57

3-Phenylpropionyl-Asn-(2S,3S)-ACHBA-Pro-Ile-Val-NH$_2$

[Process 1] (2S,3S)-3-N-t-butoxycarbonylamino-4-cyclohexyl-2-hydroxybutanoic acid In 2.5 ml of ethanol, 148 mg of Boc-(2S,3S)-AHPBA-OH was dissolved and 15 mg of 5% Rh/Al$_2$O$_3$ was added to the solution. The resultant mixture was stirred for 5 days at room temperature in the hydrogen atmosphere at 4.5 kg/cm$^2$. The reaction mixture was filtered to separate the catalyst using celite and the filtrate was evaporated under reduced pressure to give the title compound (hereinafter abbreviated as Boc-(2S,3S)-ACHBA-OH).

[Process 2] 3-Phenylpropionyl-Asn-(2S,3S)-ACHBA-Pro-Ile-Val-NH$_2$

The title compound was obtained by a solid phase method similar to Example 16 (Process 3) from Boc-(2S,3S)-ACHBA-OH prepared above.

Analytical HPLC: 19.46 min (For the condition, see: Example 35)

FAB-MS: 756 (M+1)

Example 58

3-Phenylpropionyl-Asn-(2R,3S)-ACHBA-Pro-Ile-Val-NH$_2$

[Process 1] Boc-(2R,3S)-ACHBA-OH

In 2.5 ml of ethanol, 148 mg of Boc-(2R,3S)-AHPBA-OH was dissolved and 15 mg of 5% Rh/Al$_2$O$_3$ was added to the solution. The resultant mixture was stirred for 5 days at room temperature in the hydrogen atmosphere at 4.5 kg/cm$^2$. The reaction mixture was filtered using celite to separate the catalyst and the filtrate was evaporated under reduced pressure to give the title compound.

[Process 2] 3-Phenylpropionyl-Asn-(2R,3S)-ACHBA-Pro-Ile-Val-NH$_2$

The title compound was obtained by a solid phase method similar to Example 16 (Process 3) from Boc-(2R,3S)-ACHBA-OH prepared above.

Analytical HPLC: 21.41 min (For the condition, see: Example 35)

FAB-MS: 756 (M+1)

Example 59

3-Phenylpropionyl-His-(2S,3S)-AHPBA-Pro-Ile-Val-NH$_2$

The title compound was obtained by a solid phase method similar to Example 16 (Process 3).

Analytical HPLC: 15.22 min (For the condition, see: Example 35)

FAB-MS: 773 (M+1)

Example 60

3-Phenylpropionyl-Ser(Me)-(2S,3S)-AHPBA-Pro-Ile-Val-NH$_2$

[Process 1] Boc-Ser(Me)-OH.DCHA

In a DMF solution containing 2.00 g of Boc-Ser-OH, 0.86 g of sodium hydride (60% oily suspension) was added under ice cooling and the resultant mixture was stirred for 30 min. To the resultant solution, 0.72 ml of methyl iodide was added and the resultant solution was stirred for 3 hr. The reaction mixture was neutralized with citric acid and evaporated under reduced pressure. The obtained residue was redissolved in ethyl acetate, and the solution was washed with 5% aqueous citric acid solution and saturated aqueous sodium chloride solution. successively, and dried over anhydrous sodium sulfate. The dried solution was evaporated under reduced pressure. The residue was subjected to a silica gel column chromatography (chloroform:methanol=10:1) and crystallized as its DCHA salt from n-hexane to give 0.79 g of the title compound.

TLC: Rf 0.45(chloroform:methanol:acetic acid=9:1:0.5)

[Process 2] 3-Phenylpropionyl-Ser(Me)-(2S,3S)-AHPBA-Pro-Ile-Val-NH$_2$

The title compound was obtained by a solid phase method similar to Example 16 (Process 3).

Analytical HFLC: 20.54 min (For the condition, see: Example 35)

FAB-MS: 737 (M+1)

Example 61

3-Phenylpropionyl-Smc(O)-(2S,3S)-AHPBA-Pro-Ile-Val-NH$_2$

[Process 1] N-(tert-Butoxycarbonyl) methanesulfinylalanine

In 10 ml of purified water, 1.0 g of S-methyl-L-cysteine was suspended and 1.54 ml of triethylamine was added under ice cooling. To this was added a solution of 1.94 g of Boc$_2$O in 10 ml of THF and the resultant reaction mixture was stirred for 14 hr. The reaction mixture was washed with ether and the aqueous layer was evaporated up to the half volume. The condensed solution was adjusted to pH 2–3 with citric acid and extracted with ethyl acetate, washed with saturated aqueous sodium chloride solution. To the organic solution, was added an aqueous solution of 1.36 g of sodium perborate tetrahydrate, and the reaction mixture was stirred overnight. The organic layer was washed with saturated sodium chloride aqueous solution and dried over anhydrous sodium sulfate. The dried solution was evaporated under reduced pressure and ether was added to the residue to crystallize 1.33 g of the title compound [Boc-Smc(O)—OH].

TLC: Rf 0.51 (n-BuOH:acetic acid:pyridine:$H_2O$=4:1:1:2)

[Process 2] 3-Phenylpropionyl-Smc(O)-(2S,3S)-AHPBA-Pro-Ile-Val-$NH_2$

The title compound was obtained by a solid phase method similar to Example 16 (Process 3).

Analytical HPLC: 17.86 and 18.61 min (For the condition see: Example 35)

FAB-MS: 769 (M+1)

Example 62

3-Phenylpropionyl-Msa-(2S,3S)-AHPBA-Pro-Ile-Val-$NH_2$

[Process 1] N-(tert-Butoxycarbonyl)methanesulfonylalanine

In 2 ml of chloroform, 300 mg of Boc-Smc(O)—OH was dissolved, 206 mg of m-chloroperbenzoic acid was added and the resultant mixture was stirred for 14 hr. The reaction mixture was filtered, and the filtrate was evaporated and crystallized by the addition of a mixture of ether and n-hexane to give 267 mg of the title compound.

TLC: Rf 0.60 (n-BuOH:acetic acid:pyridine:$H_2O$=4:1:1:2)

[Process 2] 3-Phenylpropionyl-Msa-(2S,3S)-AHPBA-Pro-Ile-Val-$NH_2$

The title compound was obtained by a solid phase method similar to Example 16 (Process 3).

Analytical HPLC: 19.21 min (For the condition, see: Example 35)

FAB-MS: 785 (M+1)

Example 63

Fmoc-Asn-(2S,3S)-AHPBA-Pro-Ile-Val-$NH_2$

The title compound was obtained by a solid phase method similar to Example 16 (Process 3).

Analytical HPLC: 22.57 min (For the condition, see: Example 35)

FAB-MS: 840 (M+1)

Example 64

1-Naphthoxyacetyl-Asn-(2S,3S)-AHPBA-Pro-Ile-Val-$NH_2$

The title compound was obtained by a solid phase method similar to Example 16 (Process 3).

Analytical HPLC: 20.06 min (For the condition, see: Example 35)

FAB-MS: 802 (M+1)

Example 65

Furancarbonyl-Asn-(2S,3S)-AHPBA-Pro-Ile-Val-$NH_2$

The title compound was obtained by a solid phase method similar to Example 16 (Process 3).

Analytical HPLC: 12.92 min (For the condition, see: Example 35)

FAB-MS: 712 (M+1)

Example 66

Pyrazinecarbonyl-Asn-(2S,3S)-AHPBA-Pro-Ile-Val-$NH_2$

The title compound was obtained by a solid phase method similar to Example 16 (Process 3).

Analytical HPLC: 11.54 min (For the condition, see: Example 35)

FAB-MS: 724 (M+1)

Example 67

Thiophenecarbonyl-Asn-(2S,3S)-AHPBA-Pro-Ile-Val-$NH_2$

The title compound was obtained by a solid phase method similar to Example 16 (Process 3).

Analytical HPLC: 14.18 min (For the condition, see: Example 35)

FAB-MS: 728 (M+1)

Example 68

L-Indoline-2-carbonyl-Asn-(2S,3S)-AHPBA-Pro-Ile-Val-$NH_2$

The title compound was obtained by a solid phase method similar to Example 16 (Process 3).

Analytical HPLC: 14.41 min (For the condition, see: Example 35)

FAB-MS: 763 (M+1)

Example 69

H-(D)-Tic-Asn-(2S,3S)-AHPBA-Pro-Ile-Val-$NH_2$

Example 70

H-(L)-Tic-Asn-(2S,3S)-AHPBA-Pro-Ile-Val-$NH_2$

D- and L-form of 1,2,3,4-Tetrahydroisoquinoline-3-carbonyl-Asn-(2S,3s)-AHPBA-Pro-Ile-Val-$NH_2$ were obtained by a solid phase method similar to Example 16 (Process 3).

Analytical HPLC (D): 11.17 min (For the condition, see: Example 35)

Analytical HPLC (L): 12.52 min (For the condition, see: Example 35)

FAB-MS: 777 (M+1)

Example 71

3-Phenylorolionyl-Asn-(2S,3S)-AHPBA(OMe)-Pro-Ile-Val-$NH_2$

The title compound was obtained by a solid phase method similar to Example 16 (Process 3). AHPBA(OMe) means 3-amino-2-hydroxy-4-(p-methoxyphenyl)butanoic acid resudure.

Analytical HPLC: 18.01 min (For the condition, see: Example 35)

FAB-MS: 780 (M+1)

Example 72

3-Phenylpropionyl-Met(O)$_2$-(2S,3S)-AHPBA-Pro-Ile-Val-NH$_2$

The title compound was obtained by a solid phase method similar to Example 16 (Process 3).

Analytical HPLC: 18.68 min (for the conditions see: Example 35)

FAB-MS: 799 (M+1)

Example 73

3-Phenylpropionyl-Ser-(2S,3S)-AHPBA-Pro-Ile-Val-NH$_2$

The title compound was obtained by a solid phase method similar to Example 16 (Process 3).

Analytical HPLC: 18.17 min (For the condition, see: Example 35)

FAB-MS: 723 (M+1)

Example 74

3-Phenylpropionyl-Leu-(2S,3S)-AHPBA-Pro-Ile-Val-NH$_2$

The title compound was obtained by a solid phase method similar to Example 16 (Process 3).

Analytical HPLC: 25.03 min (For the condition, see: Example 35)

FAB-MS: 749 (M+1)

Example 75

3-Phenylpropionyl-Asn-(2S,3S)-AHPBA-Pro-Gln-Ile-NH$_2$

The title compound was obtained by a solid phase method similar to Example 16 (Process 3).

Analytical HPLC: 21.78 min (For the condition, see: Example 35)

FAB-MS: 779 (M+1)

Example 76

3-Phenylpropionyl-Asn-(2S,3S)-AHPBA-Pro-Val-NH$_2$

The title compound was obtained by a solid phase method similar to Example 16 (Process 3).

Analytical HPLC: 14.78 min (For the condition, see: Example 35)

FAB-MS: 637 (M+1)

Example 77

3-Phenylpropionyl-Asn-(2S,3S)-AHPBA-Pro-Ile-NH$_2$

The title compound was obtained by a solid phase method similar to Example 16 (Process 3).

Analytical HPLC: 16.13 min (For the condition, see: Example 35)

FAB-MS: 651 (M+1)

Example 78

Benzyloxycarbonyl-Asn-(2S,3S)-AHPBA-(L)-Pip-NH-tBu

Example 79

Benzyloxycarbonyl-Asn-(2S,3S)-AHPBA-(D)-Pip-NH-tBu

[Process 1] Boc-(DL)-Pip-NH-tBu

In a DMF solution containing 0.20 g of N-(tert-butoxycarbonyl)-(DL)-pipecolic acid, 92 µl of tert-butylamine, 134 mg of HOBt and 200 mg of EDC hydrochloride were added under ice cooling and the resultant mixture was stirred for 14 hr. The reaction mixture was treated similarly to that in Example 30 (Process 3) to give 108 mg of the title compound TLC: Rf 0.39 (chloroform:methanol=20:1)

[Process 2] Boc-(2S,3S)-AHPBA-(DL)-Pip-NH-tBu

Deprotection of 100 mg of the compound obtained by the process 1 was performed similarly to that in Example 28 (Process 3), and the obtained product was dissolved in 5 ml of DMF and neutralized with 49 µl of triethylamine under ice cooling. To the neutralized solution, 104 mg of Boc-(2S,3S)-AHPBA-OH, 156 mg of Bop reagent, 98 µl of triethylamine were added and the resultant mixture was stirred for 2 hr. The reaction mixture was treated similarly to that in Example 45 to give 109 mg of the title compound.

TLC: Rf 0.65 (chloroform:methanol=9:1)

[Process 3] Benzyloxycarbonyl-Asn-(2S,3S)-AHPBA-(L)-Pip-NH-tBu and Benzyloxycarbonyl-Asn-(2S,3S)-AHPBA-(D)-Pip-NH-tBu Deprotection of 100 mg of the compound obtained by the process 2 was performed similarly to that in Example 28 (Process 3), and the obtained product was dissolved in 5 ml of DMF and neutralized with 30 µl of triethylamine under ice cooling. To the neutralized solution, 169 mg of benzyloxycarbonyl-Asn-ONp, 66 mg of HOBt and 48 µl of N-methylmorpholine were added and the resultant solution was stirred for 14 hr. The reaction mixture was treated similarly to that in Example 55 (Process 3) to give 58 mg of benzyloxycarbonyl-Asn-(2S,3S)-AHPBA-(DL)-Pip-NH-tBu.

TLC: Rf 0.55 (chloroform:methanol=9:1)

The obtained mixture was dissolved in methanol, fractionated by a reversed-phase HPLC and lyophilized to give the title compounds.

FAB-MS: 610 (M+1)

Example 80

Boc-Asn-(2S,3S)-AHPBA-Pro-NH-tBu

Deprotection of 85 mg of the compound obtained by Example 55 (Process 2) was performed similarly to that in Example 28 (Process 3), and the obtained product was dissolved in 3 ml of DMF and neutralized with 27 µl of triethylamine under ice cooling. To the neutralized solution, 134 mg of Boc-Asn-ONp, 58 mg of HOBt, 42 µl of N-methylmorpholine were added and the resultant solution was stirred for 14 hr. The reaction mixture was treated similarly to that in Example 55 (Process 3) to give 51 mg of the title compound.

TLC: Rf 0.33 (chloroform:methanol=9:1)

Example 81

1-Naphthylmethyloxycarbonyl-Asn-(2S,3S)-AHPBA-Pro-NH-tBu

[Process 1] 1-Naphthylmethyl 4-nitrophenyl carbonate

In 5 ml of pyridine containing 1.0 g of 1-naphthylmethanol, 1.27 g of 4-nitrophenyl chloroformate was added under ice cooling and the resultant mixture was stirred for 3 hr. Purified water and ethyl acetate, each 20 ml, were added to the reaction mixture and the ethyl acetate layer was separated and washed with purified water. The ethyl acetate layer was dried over anhydrous sodium sulfate, evaporated under reduced pressure and crystallized by the addition of ethanol to give 1.08 g of the title compound.

TLC: Rf 0.81 (chloroform)

[Process 2] 1-Naphthylmethyloxycarbonyl-Asn-(2S,3S)-AHPBA-Pro-NH-tBu

Deprotection of 30 mg of the compound obtained by Example 80 was performed similarly to that in Example 28 (Process 3), and the obtained product was dissolved in 3 ml of DMF and neutralized with 8 µl of triethylamine under ice cooling. To the neutralized solution, 35 mg of 1-naphthylmethyl 4-nitrophenyl carbonate 12 µl of N-methylmorpholine were added and the resultant solution was stirred for 14 hr. The reaction mixture was treated similarly to that in Example 49 to give 5 mg of the title compound.

TLC: Rf 0.40 (chloroform:methanol=9:1)

FAB-MS: 646 (M+1)

Example 82

Benzyloxycarbonyl-Asn-(2S,3S)-AHPBA-Thz-NH-tBu

[Process 1] Boc-Thz-NH-tBu

In a DMF solution containing 0.10 g of N-(t-butoxycarbonyl)-1,3-thiazolidine-4-carboxylic acid, 45 µl of tert-butylamine, 66 mg of HOBt and 98 mg of EDC hydrochloride were added under ice cooling and the resultant mixture was stirred for 14 hr. The reaction mixture was treated similarly to that in Example 34 (Process 3) to give 90 mg of the title compound.

TLC: Rf 0.43 (chloroform:methanol=20:1)

[Process 2] Boc-(2S,3S)-AHPBA-Thz-NH-tBu

Deprotection of 50 mg of the compound obtained by the process 1 in the presence of 25 µl of anisole and 14 µl of 1,2-ethanedithiol was performed similarly to that in Example 28 (Process 3), and the obtained product was dissolved in 5 ml of DMF and neutralized with 24 µl of triethylamine under ice cooling. To the neutralized solution, 51 mg of Boc-(2S,3S)-AHPBA-OH, 77 mg of Bop reagent, 48 µl of triethylamine were added and the resultant mixture was stirred for 2 hr. The reaction mixture was treated similarly to that in Example 28 (Process 3) and crystallized from hexane to give 51 mg of the title compound.

TLC: Rf 0.64 (chloroform:methanol=9:1)

[Process 3] Benzyloxycarbonyl-Asn-(2S,3S)-AHPBA-Thz-NH-tBu

Deprotection of 51 mg of the compound obtained by the process 2 in the presence of 25 µl of anisole and 10 µl of ethanedithiol was performed similarly to that in Example 28 (Process 3), and the obtained product was dissolved in 5 ml of DMF and neutralized with 15 µl of triethylamine under ice cooling. To the neutralized solution, 85 mg of benzyloxycarbonyl-Asn-ONp, 34 mg of HOBt and 24 µl of N-methylmorpholine were added and the resultant solution was stirred for 14 hr. The reaction mixture was treated similarly to that in Example 49 to give 20 mg of benzyloxycarbonyl-Asn-(2S,3S)-AHPBA-Thz-NH-tBu. In methanol, seven mg of the obtained crystals were dissolved, fractionated by a reversed-phase HFLC and lyophilized to give four mg of the title compound.

Analytical HPLC: 21.37 min (For the condition, see: Example 35).

FAB-MS: 614 (M+1)

$^1$H NMR (CDCl$_3$, 500 MHz): FIG. 1

Example 83

Benzyloxycarbonyl-Asn-(2S,3S)-AHPBA-Pro-NH—CH$_2$—C(CH$_3$)$_3$

[Process 1] Boc-Pro-NH—CH$_2$—C(CH$_3$)$_3$

In a DMF solution containing 1.00 g of Boc-Pro-OH, 0.58 ml of neopentylamine, 0.71 g of HOBt and 1.06 g of EDC hydrochloride were added and the resultant mixture was stirred for 14 hr. The reaction mixture was treated similarly to that in Example 30 (Process 3) to give 605 mg of the title compound.

TLC: Rf 0.56 (chloroform:methanol=20:1)

[Process 2] Benzyloxycarbonyl-Asn-(2S,3S)-AHPBA-Pro-NH—CH$_2$—C(CH$_3$)$_3$

The title compound was obtained according to the method of Example 55 from the protected amino acid obtained in the above process 1.

Analytical HPLC: 21.24 min (For the condition, see: Example 35)

FAB-MS: 610 (M+1)

Example 84

Benzyloxycarbonyl-Asn-(2S,3S)-AHPBA-Pro-NH—C$_6$H$_{11}$

[Process 1] Boc-Pro-NH—C$_6$H$_{11}$

In a DMF solution containing 1.00 g of Boc-Pro-OH, 0.53 ml of cyclohexylamine, 0.63 g of HOBt and 1.07 g of EDC hydrochloride were added under ice cooling and the resultant mixture was stirred for 14 hr. The reaction mixture was treated similarly to that in Example 30 (Process 3) to give 853 mg of the title compound.

TLC: Rf 0.77 (chloroform:methanol=20:1)

[Process 2] Benzyloxycarbonyl-Asn-(2S,3S)-AHPBA-Pro-NH—C$_6$H$_{11}$

The title compound was obtained according to the method of Example 55 from the protected amino acid obtained in the above process 1.

TLC: Rf 0.44 (chloroform:methanol=9:1)

FAB-MS: 622 (M+1)

Example 85

Benzyloxycarbonyl-Asn-(2S,3S)-AHPBA-Pro-NH—CH(CH$_3$)$_2$

[Process 1] Boc-Pro-NH—CH(CH$_3$)$_2$

In a DMF solution containing 1.00 g of Boc-Pro-OH, 0.40 ml of isopropylamine, 0.71 g of HOBt and 1.06 g of EDC hydrochloride were added under ice cooling and the resultant mixture was stirred for 14 hr. The reaction mixture was treated similarly to that in Example 28 (Process 2) to give 654 mg of the title compound.

TLC: Rf 0.41 (chloroform:methanol=20:1)

[Process 2] Benzyloxycarbonyl-Asn-(2S,3S)-AHPBA-Pro-NH—CH(CH$_3$)$_2$

The title compound was obtained according to the method of Example 55 from the protected amino acid obtained in the above process 1.

Analytical HPLC: 17.57 min (For the condition, see: Example 35)

FAB-MS: 582 (M+1)

Example 86

Benzyloxycarbonyl-Asn-(2S,3S)-AHPBA-Pro-O-tBu

[Process 1] Benzyloxycarbonyl-Asn-(2S,3S)-AHPBA-O-benzyl

Deprotection of 190 mg of Boc-(2S,3S)-AHPBA-O-benzyl obtained by Example 16 (Process 1) was performed similarly to that in Example 28 (Process 3), and the obtained product was dissolved in 3 ml of DMF and neutralized with 69 μl of triethylamine under ice cooling. To the neutralized solution, 286 mg of benzyloxycarbonyl-Asn-ONp, 113 mg of HOBt and 81 μl N-methylmorpholine were added and the resultant mixture was stirred for 14 hr. The reaction mixture was evaporated under reduced pressure and the resultant residue was mixed with purified water and the formed precipitates were collected and washed thoroughly with purified water. The precipitates were recovered and reprecipitated from DMF-ether to give 240 mg of the title compound.

TLC: Rf 0.60 (chloroform:methanol:water=8:3:1, lower layer)

[Process 2] Benzyloxycarbonyl-Asn-(2S,3S)-AHPBA-OH

In 3 ml of DMF, 230 mg of the peptide obtained by the process 1 was dissolved and stirred with 0.52 ml of 1N-NaOH under ice cooling for 2 hr. The reaction mixture was neutralized with citric acid and evaporated under reduced pressure. To the resultant residue, 5% citric acid aqueous solution was added to cause precipitation and the precipitates were reprecipitated from DMF and ether to give 140 mg of the title compound.

TLC: Rf 0.59 (n-BuOH:acetic acid:pyridine:water=4:1:1:2)

[Process 3] Benzloxycarbonyl-Asn-(2S,3S)-AHPBA-Pro-O-tBu

In 2 ml of DMF, 19 mg of H-Pro-O-tBu hydrochloride was dissolved and neutralized with 13 μl of triethylamine under ice cooling. To the neutralized solution, 20 mg of benzyloxycarbonyl-Asn-(2S,3S)-AHPBA-OH, 20 mg of Bop reagent and 25 μl of triethylamine were added and the resultant mixture was stirred for 2 hr. The reaction mixture was treated similarly to that in Example 49, except for the crystallization solvent (hexane), to give 22 mg of the title compound.

TLC: Rf 0.48 (chloroform:methanol=9:1)

FAB-MS: 597 (M+1)

Figure 2:
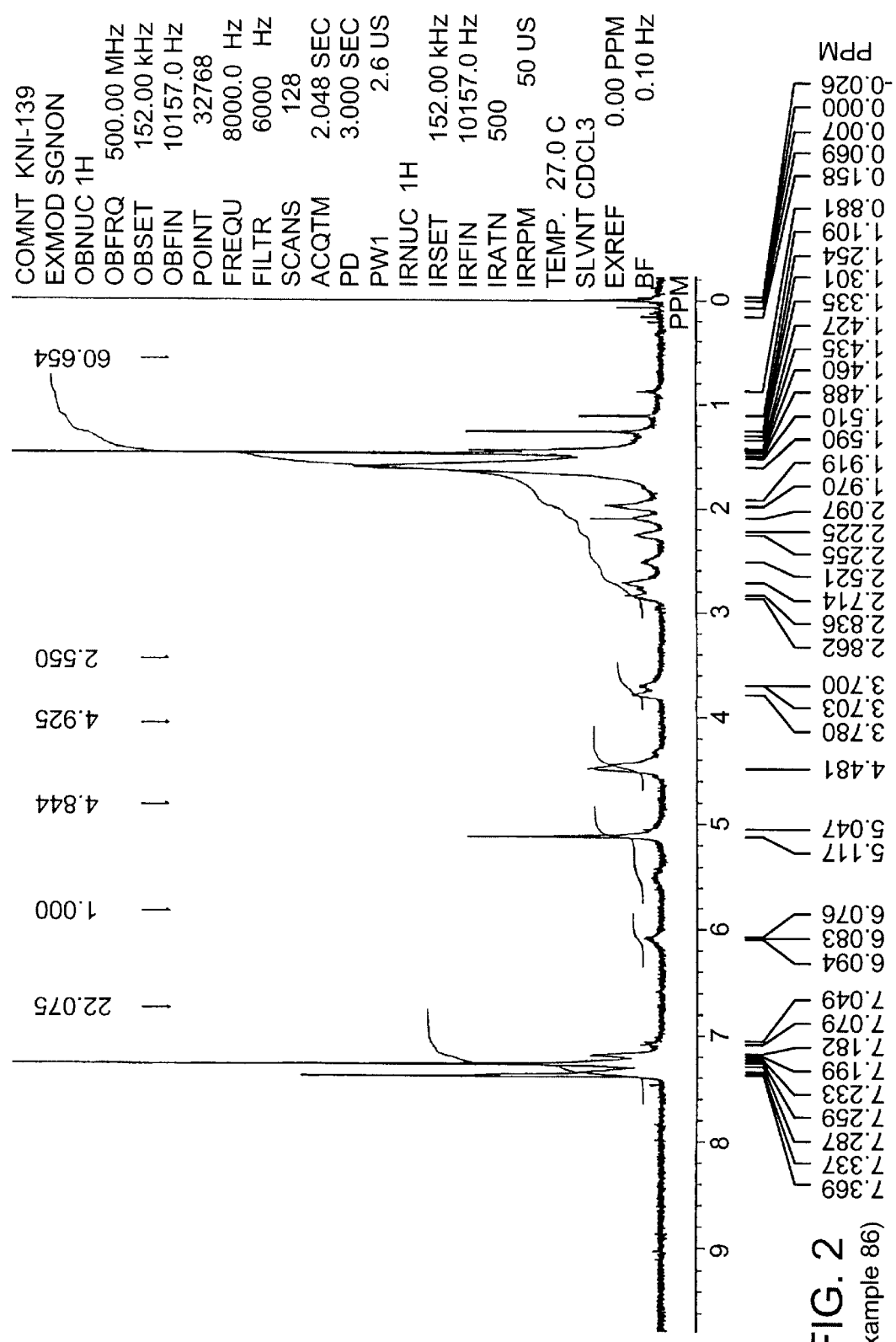

$^1$H NMR (CDCl$_3$, 500 MHz): FIG. 2

Example 87

Benzyloxycarbonyl-Asn-(2S,3S)-AHPBA-Pro-NH-tAmyl

[Process 1] Boc-Pro-NH-tAmyl

In a DMF solution containing 0.50 g of Boc-Pro-OH, 0.27 ml of tert-amylamine, 0.36 g of HOBt and 0.53 g of EDC hydrochloride were added under ice cooling and the resultant mixture was stirred for 14 hr. The reaction mixture treated similarly to that in Example 28 (Process 2) to give 448 mg of the title compound.

TLC: Rf 0.56 (chloroform:methanol=20:1)

[Process 2] Benzyloxycarbonyl-Asn-(2S,3S)-AHPBA-Pro-NH-tAmyl

Deprotection of 20 mg of the compound obtained by the process 1 was performed similarly to that in Example 28 (Process 3), and the obtained product was dissolved in 3 ml of DMF and neutralized with 10 μl of triethylamine under ice cooling. To the neutralized solution, 31 mg of benzyloxycarbonyl-Asn-(2S,3S)-AHPBA-OH, 31 mg of Bop reagent, 20 μl of triethylamine were added and the resultant mixture was stirred for 2 hr. The reaction mixture was treated similarly to that in Example 55 (Process 3) to give 33 mg of the title compound.

Analytical HPLC: 21.98 min (For the condition, see: Example 35.)

FAB-MS: 610 (M+1)

Example 88

Benzyloxycarbonyl-Asn-(2S,3S)-AHPBA-Pro-NH-cycloropyl

[Process 1] Boc-Pro-NH-cycloropyl

In a DMF solution containing 0.50 g of Boc-Pro-OH, 0.16 ml of cyclopropylamine, 0.36 g of HOBt and 0.53 g of EDC hydrochloride were added under ice cooling and the resultant mixture was stirred for 14 hr. The reaction mixture was treated similarly to that in Example 30 (Process 3) to give 245 mg of the title compound.

TLC: Rf 0.47 (chloroform:methanol=20:1)

[Process 2] Benzyloxycarbonyl-Asn-(2S,3S)-AHPBA-Pro-NH-cyclopropyl

The title compound was obtained according to the method of Example 87 from the protected amino acid obtained in the above process 1.

TLC: Rf 0.60 (chloroform:methanol:water=8:3:1, lower layer)

FAB-MS: 580 (M+1)

Example 89

Benzyloxycarbonyl-Asn-(2S,3S)-AHPBA-Pro-NH—CH(C$_2$H$_5$)$_2$

[Process 1] Boc-Pro-NH—CH(C$_2$H$_5$)$_2$

In a DMF solution containing 0.50 g of Boc-Pro-OH, 0.27 ml of 1-ethylpropylamine, 0.36 g of HOBT and 0.53 g of EDC hydrochloride were added under ice cooling and the resultant mixture was stirred for 14 hr. The reaction mixture was treated similarly to that in Example 30 (Process 3) to give 324 mg of the title compound.

TLC: If 0.57 (chloroform:methanol=20:1)

[Process 2] Benzyloxycarbonyl-Asn-(2S,3S)-AHPBA-Pro-NH—CH(C$_2$H$_5$)$_2$

The title compound was obtained according to the method of Example 87 from the protected amino acid obtained in the above process 1.

TLC: Rf 0.48 (chloroform:methanol=9:1)
FAB-MS: 610 (M+1)

Example 90

1-Naphthylmethyloxycarbonyl-Msa-(2S,3S)-AHPBA-Pro-NH-tBu

[Process 1] Boc-Msa-(2S,3S)-AHPBA-Pro-NH-tBu

Deprotection of 30 mg of the compound obtained by Example 55 (Process 2) was performed similarly to that in Example 28 (Process 3), and the obtained product was dissolved in 3 ml of DMF and neutralized with 10 µl of triethylamine under ice cooling. To the neutralized solution, 18 mg of Boc-Msa-OH, 30 mg of Bop reagent and 19 µl of triethylamine were added and the resultant mixture was stirred for 2 hr. The reaction mixture was treated similarly to that in Example 86 (Process 3) to give 27 mg of the title compound.

TLC: Rf 0.52 (chloroform:methanol=9:1)

[Process 2] 1-Naphthylmethyloxycarbonyl-Msa-(2S, 3S)-AHPBA-Pro-NH-tBu

The title compound was obtained according to the method of Example 81 from the protected peptide obtained the above process 1.

TLC: Rf 0.50 (chloroform:methanol=9:1)
FAB-MS: 681 (M+1)

Example 91

1-Naphthyloxyacetyl-Asn-(2S,3S)-AHPBA-Pro-NH-tBu

Deprotection of 22 mg of the compound obtained by Example 80 was performed similarly to that in Example 28 (Process 3), and the obtained product was dissolved in 3 ml of DMF and neutralized with 5.4 µl of triethylamine under ice cooling. To the neutralized solution, 8 mg of 1-naphthoxyacetic acid, 17 mg of Bop reagent and 11 µl of triethylamine were added and the resultant mixture was stirred for 2 hr. The reaction mixture was treated similarly to that in Example 50 (Process 2) to give 23 mg of the crude title compound. In methanol, 8 m of the obtained crystals were dissolved, fractionated by a reversed-phase HPLC and lyophilized to give 4 mg of the title compound. Analytical HPLC: 23.14 min (For the condition, see: Example 35.)

FAB-MS: 646 (M+1)

Example 92

FMOC-Asn-2S,3S)-AHPBA-Pro-NH-tBu

Deprotection of 30 mg of the compound obtained by Example 55 (Process 2) was performed similarly to that in Example 28 (Process 3), and the obtained product was dissolved in 3 ml of DMF and neutralized with 9.3 µl of triethylamine under ice cooling. To the neutralized solution, 70 mg of Fmoc-Asn-O-pentafluorophenyl, 21 mg of HOBt and 15 a 1 of N-methylmorpholine were added and the resultant mixture was stirred for 14 hr. The reaction mixture was treated similarly to that in Example 50 (Process 2) to give 85 mg of the crude product. In methanol, 12 mg of the crude product was dissolved, fractionated by a reversed-phase HPLC and lyophilizated to give 4.8 mg of the title compound.

TLC: Rf 0.36 (chloroform:methanol=9:1)
FAB-MS: 684 (M+1)

Example 93

Benzyloxycarbonyl-Asn-(2S,3S)-AHPBA-Pro-Aib-NH$_2$

[Process 1] Boc-Aib-NH$_2$

In a DMF solution containing 1.00 g of 2-N-(tert-butoxycarbonyl)aminoisobutyric acid, 0.75 ml of triethylamine and 0.70 ml of isobutyl chloroformate were added at −10 to −20° C. and the resultant mixture was stirred for 10 min. To the solution, 1.03 ml of concentrated ammonia water (28%) was added and the resultant mixture was stirred for 2 hr. The reaction mixture was evaporated under reduced pressure and water was added to the residue. The formed precipitates were thoroughly washed with purified water and reprecipitated from THF-ether to give 200 mg of the title compound.

TLC: Rf 0.63 (chloroform:methanol:water=8:3:1, lower layer)

[Process 2] Boc-Pro-Aib-NH$_2$

Deprotection of 100 mg of the compound obtained by the process 1 was performed similarly to that in Example 28 (Process 3), and the obtained product was dissolved in 3 ml of DMF and neutralized with 68 µl of triethylamine under ice cooling. To the neutralized solution, 107 mg of Boc-Pro-OH, 237 mg of Bop reagent and 137 µl of triethylamine were added and the resultant mixture was stirred for 2 hr. The reaction mixture was treated similarly to that in Example 86 (Process 3) to give 35 mg of the title compound.

TLC: Rf 0.48 (chloroform:methanol=9:1)

[Process 3] Boc-(2S,3S)-AHPBA-Pro-Aib-NH$_2$

Deprotection of 35 mg of the compound obtained by the process 2 was performed similarly to that in Example 28 (Process 3), and the obtained product was dissolved in 5 ml of DMF and neutralized with 17 µl of triethylamine under ice cooling. To the neutralized solution, 35 mg of Boc-(2S,3S)-AHPBA-OH, 53 mg of Bop reagent, and 33 µl of triethylamine were added and the resultant mixture was stirred for 2 hr. The reaction mixture was treated similarly to that in Example 46, except for the chromatography solvent (chloroform:methanol'10:1), to give 36 mg of the title compound.

TLC: Rf 0.28 (chloroform:methanol=9:1)

[Process 4] Benzyloxycarbonyl-Asn-(2S,3S)-AHPBA-Pro-Aib-NH$_2$

Deprotection of 35 mg of the compound obtained by the process 3 was performed similarly to that in Example 28 (Process 3), and the obtained product was dissolved in 3 ml of DMF and neutralized with 10 µl of triethylamine under ice cooling. To the neutralized solution, 57 mg of benzyloxycarbonyl-Asn-ONp, 23 mg of HOBt and 16 µl of N-methylmorpholine were added and the resultant mixture was stirred for 14 hr. The reaction mixture was treated similarly to that in Example 55 (Process 3) to give the crude product. The crude product dissolved in methanol, fractionted by a reversed-phase HpLC and lyophilized to give 5.3 mg of the title compound.

TLC: Rf 0.63 (chloroform:methanol:water=8:3:1, lower layer)

FAB-MS: 625 (M+1)

Example 94

Bis(4-chlorophenyl)methyloxyacetyl-Asn-(2S,3S)-AHPBA-Pro-NH-tBu

Deprotection of 25 mg of the compound obtained by Example 80 (Process 2) was performed similarly to that in Example 28 (Process 3), and the obtained product was dissolved in 3 ml of DMIF and neutralized with 6.0 µl of triethylamine under ice cooling. To the neutralized solution, 26 mg of bis(4-chlorophenyl)methyloxyacetic acid, 24 mg of Bop reagent, and 6 µl of N-methylmorpholine were added and the resultant mixture was stirred for 2 hr. The reaction mixture was treated similarly to that in Example 50 (Process 2) and the formed precipitates were dissolved in methanol. The methanol solution was fractionated by a reversed-phase HPLC and lyophilized to give the title compound.

Analytical HPLC: 29.97 min (For the condition, see: Example 35).

FAB-MS: 755 (M+1)

Example 95

Benzyloxycarbonyl-Asn-(2S,3S)-AHPBA-Hyp(Bzl)-NH-tBu

[Process 1] Boc-Hyp(Bzl)-NH-tBu

In a DMF solution containing 100 mg of Boc-Hyp(Bzl)-OH, 33 µl of t-butylamine, 48 mg of HOBt and 71 mg of EDC hydrochloride were added and the resultant mixture was stirred for 14 hr. The reaction mixture was treated similarly to that in Example 33 (Process3) to give 88 mg of the title compound.

[Process 2] Boc-(2S,3S)-AHPBA-Hyp(Bzl)-NH-tBu

Deprotection of 76 mg of the compound obtained by the process 1 was performed similarly to that in Example 28 (Process 3), and the obtained product was dissolved in 5 ml of DMF and neutralized with 28 µl of triethylamine under ice cooling. To the neutralized solution, 60 mg of Boc-(2S, 3S)-AHPBA-OH, 89 mg of Bop reagent and 56 µl of triethylamine were added and the resultant mixture was stirred for 2 hr. The reaction mixture was treated similarly to that in Example 28 (Process 3) to give 92 mg of the title compound.

[Process 3] Benzyloxycarbonyl-Asn-(2S,3S)-AHPBA-Hyp(Bzl)-NH-tBu

Deprotection of 30 mg of the compound obtained by the process 2 was performed similarly to that in Example 28 (Process 3), and the obtained product was dissolved in 4 ml of DMF and neutralized with 6.4 µl of triethylamine under ice cooling. To the neutralized solution, 36 mg of benzyloxycarbonyl-Asn-ONp, 14 mg of HOBt and 10 µl of N-methylmorpholine were added and the resultant mixture was stirred for 14 hr. The reaction mixture was treated similarly to that in Example 49 to give 23 mg of the title compound.

TLC: Rf 0.41 (chloroform:methanol=9:1)

Analytical HPLC: 26.65 min (For the condition, see: Example 35.)

FAB-MS: 702 (M+1)

Example 96

Benzyloxycarbonyl-Asn-(2S,3S)-AHPBA-Inc-NH-tBu

[Process 1] Boc-Inc-NH-tBu

In a DMF solution containing 500 mg of Boc-Inc-OH, 200 µl of t-butylamine, 291 mg of HOBt and 435 mg of EDC hydrochloride were added and the resultant mixture was stirred for 14 hr under ice cooling. The reaction mixture was treated similarly to that in Example 33 (Process 3) to give the title compound.

[Process 2] Benzyloxycarbonyl-Asn-(2S,3S)-AHPBA-Inc-NH-tBu

Deprotection of 20 mg of the compound obtained by the process 1 was performed similarly to that in Example 28 (Process 3) in the presence of 10 µl of anisole and 26 µl of 1,2-ethanedithiol, and the obtained product was dissolved in 3 ml of DMF and neutralized with 7 µl of triethylamine under ice cooling. To the neutralized solution, 22 mg of Benzyloxycarbonyl-Asn-(2S,3S)-AHPBA-OH, 22 mg of Bop reagent and 11 µl of triethylamine were added and the resultant mixture was stirred for 2 hr. The reaction mixture was treated similarly to that in Example 50 (Process 2) subjected to a reversed-phase HPLC to give 335 mg of the title compound.

Analytical HPLC: 22.88 min (For the condition, see: Example 35.)

FAB-MS: 644 (M+1)

Example 97

Boc-Sma-(2S,3S)-AHPBA-Pro-NH-tBu

Deprotection of 30 mg of the compound obtained by Example 55 (Process 2) was performed similarly to that in Example 28 (Process 3), and the obtained product was dissolved in 3 ml of dichloromethane. To the dichloromethane solution, 30 mg of Boc-Sma-OH.DCHA and 435 mg of EDC hydrochloride were added under ice cooling and the mixture was stirred overnight. The reaction mixture was treated similarly to that in Example 50 (Process2) to give 7 mg of the title compound.

TLC: Rf 0.61 (chloroform:methanol:$H_2O$=8:3:1)

Example 98

1-Napthoxyacetyl-Sma-(2S,3S)-AHPBA-Pro-NH-tBu

Deprotection of 7 mg of the compound obtained by Example 97 was performed similarly to that in Example 28 (Process 3), and the obtained product was dissolved in 2 ml of DMF and neutralized with 1.6 µl of triethylamine under ice cooling. To the neutralized solution, 2.4 mg of 1-naphthoxyacetic acid, 5.2 mg of Bop reagent and 3.2 µl of triethylamine were added and the resultant mixture was stirred for 2 hr. The reaction mixture was treated similarly to that in Example 51 (Process2), and the crude product was dissolved in methanol and subjected to a reversed-phase HPLC (water-acetonitrile system) and fractionated, purified and lyophilized to give 0.83 mg of the title compound.

Analytical HPLC: 25.08 min (For the condition, see: Example 35.)

FAB-MS: 682 (M+1)

Example 99

Benzyloxycarbonyl-Asn-(2S,3S)-AHPBA-Pro-NH—C(CH$_3$)$_2$—CH$_2$OH

[Process 1] Boc-Pro-NH—C(CH$_3$)$_2$—CH$_2$OH

In a DMF solution containing 0.20 g of Boc-Pro-OH, 0.09 ml of 2-amino-2-methyl-1-propanol, 0.14 g of HOBt and 0.21 g of EDC hydrochloride were added and the resultant mixture was stirred for 14 hrs. The reaction mixture was treated similarly to that in Example 46 to give 80 mg of the title compound.

TLC: Rf 0.32 (chloroform:methanol=20:1)

[Process 2] Boc-(2S,3S)-AHPBA-Pro-NH—C(CH$_3$)$_2$—CH$_2$OH

Deprotection of 50 mg of the compound obtained by the process 1 was performed similarly to that in Example 28 (Process 3), and the obtained product was dissolved in 5 ml of DMF and neutralized with 24 μl of triethylamine under ice cooling. To the neutralized solution, 52 mg of Boc-(2S,3S)-AHPBA-OH, 77 mg of Bop reagent and 48 μl of triethylamine were added and the resultant mixture was stirred for 2 hr. The reaction mixture was treated similarly to that in Example 55 (Process 2) to give 54 mg of the title compound.

TLC: Rf 0.53 (chloroform:methanol=9:1)

[Process 3] Benzyloxycarbonyl-Asn-(2S,3S)-AHPBA-Pro-NH—C(CH$_3$)$_2$—CH$_2$OH

Deprotection of 30 mg of the compound obtained by the process 2 was performed similarly to that in Example 28 (Process 3), and the obtained product was dissolved in 3 ml of DMF and neutralized with 9 μl of triethylamine under ice cooling. To the neutralized solution, 50 mg of benzyloxycarbonyl-Asn-ONp, 20 mg of HOBt and 14 μl of N-methylmorpholine were added and the resultant mixture was stirred for 14 hr. The reaction mixture was treated similarly to that in Example 49 to give 6.6 mg of the title compound.

Analytical HPLC: 16.37 min (For the condition, see: Example 35.)

FAB-MS: 612 (M+1)

Example 100

1-Naphthoxyacetyl-Msa-(2S,3S)-AHPBA-Thz-NH-tBu

[Process 1] Boc-Msa-(2S,3S)-AHPBA-Thz-NH-tBu

Deprotection of 65 mg of the compound obtained by Example 82 (Process 2) was performed similarly to that in Example 28 (Process 3), and the obtained product was dissolved in 3 ml of DMF and neutralized with 20 μl of triethylamine under ice cooling. To the neutralized solution, 38 mg of Boc-methanesulfonylalanine, 62 mg of Bop reagent and 40 μl of triethylamine were added and the resultant mixture was stirred for 2 hr. The reaction mixture was treated similarly to that in Example 55 (Process 2) to give 34 mg of the title compound.

TLC: Rf 0.53 (chloroform:methanol=9:1)

[Process 2] 1-Naphthoxyacetyl-Msa-(2S,3)-AHFBA-Thz-NH-tBu

Deprotection of 34 mg of the compound obtained by the process 1 was performed similarly to that in Example 28 (Process 3), and the obtained product was dissolved in 5 ml of DMF and neutralized with 8.0 μl of triethylamine under ice cooling. To the neutralized solution, 12 mg of 1-naphthoxyacetic acid, 25 mg of Bop reagent and 16 μl of triethylamine were added and the resultant mixture was stirred for 2 hr. The reaction mixture was treated similarly to that in Example 46 and ether was added to give 26 mg of the crude above mentioned compound. In methanol, 5 mg of the crude solid was dissolved, fractionated by a reversed-phase HPLC and lyophilized to give 1.4 mg of the title compound.

Analytical HPLC: 27.08 min (For the condition, see: Example 35.)

FAB-MS: 699 (M+1)

Figure 3:
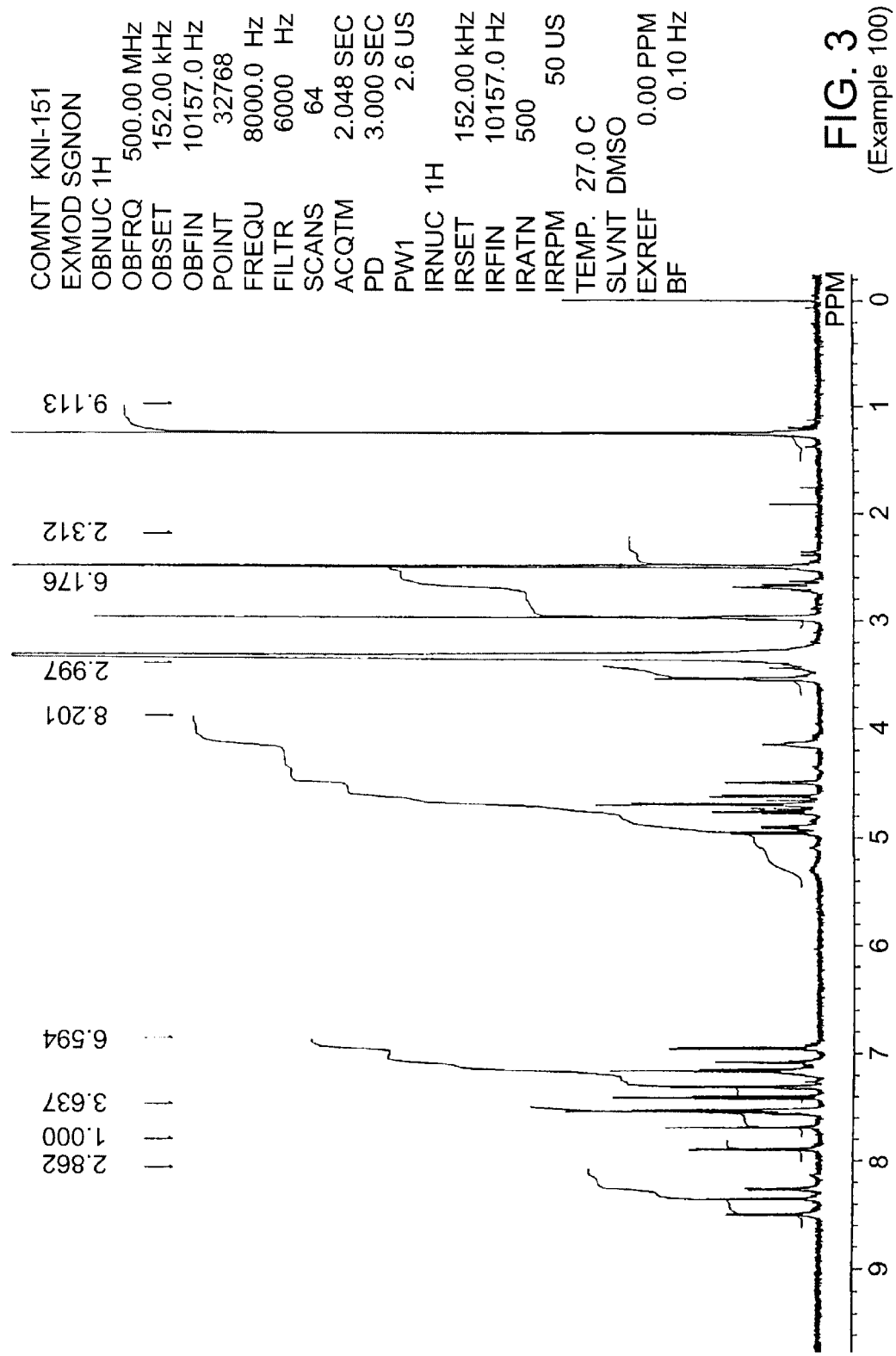

$^1$H NMR (DMSO-d$_6$, 500 MHz): FIG. 3

Example 101

1-Naphthoxyacetyl-Asn-(2S,3S)-AHPBA-Thz-NH-tBu

[Process 1] Boc-Asn-(2S,3S)-AHPBA-Thz-NH-tBu

Deprotection of 28 mg of the compound obtained by Example 82 (Process 2) was performed similarly to that in Example 28 (Process 3), and the obtained product was dissolved in 3 ml of DMF and neutralized with 8 μl of triethylamine under ice cooling. To the neutralized solution, 40 mg of Boc-Asn-ONp, 8 mg of HOBt and 12 μl of N-methylmorpholine were added and the resultant mixture was stirred for 14 hr. The reaction mixture was treated similarly to that in Example 93 (Process 3) to give 28 mg of the title compound.

[Process 2] 1-Naphthoxyacetyl-Asn-(2S,3S)-AHPBA-Thz-NH-tBu

Deprotection of 28 mg of the compound obtained by the process 1 was performed similarly to that in Example 28 (Process 3), and the obtained product was dissolved in 5 ml of DMF and neutralized with 6.5 μl of triethylamine under ice cooling. To the neutralized solution, 9.5 mg of 1-naphthoxyacetic acid, 21 mg of Bop reagent and 13 μl of triethylamine were added and the resultant mixture was stirred for 2 hr. The reaction mixture was treated similarly to that in Example 46 and ether was added to give the crude above mentioned compound. The crude solid was dissolved in methanol, subjected to a reversed-phase HPLC (water-acetonitrile system) and fractionated, purified and lyophilized to give 5.8 mg of the title compound.

Analytical HPLC: 24.38 min (For the condition, see: Example 35.)

FAB-MS: 664 (M+1)

Example 102–103

Benzyloxycarbornyl-Asn-(2S,3S)-AHPBA-(DL)Tic-NH-tBu

[Process 1] Boc-(DL)-Tic-NH-tBu

In a DMF solution containing 200 mg g of N-(tert-butoxycarbonyl)-(DL)-1,2,3,4-tetrahydroisoquinoline-3- carboxylic acid, 76 μl of tert-butylamine, 110 mg of HOBt and 165 mg of EDC hydrochloride were added and the resultant mixture was stirred for 14 hr. The reaction mixture was treated similarly to that in Example 28 (Process 2) to give 150 mg of the title compound.

TLC: Rf 0.80 (chloroform:methanol=20:1)

[Process 2] Boc-(2S,3S)-AHPBA-(DL)-Tic-NH-tBu

Deprotection of 60 mg of the compound obtained by the process 1 was performed similarly to that in Example 28 (Process 3), and the obtained product was dissolved in 5 ml of DMF and neutralized with 25 μl of triethylamine under ice cooling. To the neutralized solution, 53 mg of Boc-(2S, 3S)-AHPBA-OH, 80 mg of Bop reagent and 50 μl of triethylamine were added and the resultan mixture was stirred for 2 hr. The reaction mixture was treated similarly to that in Example 28 (Process 3) to give 81 mg of the title compound.

TLC: Rf 0.59 (chloroform:methanol=9:1)

[Process 3] Benzyloxycarbonyl-Asn-(2S,3S)-AHPBA-(DL)Tic-NH-tBu

Deprotection of 81 mg of the compound obtained by the process 2 was performed similarly to that in Example 28 (Process 3), and the obtained product was dissolved in 8 ml of DMF and neutralized with 22 μl of triethylamine under ice cooling. To the neutralized solution, 124 mg of benzyloxycarbonyl-Asn-ONp, 24 mg of HOBt and 35 μl of N-methylmorpholine were added and the resultant mixture was stirred for 14 hr. The reaction mixture was treated similarly to that in Example 46 and crystallized by the addition of ether to give 44 mg of the crude title compound. In methanol, 10 mg of the crude solid was dissolved, fractionated by a reversed-phase HPLC and lyophilized to give the title compound.

Analytical HPLC: 24.44 and 25.16 min (For the condition, see: Example 35.)

FAB-MS: 658 (M+1)

Example 104

Benzyloxycarbonyl-Asn-(2S,3S)-AHPBA-Dtc-NH-tBu

[Process 1] Boc-Dtc-NH-tBu

In a methylene chloride solution containing 3.0 g of Boc-Dtc-OH, 1.45 ml of triethylamine, 2.89 g of 2-chloro-1,3-dimethylimidazolinium hexafluorophosphate and 3.28 ml of tert-butylamine were added, and the resultant mixture was stirred for 14 hr. The resultant solution was treated similarly to that in Example 33 (Process 3) to give 2.49 g of the title compound as a mixture of cisoide and transoid.

TLC: Rf 0 4 0.24 (chloroform:methanol=40:1)

[Process 2] Boc-(2S,3S)-AHFBA-Dtc-NH-tBu

Deprotection of 2.49 g of the compound obtained by the process 1 was performed similarly to that in Example 28 (Process 3), and the obtained product was dissolved in 60 ml of methylene chloride and neutralized with 1.10 ml of triethylamine under ice cooling. To the neutralized solution, 3.75 g of Boc-(2S,3S)-AHPBA-OH.DCHA salt, 3.48 g of Bop reagent and 1.10 ml of triethylamine were added and the resultant mixture was stirred overnight. Further, 1.74 g of Bop reagent and 1.10 ml of triethylamine were added and the resultant mixture was stirred overnight. The reaction mixture was treated similarly to that in Example 33 (Process 3) to give 2.81 g of the title compound.

TLC: Rf 0.66, 0.73 (chloroform:methanol=9:1)

[Process 3] Benzyloxycarbonyl-Asn-(2S,3S)-AHPBA-Dtc-NH-tBu

Deprotection of 53 mg of the compound obtained by the process 2 was performed similarly to that in Example 28 (Process 3), and the obtained product was dissolved in 5 ml of DMF and neutralized with 15 μl of triethylamine under ice cooling. To the neutralized solution, 83 mg of benzyloxycarbonyl-Asn-ONp, 17 mg of HOBT and 24 μl of N-methylmorpholine were added and the resultant mixture was stirred for 14 hr. The reaction mixture was treated similarly to that in Example 46 and crystallized by the addition of ether to give 27 mg of the crude title CoMpound. The crude solid was dissolved in methanol, fractionated by a reversed-phase HPLC and lyophilized to give 10.6 mg of the title compound.

Analytical HPLC: 23.80 min (For the condition, see: Example 35.)

FAB-MS: 642 (M+1)

Example 105

1-Naphthoxyacetyl-Msa-(2S,3S)-AHPBA-Dtc-NH-tBu

[Process 1] Boc-Msa-(2S,3S)-AHPBA-Dtc-NH-tBu

Deprotection of 69 mg of the compound obtained by Example 104 (Process 2) was performed similarly to that in Example 28 (Process 3), and the obtained product was dissolved in 3 ml of DMF and neutralized with 20 μl of triethylamine under ice cooling. To the neutralized solution, 38 mg of Boc-methanesulfonylalanine, 62 mg of Bop reagent and 40 μl of triethylamine were added and the resultant mixture was stirred for 2 hr. The reaction mixture was treated similarly to that in Example 55 (Process 2) to give 55 mg of the title compound.

TLC: Rf 0.62 (chloroform:methanol=9:1)

[Process 2] 1-Naphthoxyacetyl-Msa-(2S,3S)-AHPBA-Dtc-NH-tBu

Deprotection of 55 mg of the compound obtained by the process 1 was performed similarly to that in Example 28 (Process 3), and the obtained product was dissolved in 5 ml of DMF and neutralized with 12 μl of triethylamine under ice cooling. To the neutralized solution, 18 mg of 1-naphthoxyacetic acid, 38 mg of Bop reagent, and 24 μl of triethylamine were added and the resultant mixture was stirred for 2 hr. The reaction mixture was treated similarly to that in Example 46, except for the chromatography solvent (chloroform:methanol=15:1), to give 37 mg of the crude title compound. In methanol, 14 mg of the crude solid was dissolved, fractionated by a reversed-phase HPLC and lyophilized to give 6.5 mg of the title compound.

Analytical HPLC: 29.40 min (For the condition, see: Example 35.)

FAB-MS: 727 (M+1)

Example 106

1-Naphthoxyacetyl-Asn-(2S,3S)-AHPBA-Dtc-NH-tBu

[Process 1] Boc-Asn-(2S,3S)-AHPBA-Dtc-NH-tBu

Deprotection of 2.81 g of the compound obtained by Example 104 (Process 2) was performed similarly to that in Example 28 (Process 3), and the obtained product was dissolved in 50 ml of DMF and neutralized with 0.79 ml of triethylamine under ice cooling. To the neutralized solution, 3.02 g of Boc-Asn-ONp, 1.31 g of HOBt and 0.94 ml of N-methylmorpholine were added and the resultant mixture was stirred for 14 hr. The reaction mixture was evaporated under reduced pressure and the residue was mixed with 5% sodium hydrogencarbonate aqueous solution to give precipitates. The precipitates were filtered, washed and dried. The precipitates were subjected to a silica gel column chromatography (chloroform:methanol=10:1) to give 1.50 g of the title compound.

TLC: Rf 0.30 (chloroform:methanol=9:1)

[Process 2] 1-Naphthoxyacetyl-Asn-(2S,3S)-AHPBA-Dtc-NH-tBu

Deprotection of 44 mg of the compound obtained by the process 1 was performed similarly to that in Example 28 (Process 3), and the obtained product was dissolved in 5 ml of DMF and neutralized with 10 µl of triethylamine under ice cooling. To the neutralized solution, 15 mg of 1-naphthoxyacetic acid, 32 mg of Bop reagent and 20 µl of triethylamine were added and the resultant mixture was stirred for 2 hr. The reaction mixture was treated similarly to that in Example 46, except for the chromatography solvent (chloroform:methanol=15:1), to give the above mentioned compound. The solid was dissolved in methanol, fractionated by a reversed-phase HPLC and lyophilized to give 10.5 mg of the title compound.

Analytical HPLC: 26.68 min (For the condition, see: Example 35.)

FAB-MS: 692 (M+1)

Figure 4:
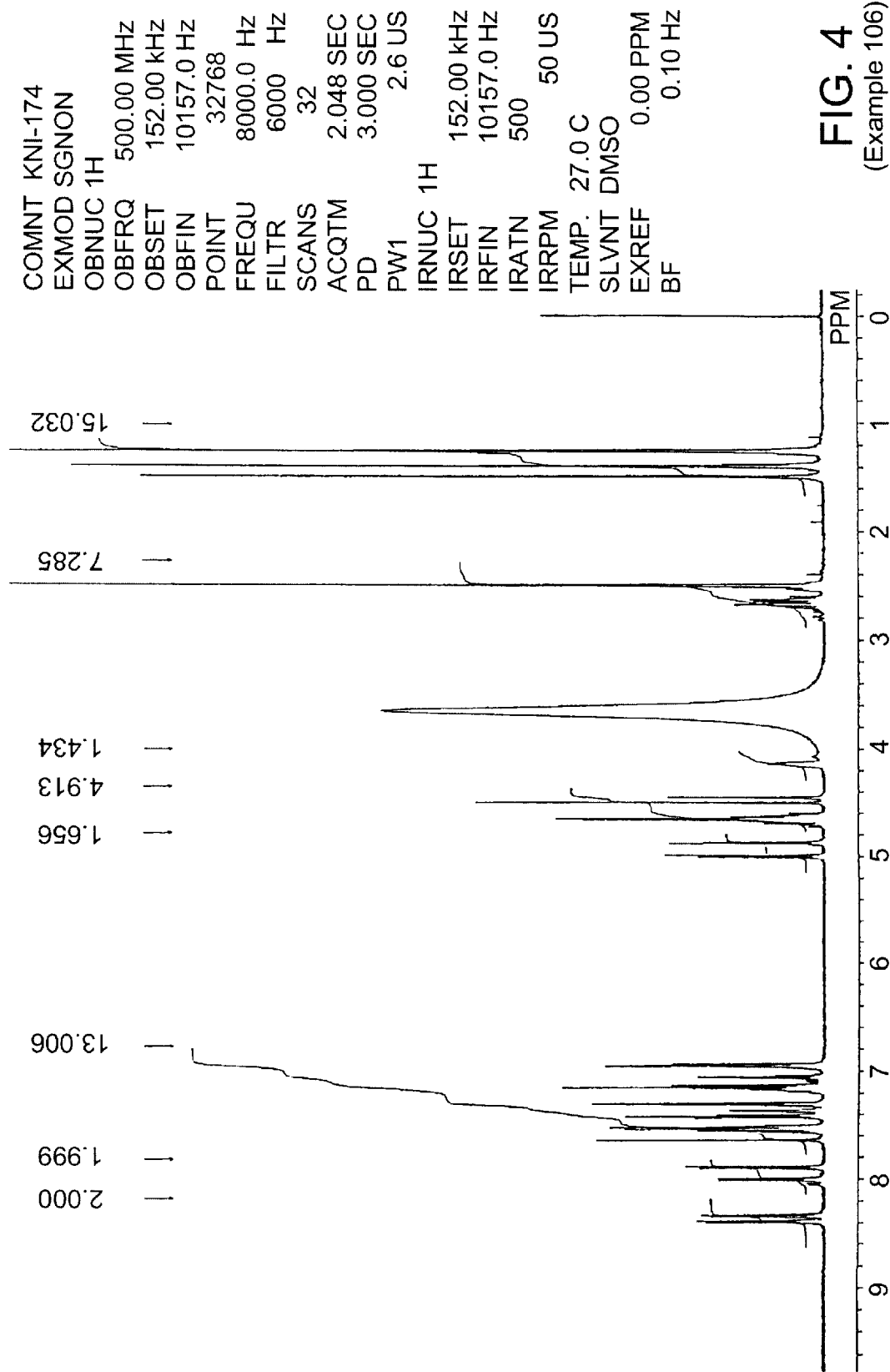

$^1$H NMR (DMSO-$d_6$, 500 MHz): FIG. 4

Example 107

1-Naphthylmethyloxycarbonyl-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 µl of triethylamine under ice cooling. To the neutralized solution, 32 mg of 1-naphthylmethyl 4-nitrophenyl carbonate, 15 mg of HOBt and 14 µl of N-methylmorpholine were added and the resultant mixture was stirred for 14 hr. The reaction mixture was evaporated under reduced pressure and the resultant residue was mixed with 5% aqueous sodium hydrogencarbonate solution to give precipitates. The precipitates were filtered, washed with water and dried. The dried precipitates were dissolved in methanol, fractionated by a reversed-phase HPLC and lyophilized to give 6.4 mg of the title compound.

Analytical HPLC: 26.93 min (For the condition, see: Example 35.)

FAB-MS: 692 (M+1)

Example 108

(E)-Phenyl-CH=CH—CH$_2$CO-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 µl of triethylamine under ice cooling. To the neutralized solution, 11 mg of trans-styrylacetic acid, 29 mg of Bop reagent and 18 µl of triethylamine were added and the resultant mixture was stirred for 2 hr. The reaction mixture was treated similarly to that in Example 107 to give 5.6 mg of the title compound.

Analytical HPLC: 24.49 min (For the condition, see: Example 35.)

FAB-MS: 652 (M+1)

Example 109 o-Chlorophenoxyacetyl-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 µl of triethylamine under ice cooling. To the neutralized solution, 11 mg of o-chlorophenoxyacetic acid, 29 mg of Bop reagent and 18 µl of triethylamine were added and the resultant mixture was stirred for 2 hr. The reaction mixture was treated similarly to that in Example 107 to give 10.5 mg of the title compound.

Analytical HPLC: 24.49 min (For the condition, see: Example 35.)

FAB-MS: 676 (M+1)

Example 110 o-Phenylphenoxyacetyl-Asn-(2S,3S)-AHPBA-Dtc-NH-tBu

[Process 1] o-Phenylphenoxyacetic acid DCHA salt

In 10 ml of acetonitrile, 1.0 g of o-phenylphenol and 1.29 ml of ethyl bromoacetate were added in the presence of 1.76 ml of 1,8-diazabicyclo[5.4.0]-7-undecene (DBU) and the resultant mixture was refluxed for 8 hr. The reaction mixture was treated similarly to that in Example 28 (Process 2) to give 1.46 g of ethyl o-phenylphenoxyacetate. The ester was dissolved in 30 ml of ethanol, mixed with 10.8 ml of 1N-NaOH aqueous solution and stirred for 12 hr. The reaction mixture was evaporated under reduced pressure, acidified by the addition of 1N-HCl and extracted with ethyl acetate. The extract was washed with saturated sodium chloride aqueous solution and dried over anhydrous sodium sulfate. The dried solution was evaporated under reduced pressure and o-phenylphenoxyacetic acid was crystallized as DCHA salt from ether with the yield of 1.59 g.

TLC: Rf 0.40 (chloroform:methanol:acetic acid=9:1:0.5)

[Process 2] o-Phenylphenoxyacetyl-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 µl of triethylamine under ice cooling. To the neutralized solution, 34 mg of o-phenylphenoxyacetic acid DCHA salt, 29 mg of Bop reagent and 18 µl of triethylamine were added and the resultant mixture was stirred for 2 hr. The reaction mixture was treated similarly to that in Example 107 to give 9.4 mg of the title compound.

Analytical HPLC: 28.38 min (For the condition, see: Example 35.)

FAB-MS: 718 (M+1)

Example 111 m-Phenylphenoxyacetyl-Asn-(2S,3S)-AHFBA-Dtc-NH-tBu

The compound shown above was obtained by the similar method to that of Example 110.

Analytical HPLC: 28.40 min (For the condition, see: Example 35.)

FAB-MS: 718 (M+1)

Example 112 p-Phenylphenoxyacetyl-Asn-(2S,3S)-AHPBA-Dtc-NH-tBu

The compound shown above was obtained by the similar method to that of Example 110.

Analytical HPLC: 28.16 min (For the condition, see: Example 35.)

FAB-MS: 718 (M+1)

Example 113 m-Chlorophenoxyacetyl-Asn-(2S,3S)-AHFBA-Dtc-NH-tBu

The compound shown above was obtained by the similar method to that of Example 110.

Analytical HPLC: 25.24 min (For the condition, see: Example 35.)

FAB-MS: 676 (M+1)

Example 114

5,6,7,8-Tetrahydro-1-naphthoxyacetyl-Asn-(2S,3S)-AHPBA-Dtc-NH-tBu

The compound shown above was obtained by the similar method to that of Example 110.

Analytical HPLC: 28.48 min (For the condition, see: Example 35.)

FAB-MS: 696 (M+1)

Example 115

5-Isoquinolyloxyacetyl-Asn-(2S,3S)-AHPBA-Dtc-NH-tBu

[Process 1] 5-Isoquinolyloxyacetic acid

In 10 ml of acetonitrile, 1.0 g of 5-hydroxyisoquinoline and 1.52 ml of ethyl bromoacetate were added in the presence of 2.07 ml of DBU and the resultant mixture was refluxed for 8 hr. The reaction mixture was evaporated under reduced pressure and the resultant residue was redissolved in 1N-HCl, washed with ethyl acetate. The aqueous layer was made alkaline with sodium hydrogencarbonate and extracted with ethyl acetate. The extract was washed with saturated sodium chloride aqueous solution and dried over anhydrous sodium sulfate. The dried solution was evaporated under reduced pressure and subjected to a silica gel column chromatography (chloroform) to give 1.46 g of ethyl 5-isoquinolyloxyacetate. The ester was dissolved in 30 ml of ethanol, mixed with 6.5 ml of 1N-NaOH aqueous solution and stirred for 12 hr. The reaction mixture was evaporated under reduced pressure, neutralized by the addition of 1N-HCl and the precipitated crystals were filtered, washed with water and dried to give 0.68 g of the title compound.

[Process 2] 5-Isoquinolyloxyacetyl-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 μl of triethylamine under ice cooling. To the neutralized solution, 14 mg of 5-isoquinolyloxyacetic acid, 29 mg of Bop reagent and 18 μl of triethylamine were added and the resultant mixture was stirred for 2 hr. The reaction mixture was treated similarly to that in Example 107 to give 3.3 mg of the title compound.

Analytical HPLC: 14.84 min (For the condition, see: Example 35.)

FAB-MS: 693 (M+1)

Example 116 m-Phenylaminophenoxyacetyl-Asn-(2S,3S)-AHPBA-Dtc-NH-tBu

The compound shown above was obtained by a similar method to that of Example 115.

Analytical HPLC: 26.97 min (For the condition, see: Example 35.)

FAB-MS: 733 (M+1)

Example 117

8-Quinolyloxyacetyl-Asn-(2S,3S)-AHPBA-Dtc-NH-tBu

The compound shown above was obtained by a similar method to that of Example 115.

Analytical HPLC: 15.49 min (For the condition, see: Example 35.)

FAB-MS: 693 (M+1)

Example 118

2-Quinolinecarbonyl-Asn-(2S,3S)-AHPBA-Dtc-NH-tBu

Deprotection of 40 mg of the compound obtained by Example 106 (Process 1) was performed similarly to that in Example 28 (Process 3), and the obtained product was dissolved in 5 ml of DMF and neutralized with 9 μl of triethylamine under ice cooling. To the neutralized solution, 12 mg of 2 quinolinecarboxylic acid, 29 mg of Bop reagent and 18 μl of triethylamine were added and the resultant mixture was stirred for 2 hr. The reaction mixture was evaporated under reduced pressure and the resultant residue was re-dissolved in ethyl acetate. The extract was washed with 5% sodium hydrogencarbonate aqueous solution, then with saturated sodium chloride aqueous solution and dried over anhydrous sodium sulfate. The dried solution was evaporated under reduced pressure, dissolved in methanol, fractionated by a reversed-phase HPLC and lyophilized to give 7.2 mg of the title compound.

Analytical HPLC: 24.25 min (For the condition, see: Example 35.)

FAB-MS: 648 (M+1)

Example 119

1-Naphthoxyacetyl-Mta-(2S,3S)-AHPBA-Dtc-NF-tBu

[Process 1] Boc-Mta-(2S,3S)-AHPBA-Dtc-NH-tBu

Deprotection of 390 mg of the compound obtained by Example 104 (Process 2) was performed similarly to that in Example 28 (Process 3), and the obtained product was dissolved in 10 ml of DMF and neutralized with 110 μl of triethylamine under ice cooling. To the neutralized solution, 186 mg of Boc-methylthioalanine, 349 mg of Bop reagent and 220 μl of triethylamine were added and the resultant mixture was stirred for 2 hr. The reaction mixture was treated similarly to that in Example 28 (Process 3) to give 166 mg of the title compound.

TLC: Rf 0.63 (chloroform:methanol=9:1)

[Process 2] 1-Naphthoxyacetyl-Mta-(2S,3S)-AHPBA-Dtc-NH-tBu

Deprotection of 50 mg of the compound obtained by the process 1 was performed similarly to that in Example 28 (Process 3) in the presence of 25 μl of anisole, and the obtained product was dissolved in 3 ml of DMF and neutralized with 12 μl of triethylamine under ice cooling. To the neutralized solution, 17 mg of 1-naphthoxyacetic acid, 36 mg of Bop reagent and 23 μl of triethylamine were added and the resultant mixture was stirred for 2 hr. The reaction mixture was treated similarly to that in Example 93 (Process 3) to give 61 mg of the crude above mentioned compound. In methanol, 40 mg of the crude solid was dissolved, fractionated by a reversed-phase HPLC and lyophilized to give 17.7 mg of the title compound.

Analytical HPLC: 27.88 min (The condition was as follows)

Column: YMC AM-302 (4.6×150 mm)

Solvent A: 0.1% trifluoroacetic acid aqueous solution

Solvent B: acetonitrile

Gradient: 30% B for 2 min, then B was increased in 2%/min

Flow rate: 0.7 ml/min

FAB-MS: 695 (M+1)

Example 120

8-Quinolyloxyacetyl-Mta-(2S,3S)-AHPBA-Dtc-NH-tBu

The compound shown above was obtained by a similar method to that of Example 115.

Analytical HPLC: 18.89 min (For the condition, see: Example 35.)

FAB-MS: 696 (M+1)

Example 121

1-Naphthoxyacetyl-Mta+(Me)-(2S,3S)-AHPBA-Dtc-NH-tBu.AcO−

In methanol solution containing 10 mg of compound obtained by Example 119, 200 μl of methyl iodide was added and the resultant mixture was stirred for 7 days at 4° C. The reaction mixture was purified by a reversed-phase HPLC (0.1% AcOH-acetonitrile) to give 4.2 mg of the title compound.

Analytical HPLC: 18.90 min (For the condition, see: Example 119.)

Example 122

1-Naphthoxyacetyl-Mta-(2S,3S)-AHPBA-Pro-NH-tBu

[Process 1] Boc-Mta-(2S,3S)-AHPBA-Pro-NH-tBu

Deprotection of 20 mg of the compound obtained by Example 55 (Process 2) was performed similarly to that in Example 28 (Process 3), and the obtained product was dissolved in 3 ml of DMF and neutralized with 6.2 μl of triethylamine under ice cooling. To the neutralized solution, 11 mg of Boc-methylthioalanine, 20 mg of Bop reagent and 12.4 μl of triethylamine were added and the resultant mixture was stirred for 2 hr. The reaction mixture treated similarly to that in Example 46 to give 24 mg of the title compound.

TLC: Rf 0.37 (chloroform:methanol=9:1)

[Process 2] 1-Naphthoxyacetyl-Mta-(2S,3S)-AHPBA-Pro-NH-tBu

Deprotection of 24 mg of the compound obtained by the process 1 was performed similarly to that in Example 28 (Process 3) in the presence of 12 μl of anisole, and the obtained product was dissolved in 3 ml of DMF and neutralized with 5.9 μl of triethylamine under ice cooling. To the neutralized solution, 8.6 mg of 1-naphthoxyacetic acid, 18.8 mg of Bop reagent and 11.8 μl of triethylamine were added and the resultant mixture was stirred for 2 hr. The reaction mixture was treated similarly to that in Example 93 (Process 3) to give the crude compound mentioned above. In methanol, the crude product was dissolved, fractionated by a reversed-phase HPLC and lyophilized to give 6.6 mg of the title compound.

Analytical HPLC: 29.52 min (For the condition, see: Example 35.)

FAB-MS: 649 (M+1)

Example 123

1-Naphthylaminoacetyl-Msa-(2S,3)-AHFBA-Pro-NH-tBu.AcOH

[Process 1] 1-Naphthylaminoacetic acid

In 5 ml of THF, 500 mg of 1-naphthylamine was added, then 168 mg of sodium hydride (60% in oil) was added and the resultant mixture was stirred for 30 min under ice cooling. To the reaction mixture, 0.46 ml of ethyl bromoacetate was added and the mixture was refluxed for 5 hr. The reaction mixture was evaporated under reduced pressure and the resultant residue was re-dissolved in ethyl acetate. The obtained solution was washed with 5% sodium hydrogencarbonate aqueous solution and saturated sodium chloride aqueous solution, successively, and dried over anhydrous sodium sulfate. The dried solution was evaporated. under reduced pressure and subjected to a silica gel column chromatography (n-hexane:ethyl acetate=10:1) to give 720 mg of ethyl 1-naphthylaminoacetate. In 10 ml of ethanol, 460 mg of the ester was dissolved, 3.78 ml of 1N-NaOH aqueous solution was added and the resultant mixture was stirred for 1 hr. The reaction mixture was evaporated under reduced pressure, neutralized by the addition of 1N-HCl and extracted with ethyl acetate. The extract was washed with saturated sodium chloride aqueous solution and dried over anhydrous sodium sulfate. The dried solution was evaporated under reduced pressure and crystallized by the treatment with ether to give 188 mg of the title compound.

TLC: Rf 0.46 (chloroform:methanol:acetic acid=9:1:0.5)

[Process 2] 1-Naphthylaminoacetyl-Msa-(2S,3S)-AHPBA-Pro-NH-tBu.AcOH

Deprotection of 20 mg of the compound obtained by example 90 (Process 1) was performed similarly to that in Example 28 (Process 3), and the obtained product was dissolved in 3 ml of DMF and neutralized with 4.7 µl of triethylamine under ice cooling. To the neutralized solution, 8.4 mg of 1-naphthylaminoacetic acid, 15 mg of Bop reagent and 9.5 µl of triethylamine were added and the resultant mixture was stirred for 2 hr. The reaction mixture was evaporated under reduced pressure and the resultant residue was re-dissolved in ethyl acetate. The obtained solution was washed with 5% sodium hydrogencarbonate aqueous solution and saturated sodium chloride aqueous solution, successively, and dried over anhydrous sodium sulfate. The dried solution was evaporated under reduced pressure and subjected to a silica gel column chromatography (chloroform:methanol=20:1) and treated with ether to give 20 mg of the crude compound mentioned above. In methanol, 6 mg of the crude crystals were dissolved, fractionated by a reversed-phase HPLC (0.1% acetic acid-acetonitrile system), lyophilized to give 3.3 mg of the title compound.

Analytical HPLC: 24.81 min (For the condition, see: that in example 35.)

FAB-MS: 680 (M+1)

Example 124

1-Naphthylaminoacetyl-Msa-(2S,3S)-AHPBA-Thz-NH-tBu.AcOH

The above mentioned compound was obtained by a similar method of: Example 123 [process 23.

Analytical HPLC: 27.08 min (For the condition, see: that in example 35.)

FAB-MS: 698 (M+1)

Example 125

1-Naphthoxyacetyl-Msa-(2S,3S)-AHPBA-Thz-NH—C(CH$_3$)$_2$—CH$_2$OH

[Process 1] Boc-Thz-NH—C(CH$_3$)$_2$—CH$_2$OH

In a methylene chloride solution containing 0.30 g of Boc-Thz-OH, 0.12 ml of 2-amino-2-methyl-1-propanol and 0.29 g of EDC hydrochloride were added and the resultant mixture was stirred for 14 hr. The reaction mixture was treated similarly to that in Example 33 (Process 3) to give 190 mg of the title compound.

TLC: Rf 0.87 (chloroform:methanol:water=8:3:1, lower layer)

[Process 2] Boc-(2S,3S)-AHFBA-Thz-NH—C(CH$_3$)$_2$—CH$_2$OH

To 40 mg of the protected peptide obtained by the [process 1], 5 ml of trifluoroacetic acid was added and the resultant mixture was stirred for 60 min at room temperature. The reaction mixture was evaporated under reduced pressure, and the resultant residue was washed with n-hexane and redissolved in 5 ml of DMF and neutralized with 19 µl of triethylamine under ice cooling. To the neutralized solution, 63 mg of Boc-(2S,3S)-AHPBA-OH.DCHA, 58 mg of Bop reagent and 36 µl of triethylamine were added and the resultant mixture was stirred for 2 hr. The reaction mixture was treated similarly to that in Example 93 (Process 3) to give 51 mg of the title compound.

TLC: Rf 0.75 (chloroform:methanol:water=8:3:1, lower layer)

[Process 3] Boc-Msa-(2S,3S)-AHPBA-Thz-NH—C(CH$_3$)$_2$—CH$_2$OH

Deprotection of 51 mg of the compound obtained by the process 2 was performed similarly to that in Example 125 (Process 2), and the obtained product was dissolved in 5 ml of DMF and neutralized with 14 µl of triethylamine under ice cooling. To the neutralized solution, 26 mg of Boc-methanesulfonylalanine, 45 mg of Bop reagent and 28 µl of triethylamine were added and the resultant mixture was stirred for 2 hr. The reaction mixture was treated similarly to that in Example 46 to give 31 mg of the title compound.

TLC: Rf 0.81 (chloroform:methanol:water=8:3:1, lower layer)

[Process 4] 1-Naphthoxyacetyl-Msa-(2S,3S)-AHPBA-Thz-NH—C(CH$_3$)$_2$CH$_2$OH

Deprotection of 31 mg of the compound obtained by the process 3 was Performed similarly to that in Example 125 (Process 2), and the obtained product was dissolved in 3 ml of DMF and neutralized with 7 µl of triethylamine under ice cooling. To the neutralized solution, 9.7 mg of 1-naphthoxyacetic acid, 21.1 mg of Bop reagent and 13.3 µl of triethylamine were added and the resultant mixture was stirred for 2 hr. The reaction mixture was treated similarly to that in Example 122 to give 10.6 mg of the title compound.

Analytical HPLC: 22.88 min (For the condition, see: that in example 35.)

FAB-MS: 715 (M+1)

Example 126

1-Naphthoxyacetyl-Msa-(2S,3S)-AHPBA-Pro-NH—C(CH$_3$)(CH$_2$OH)$_2$

[Process 1] Boc-Pro-NH—C(CH$_3$)(CH$_2$OH)$_2$

In a methylene chloride solution containing 0.20 g of Boc-Pro-OH, 0.49 g of 2-amino-2-methyl-1,3-propanediol and 0.89 g of EDC hydrochloride were added and the resultant mixture was stirred for 14 hr. The reaction mixture was treated similarly to that in Example 51 (Process 1) without filtration to give 0.36 g of the title compound.

TLC: Rf 0.48 (chloroform:methanol:acetic acid=9:1:0.5)

[Process 2] Boc-(2S,3S)-AHPBA-Pro-NH—C(CH$_3$)(CH$_2$OH)$_2$

Deprotection of 50 mg of the compound obtained by the process 1 was performed similarly to that in Example 125 (Process 2), and the obtained product was dissolve A in 5 ml of DMF and neutralized with 22 µl of triethylamine under ice cooling. To the neutralized solution, 75 mg of Boc-(2S,3S)-AHPBA-OH.DCHA, 70 mg of Bop reagent and 22 µl of triethylamine were added and the resultant mixture was stirred for 2 hr. The reaction mixture was treated similarly to that in Example 93 (Process 3) to give 42 mg of the title compound.

TLC: Rf 0.74 (chloroform:methanol:water=8:3:1, lower layer)

[Process 3] Boc-Msa-(2S,3S)-AHPBA-Pro-NH—C(CH$_3$)(CH$_2$OH)$_2$

Deprotection of 42 mg of the compound obtained by the process 2 was performed similarly to that in Example 125 (Process 2), and the obtained product was dissolved in 5 ml of DMF and neutralized with 12 µl of triethylamine under ice cooling. To the neutralized solution, 23 mg of Boc-methanesulfonylalanine, 38 mg of Bop reagent and 12 µl of triethylamine were added and the resultant mixture was stirred for 2 hr. The reaction mixture was treated similarly to that in Example 93 (Process 3) to give 25 mg of the title compound.

TLC: Rf 0.63 (chloroform:methanol:water=8:3:1, lower layer)

[Process 4] 1-Napthoxyacetyl-Msa-(2S,3S)-AHPBA-Pro-NH—C(CH$_3$)(CH$_2$OH)$_2$

Deprotection of 25 mg of the compound obtained by the process 3 was performed similarly to that in Example 125 (Process 2), and the obtained product was dissolved in 3 ml of DMF and neutralized with 5.4 μl of triethylamine under ice cooling. To the neutralized solution, 7.8 mg of 1-naphthoxyacetic acid, 17.1 mg of Bop reagent and 10.8 μl of triethylamine were added and the resultant mixture was stirred for 2 hr. The reaction mixture was treated similarly to that in Example 122 to give 4.5 mg of the title compound.

Analytical HPLC: 19.37 min (For the condition, see: that in example 35.)

FAB-MS: 713 (M+1)

Example 127

1-Naphthoxyacetyl-Asn-(2S,3S)-AHPBA-Thz-piperidine

[Process 1] Boc-Thz-piperidine

In a methylene chloride solution containing 300 mg of Boc-Thz-OH, 358 μl of triethylamine, 358 mg of 2-chloro-1,3-dimethylimidazolidinium hexafluorophosphate and 153 μl of piperidine were added under ice cooling and the resultant mixture was stirred for 14 hr. The reaction mixture was treated similarly to that in Example 33 (Process 3) to give 300 mg of the title compound.

TLC: Rf 0.41 (chloroform:methanol=40:1)

[Process 2] Boc-(2S,3S)-AHPBA-Thz-piperidine

Deprotection of 100 mg of the compound obtained by the process 1 was performed similarly to that in Example 28 (Process 3), and the obtained product was dissolved in 10 ml of methylene chloride and neutralized with 46 μl of triethylamine under ice cooling. To the neutralized solution, 159 mg of Boc-(2S,3S)-AHPBA-OH.DCHA, 147 mg of Bop reagent and 46 μl of triethylamine were added and the resultant mixture was stirred for 2 hr. The reaction mixture was treated similarly to that in Example 46 to give 134 mg of the title compound.

TLC: Rf 0.59 (chloroform:methanol=9:1)

[Process 3] Boc-Asn-(2S,3S)-AHPBA-Thz-piperidine

Deprotection of 103 mg of the compound obtained by the process 2 was performed similarly to that in Example 28 (Process 3), and the obtained product was dissolved in 10 ml of DMF and neutralized with 30 μl of triethylamine under ice cooling. To the neutralized solution, 114 mg of Boc-Asn-ONp, 50 mg of HOBt, 36 μl of N-methylmorpholine were added and the resultant mixture was stirred for 14 hr. The reaction mixture was evaporated under reduced pressure and the resultant residue was mixed with 5% sodium hydrogencarbonate aqueous solution. The obtained solid was subjected to a silica gel column chromatography (chloroform:methanol=10:1) to give 6 mg of the title compound.

TLC: Rf 0.69 (chloroform:methanol:water=8:3:1, lower layer)

[Process 4] 1-Naphthoxyacetyl-Asn-(2S,3S)-AHPBA-Thz-piperizine

Deprotection of 65 mg of the compound obtained by the process 3 was performed similarly to that in Example 28 (Process 3) and the obtained product was dissolved in 8 ml of DMF and neutralized with 15 μl of triethylamine under ice cooling. To the neutralized solution, 23 mg of 1-naphthoxyacetic acid, 49 mg of Bop reagent and 30 μl of triethylamine were added and the resultant mixture was stirred for 2 hr. The reaction mixture was evaporated under reduced pressure and the resultant residue was mixed with 5% sodium hydrogencarbonate aqueous solution to give precipitates. The formed precipitates were collected, washed with water and dried in vacuo to give 63 mg of the crude product. It methanol, 25 mg of the crude product was dissolved, fractionated by a reversed-phase HPLC and lyophilized to give 6.8 mg of the title compound.

Analytical HPLC: 20.42 min (For the condition, see: that in example 33.)

FAB-MS: 676 (M+1)

Example 128

1-Naphthoxyacetyl-Asn-(2S,3S)-AHPBA-Thz-NH-cyclopentyl

[Process 1] Boc-Thz-NH-cyclopentyl

In a methylene chloride solution containing 200 mg of Boc-Thz-OH, 238 μl of triethylamine, 379 mg of Bop reagent, and 102 μl of cyclopentylamine were added under ice cooling and the resultant mixture was stirred for 14 hr. The reaction mixture was treated similarly to that in Example 28 (Process 3) to give 235 mg of the title compound.

[Process 2] Boc-(2S,3S)-AHPBA-Thz-NH-cyclopentyl

Deprotection of 100 mg of the compound obtained by the process 1 was performed similarly to that in Example 28 (Process 3), and the obtained product was dissolved in 10 ml of methylene chloride and neutralized with 46 μl of triethylamine under ice cooling. To the neutralized solution, 159 mg of Boc-(2S,33)-AHPBA-OH DCHA salt, 147 mg of Bop reagent and 46 μl of triethylamine were added and the resultant mixture was stirred for 2 hr. The reaction mixture was treated similarly to that in Example 46 to give 50 mg of the title compound.

TLC: Rf 0.59 (chloroform:methanol=9:1)

[Process 3] Boc-Asn-(2S,3S)-AHPBA-Thz-NH-cyclopentyl

Deprotection of 50 mg of the compound obtained by the process 2 was performed similarly to that in Example 28 (Process 3), and the obtained product was dissolved in 5 ml of DMF and neutralized with 15 μl of triethylamine under ice cooling. To the neutralized solution, 56 mg of Boc-Asn-ONp, 24 mg of HOBt and 17 μl of N-methyimorpholine were added and the resultant mixture was stirred for 14 hr. The reaction mixture was treated similarly to that in ExampLe 93 (Process 3) to give 20 mg of the title compound.

TLC: Rf 0.66 (chloroform:methanol:water=8:3:1, lower layer)

[Process 4] 1-Naphthoxyacetyrl-Asn-(2S,3S)-AHPBA-Thz-NH-cyclopentyl

The compound mentioned above was obtained by a similar method to that in Example 127, [process 4].

Analytical HPLC: 24.13 min (For the condition, see: that in Example 35.)

FAB-MS: 676 (M+1)

Example 129 m-Phenylphenoxyacetyl-Mta-(2S,3S)-AHPBA-Dtc-NH-tBu

The compound mentioned above was obtained by a similar method to that in Example 119.

Analytical HPLC: 29.01 min (For the condition, see: that in Example 119.)

FAB-MS: 721 (M+1)

Example 130 m-Isoquinolyloxyacetyl-Mta-(2S 3S)-AHPBA-Dtc-NH-tBu

The compound mentioned above was obtained by a similar method to that in Example 123 (Process 2) using the compounds obtained in Example 119 (Process 1) and Example 115 (Process 1).

Analytical HPLC: 18.00 min (For the condition, see: that in example 35.)

FAB-MS: 696 (M+1)

Figure 5:
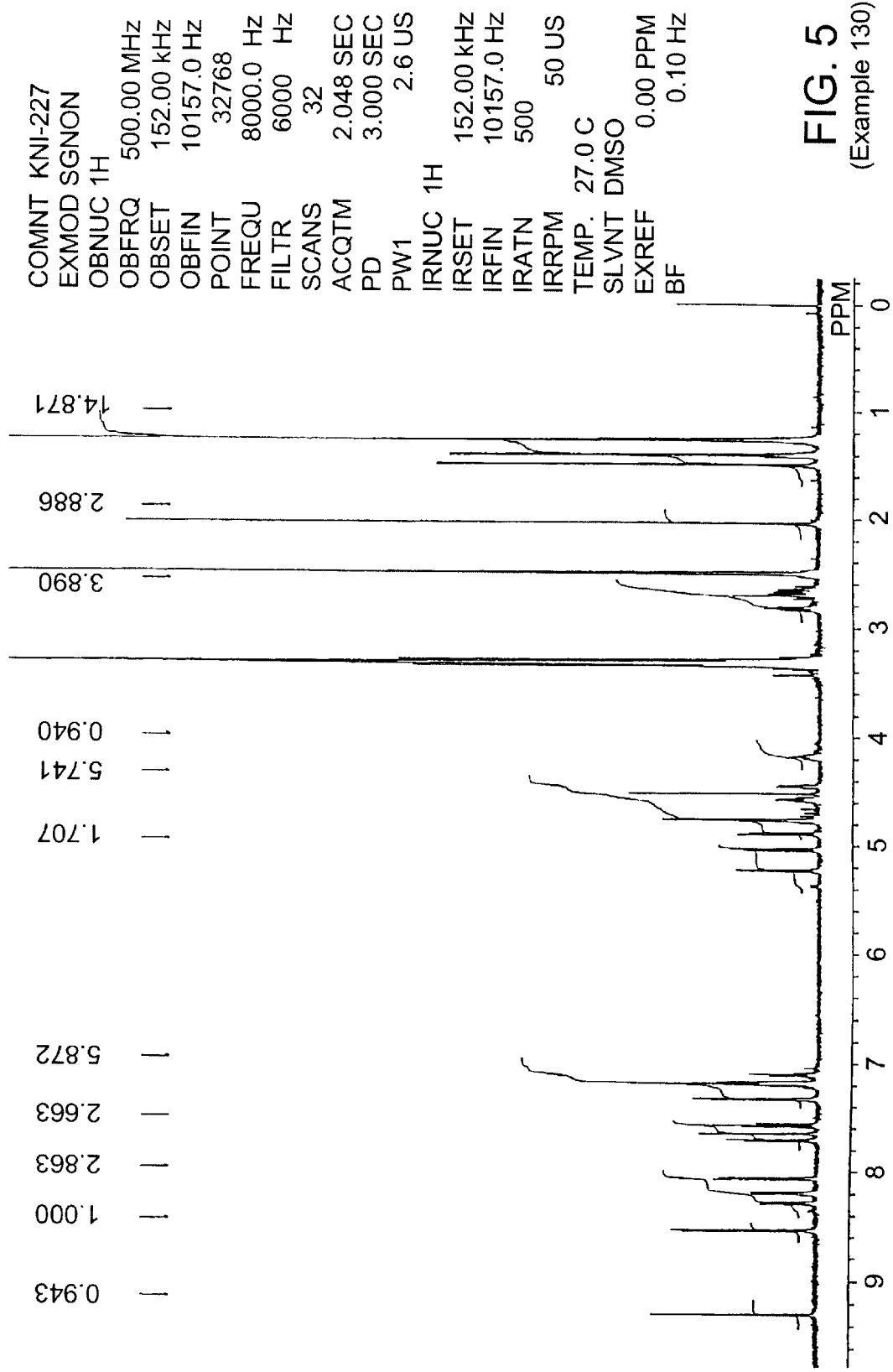
Figure 6:
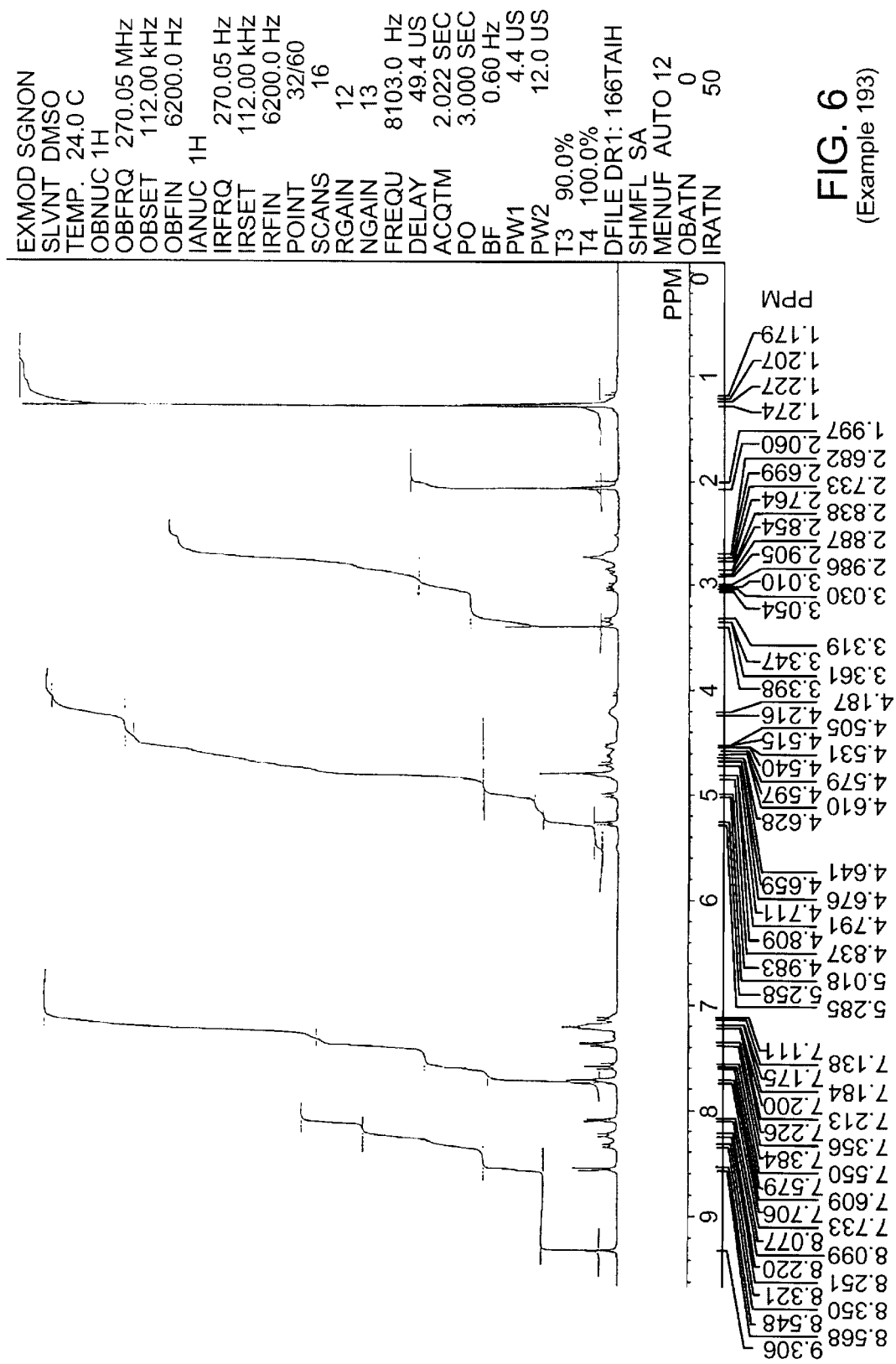

$^1$H NMR (DMSO-$d_6$, 500 MHz): FIG. 5

Example 131

2-Naphthoxyacetyl-Msa-(2S,3S)-AHPBA-Pro-NH-tBu

Deprotectionof 23 mg of the compound obtained by Example 90 (Process 1) was performed similarly to that in Example 28 (Process 3), and the obtained product was dissolved in 3 ml of DMF and neutralized with 5.4 µl of triethylamine under ice cooling. To the neutralized solution, 8 mg of 2-naphthoxyacetic acid, 17 mg of Bop reagent and 11 µl of triethylamine were added and the resultant mixture was stirred for 2 hr. The reaction mixture was treated similarly to that in Example 30 (Process 4) and treated with hexane to give 22 mg of the crude compound mentioned above. In methanol, 22 mg of the crude crystals were dissolved and, fractionated by a reversed-phase HPLC and lyophilized to give 11.8 mg of the title compound.

TLC: Rf 0.88 (chloroform:methanol=9:1)

Analytical HPLC: 25.39 min (For the condition, see: that in example 35.)

FAB-MS: 581 (M+1)

Example 132

1-Naphthoxyacetyl-Hse-(2S,3S)-AHPBA-Thz-NH-tBu

[Process 1] Boc-Hse-(2S,3S)-AHPBA-Thz-NH-tBu

Deprotection of 21 mg of the compound obtained by Example 82 (Process 2) was performed similarly to that in Example 28 (Process 3), and the obtained product was dissolved in 3 ml of DMF and neutralized with 6.3 µl of triethylamine under ice cooling. To the neutralized solution, 18 mg of Boc-Hse-OH.DCHA, 20 mg of Bop reagent and 6.3 µl of triethylamine were added and the resultant mixture was stirred for 2 hr. The reaction mixture was treated similarly to that in Example 28 (Process 2), except for the chromatography solvent (chloroform:methanol=40:1), to give 20 mg of the title compound.

TLC: Rf 0.83 (chloroform:methanol=9:1)

[Process 2] 1-Naphthoxyacetyl-Hse-(2S,3S)-AHPBA-Thz-NH-tBu

Deprotection of 20 mg of the compound obtained by the process 1 was performed similarly to that in Example 28 (Process 3), and the obtained product was dissolved in 3 ml of DMF and neutralized with 4.9 µl of triethylamine under ice cooling. To the neutralized solution, 8 mg of 1-naphthoxyacetic acid, 16 mg of Bop reagent and 9.8 µl of triethylamine were added and the resultant mixture was stirred for 2 hr. The reaction mixture was treated similarly to that in the process 1 to give 22 mg of the crude compound mentioned above. In methanol, the crude product was dissolved, fractionated by a reversed-phase HPLC and lyophilized to give 6.1 mg of the title compound.

TLC: Rf 0.57 (chloroform:methanol=9:1)

Analytical HPLC: 21.31 min (For the condition, see: that in example 35.)

FAB-MS: 651 (M+1)

Example 133

1-Naphthoxyacetyl-Thr-(2S,3S)-AHFBA-Thz-NH-tBu

[Process 1] Boc-Thr-(2S,3S)-AHPBA-Thz-NH-tBu

Deprotection of 19 mg of the compound obtained by Example 82 (Process 2) was performed similarly to that in Example 28 (Process 3), and the obtained product was dissolved in 3 ml of DMF and neutralized with 4.3 µl of triethylamine under ice cooling. To the neutralized solution, 9 mg of Boc-Thr-OH, 18 mg of Bop reagent and 6.2 µl of triethylamine were added and the resultant mixture was stirred for 2 hr. The reaction mixture was treated similarly to that in Example 132 (Process 1) to give 24 mg of the title compound.

TLC: Rf 0.66 (chloroform:methanol=9:1)

[Process 2] 1-Naphthoxyacetyl-Thr-(2S,3S)-AHPBA-Thz-NH-tBu

Deprotection of 29 mg of the compound obtained by the process 1 was performed similarly to that in Example 28 (Process 3), and the obtained product was dissolved in 3 ml of DMF and neutralized with 7.1 µl of triethylamine under ice cooling. To the neutralized solution, 11 mg of 1-naphthoxyacetic acid, 23 m. of Bop reagent and 14.2 µl of triethylamine were added and the resultant mixture was stirred for 2 hr. The reaction mixture was treated similarly to that in Example 132 (Process 2) to give 6.7 mg of the title compound.

TLC: Rf 0.66 (chloroform:methanol=9:1)

Analytical HPLC: 26.32 min (For the condition, see: that of Example 35.)

FAB-MS: 651 (M+1)

Example 134

1-Naphthoxyacetyl-Ile-(2S,3S)-AHPBA-Thz-NH-tBu

[Process 1] Boc-TIe-(2S,3S)-AHPBA-Thz-NH-tBu

Deprotection of 39 mg of the compound obtained by Example 82 (Process 2) was performed similarly to that in Example 28 (Process 3), and the obtained product was dissolved in 3 ml of DMF and neutralized with 11.6 µl of triethylamine under ice cooling. To the neutralized solution, 19.4 mg of Boc-Tle-OH, 37 mg of Bop reagent and 23.3 µl of triethylamine were added and the resultant mixture was stirred for 2 hr. The reaction mixture was treated similarly to that in Example 132(Process 1) to give 17 mg of the title compound.

TLC: Rf 0.94 (chloroform:methanol=9:1)

[Process 2] 1-Naphthoxyacetyl-Tle-(2S,3S)-AHBA-Thz-NH-tBu

Deprotection of 17 mg of the compound obtained by the process 1 was performed similarly to that in Example 28 (Process 3), and the obtained product was dissolved in 3 ml of DMF and neutralized with 4.1 µl of triethylamine under ice cooling. To the neutralized solution, 11 mg of 1-naphthoxyacetic acid, 13 mg of Bop reagent and 8.2 µl of triethylamine were added and the resultant mixture was stirred for 2 hr. The reaction mixture was treated similarly to that in Example 30 (Process 3) to give 15 mg of the crude compound. The crude product was dissolved in methanol, fractionated by a reversed-phase HPLC and lyophilized to give 2.3 mg of the title compound.

TLC: Rf 0.87 (chloroform:methanol=9:1)

Analytical HPLC: 31.60 min (For the condition, see: that in example 35.)

FAB-MS: 663 (M+1)

Example 135

1-Naphthoxyacetyl-Msa-(2S,3S)-AHPBA-Thz-NH—CH(CH(CH$_3$)$_2$)—CH$_2$OH

[Process 1] Boc-Valinol [Boc-Valol]

In 5 ml of 1,2-dimethoxyethane (DME), 1.086 g of Boc-Val-OH was dissolved and 550 µl of N-methylmorpholine and 650 µl of isobutyl chloroformate were successively added dropwise at −15° C. After stirring for 1 min, N-methylmorpholine hydrochloride was filtered off and washed twice with 2.5 ml each of DME. The filtrate and washings were combined and a solution of 284 mg of sodium borohydride in 2.5 ml of water was added in one portion. After 30 sec, 125 ml of water was added and the mixture was extracted with 25 ml of ethyl acetate and dried over anhydrous sodium sulfate. The dried solution was evaporated under reduced pressure to give 879 mg of the title compound.

TLC: Rf 0.52 (chloroform:methanol=20:1)

[Process 2] Boc-Thz-Valol

Deprotection of 94 mg of the compound obtained by the process 1 was performed similarly to that in Example 30 (Process 2), and the obtained product was dissolved in 3 ml of DMF and neutralized with 88.9 µl of triethylamine under ice cooling. To the neutralized solution, 164 mg of Boc-Thz-OH, 108 mg of HOBt and 147 mg of EDC hydrochloride were added and the resultant mixture was stirred for 2 hr. The reaction mixture was treated similarly to that in Example 132 (Process 1) to give 50 mg of the title compound.

TLC: Rf 0.60 (chloroform:methanol=9:1)

[Process 3] Boc-(2S,3S)-AHPBA-Thz-Valol

Deprotection of 50 mg of the compound obtained by the process 2 was performed similarly to that in Example 125 (Process 2), and the obtained product was dissolved in 3 ml of DMF and neutralized with 21.8 µl of triethylamine under ice cooling. To the neutralized solution, 75 mg of Boc-(2S,3S)-AHPBA-OH.DCHA, 70 mg of Bop reagent and 43.6 µl of triethylamine were added and the resultant mixture was stirred for 2 hr. The reaction mixture was treated similarly to that in Example 30 (Process 4) to five 39 mg of the title compound.

TLC: Rf 0.45 (chloroform:methanol=9:1)

[Process 4] Boc-Msa-(2S,3S)-AHPBA-Thz-Valol

Deprotection of 39 mg of the compound obtained by the process 3 was performed similarly to that in Example 30 (Process 2), and the obtained product was dissolved in 3 ml of DMF and neutralized with 10.9 µl of triethylamine under ice cooling. To the neutralized solution, 22 mg of Boc-Msa-OH, 35 mg of Bop reagent and 21.9 µl of triethylamine were added and the resultant mixture was stirred for 2 hr. The reaction mixture was treated similarly to that in Example 132 (Process 1) to give 25 mg of the title compound.

TLC: Rf 0.83 (chloroform:methanol=9:1)

[Process 5] 1-Naphthoxyacetyl-Msa-(2S,3S)-AHPBA-Thz-Valol

Deprotection of 25 mg of the compound obtained by the process 4 was performed similarly to that in Example 30 (Process 2), and the obtained product was dissolved in 3 ml of DMF and neutralized with 5.4 µl of triethylamine under ice cooling. To the neutralized solution, 8 mg of 1-naphthoxyacetic acid, 18 mg of Bop reagent and 10.8 µl of triethylamine were added and the resultant mixture was stirred for 2 hr. The reaction mixture was treated similarly to that in Example 132 (Process 2) to give 2.8 mg of the title compound.

TLC: Rf 0.47 (chloroform:methanol=9:1)

Analytical HPLC: 24.06 min (For the condition, see: that of example 35)

FAB-MS: 729 (M+1)

Example 136

2-Benzofurancarbonyl-Msa-(2S,3S)-AHPBA-Thz-NH-tBu

Deprotection of 52 mg of the compound obtained by Example 100 (Process 1) was performed similarly to that in Example 28 (Process 3), and the obtained product was dissolved in 3 ml of DMF and neutralized with 11.8 µl of triethylamine under ice cooling. To the neutralized solution, 14 mg of 2-benzofurancarboxylic acid, 38 mg of Bop reagent and 23.5 µl of triethylamine were added and the resultant mixture was stirred for 2 hr. The reaction mixture was treated similarly to that in Example 132 (Process 2) to give 1.9 mg of the title compound.

TLC: Rf 0.64 (chloroform:methanol=9:1)

Analytical HPLC: 24.44 min (For the condition, see: that in example 35.)

FAB-MS: 659 (M+1)

Example 137

1-Naphthoxyacetyl-Msa-(2S,3S)-AHPBA-Thz-NH—CH(CH$_3$)—(C$_2$H$_5$))—CH$_2$OH

[Process 1] Boc-Isoleucinol [Boc-Ileol]

In 5 ml of 1,2-dimethoxyethane (DME), 1.201 g of Boc-Ile-OH.1/2H$_2$O was dissolved and 550 µl of N-methylmorpholine and 650 µl of isobutyl chloroformate were successively added dropwise at −15° C. After stirring for 1 min, the formed N-methylmorpholine hydrochloride was filtered off and washed twice with 2.5 ml each of DME. The filtrate and washings were combined and 284 mg of sodium borohydride in 2.5 ml of water was added in one portion. After 30 sec, 125 ml of water was added and the mixture was extracted with 25 ml of ethyl acetate and dried over anhydrous sodium sulfate. The dried solution was evaporated under reduced pressure to give 1.040 g of the title compound.

TLC: Rf 0.46 (chloroform:methanol=20:1)

[Process 2] Boc-Thz-Ileol

Deprotection of 127 mg of the compound obtained by the process 1 was performed similarly to that in Example 30 (Process 2), and the obtained product was dissolved in 3 ml of DMF and neutralized with 81.2 µl of triethylamine under ice cooling. To the neutralized solution, 136 mg of Boc-Thz-OH, 258 mg of Bop reagent and 162 µl of triethylamine were added and the resultant mixture was stirred for 2 hr. The reaction mixture was treated similarly to that in Example 132 (Process 1) to give 134 mg of the title compound.

TLC: Rf 0.39 (chloroform methanol=20:1)

[Process 3] Boc-(2S,3S)-AHPBA-Thz-Ileol

Deprotection of 134 mg of the compound obtained by the process 2 was performed similarly to that in Example 30 (Process 2), and the obtained product was dissolved in 3 ml of DMF and neutralized with 56 µl of triethylamine under ice cooling. To the neutralized solution, 119 mg of Boc-(2S,3S)-AHPBA-OH, 178 mg of Bop reagent and 112 µl of triethylamine were added and the resultant mixture was stirred for 2 hr. The reaction mixture was treated similarly to that in Example 30 (Process 4) to give 54 mg of the title compound.

TLC: Rf 0.37 (chloroform:methanol=20:1)

[Process 4] Boc-Msa-(2S,3S)-AHPBA-Thz-Ileol

Deprotection of 54 mg of the compound obtained by the process 3 was performed similarly to that in Example 30 (Process 2), and the obtained product was dissolved in 3 ml of DMF and neutralized with 14.7 µl of triethylamine under ice cooling. To the neutralized solution, 29. mg of Boc-Msa-OH, 47 mg of Bop reagent and 29.5 µl of triethylamine were added and the resultant mixture was stirred for 2 hr. The reaction mixture was treated similarly to that in Example 132 (Process 1) to give 22 mg of the title compound.

TLC: Rf 0.18 (chloroform:methanol=20:1)

[Process 5]: 1-Naphthoxyacetyl-Msa-(2S,3S)-AHPBA-Thz-Ileol

Deprotection of 22 mg of the compound obtained by the process 4 was performed similarly to that in Example 30 (Process 2), and the obtained product was dissolved in 3 ml of DMF and neutralized with 4.6 µl of triethylamine under ice cooling. To the neutralized solution, 7 mg of 1-naphthoxyacetic acid, 15 mg of Bop reagent and 9.3 µl of triethylamine were added and the resultant mixture was stirred for 2 hr. The reaction mixture was evaporated under reduced pressure and dissolved in ethyl acetate. The solution was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure to give 45 mg of a crude product. The crude product was dissolved in methanol, fractionated by a reversed-phase HPLC and lyophilized to give 7.9 mg of the title compound.

TLC: Rf 0.41 (chloroform:methanol=20:1)

Analytical HPLC: 21.54 min (For the condition, see: that of example 35)

FAB-MS: 743(M+1)

Example 138

2-Quinolinecarbonyl-Asn-(2S,3S)-AHPBA-Pro-NH-tBu

Deprotection of 18 mg of the compound obtained by Example 80 (Process 2) was performed similarly to that in Example 28 (Process 3), and the obtained product was dissolved in 3 ml of DMF and neutralized with 4.5 µl of triethylamine under ice cooling. To the neutralized solution, 7 mg of 2-quinolinecarboxylic acid, 17 mg of Bop reagent and 9.8 µl of triethylamine were added and the resultant mixture was stirred for 2 hr. The reaction mixture was treated similarly to that in Example 118 to give 6.1 mg of the title compound.

TLC: Rf 0.89 (chloroform:methanol=9:1)

Analytical HPLC: 20.30 min (For the condition, see: that in example 35.)

FAB-MS: 603 (M+1)

Example 139

1-Naphthoxyacetyl-Asp(NHNH$_2$)-(2S,3S)-AHPBA-Pro-NH-tBu.AcOH

[Process 1] Boc-Asp(OBzl)-(2S,3S)-AHPBA-Pro-NH-tBu

Deprotection of 25 mg of the compound obtained by Example 55 (Process 2) was performed similarly to that in Example 28, (Process 3), and the obtained product was dissolved in 3 ml of DMF and neutralized with 7.8 µl of triethylamine under ice cooling. To the neutralized solution, 20 mg of Boc-Asp(OBzl)-OH, 27 mg of Bop reagent and 17.1 µl of triethylamine were added and the resultant mixture was stirred for 2 hr. The reaction mixture was treated similarly to that in Example 132 (Process 1) to give 23 mg of the title compound.

TLC: Rf 0.84 (chloroform:methanol=9:1)

[Process 2] 1-Naphthoxyacetyl-Asp(OBzl)-(2S,3S)-AHPBA-Pro-NH-tBu

Deprotection of 23 mg of the compound obtained by the process 1 was performed similarly to that in Example 28 (Process 3), and the obtained product was dissolved in 3 ml of DMF and neutralized with 4.9 µl of triethylamine under ice cooling. To the neutralized solution, 9 mg of 1-naphthoxyacetic acid, 19 mg of Bop reagent, 11.8 µl of triethylamine and 7 mg of HOBt were added and the resultant mixture was stirred for 2 hr. The reaction mixture was evaporated under reduced pressure and the resultant residue was redissolved in ethyl acetate. The obtained solution was washed with 5% citric acid aqueous solution, 5% sodium hydrogencarbonate aqueous solution and saturated sodium chloride aqueous solution, successively, and dried over anhydrous sodium sulfate. The dried solution was evaporated under reduced pressure to give 24 mg of the title compound.

TLC: Rf 0.86 (chloroform:methanol=9:1)

[Process 3] 1-Naphthoxyacetyl-Asp(NHNH$_2$)-(2S, 3S)-AHPBA-Pro-NH-tBu.AcOH

In 3 ml of methanol, 24 mg of the compound obtained by the process 2 was dissolved and 20 μl of hydrazine hydrate was added and the resultant reaction mixture was stirred for 15 hr. The reaction mixture was evaporated under reduced pressure and the residue was subjected to a silica gel column chromatography (chloroform:methanol=40:1) to give 28 mg of the crude product. In methanol, 10 mg of the crude product was desolved, fractionated by a reverced-phase HPLC [0.1% acetic acid (aq)-acetonitrile], lyophilized to give 2.5 mg of the title compound.

TLC: Rf 0.44 (chloroform:methanol=9:1)

Analytical HPLC: 21.98 min (For the condition, see: Example 35).

FAB-MS: 661 (M+1)

Example 140

1-Isoquinolinecarbonyl-Asn-(2S,3S)-AHPBA-Pro-NH-tBu

Deprotection of 19 mg of the compound obtained by Example 80 (Process 2) was performed similarly to that in example 28 (Process 3), and the obtained product was dissolved in 3 ml of DMF and neutralized with 4.7 μl of triethylamine under ice cooling. To the neutralized solution, 6 mg of 1-isoquinolinecarboxylic acid, 10 mg of Bop reagent and 9.4 μl of triethylamine were added and the resultant mixture was stirred for 2 hr. The reaction mixture was evaporated under reduced pressure and the resultant residue was re-dissolved in ethyl acetate. The obtained solution was washed with 5% sodium hydrogencarbonate aqueous solution and saturated sodium chloride aqueous solution, successively, and dried over anhydrous sodium sulfate. The dried solution was evaporated under reduced pressure and subjected to a silica gel column chromatography (chloroform:methanol=40:1) to give 19 mg of the crude compound. In methanol, 10 mg of the crude compound was dissolved, fractionated by a reversed-phase HPLC [0.1% acetic acid (aq)-acetonitrile system] and lyophilized to give 7.4 mg of the title compound.

TLC: Rf 0.38 (chloroform:methanol=9:1)

Analytical HPLC: 19.33 min (For the condition, see: Example 35.)

FAB-MS: 603 (M+1)

Example 141

1-Naphthalenesulfonyl-Asn-(2S,3S)-AHPBA-Pro-NH-tBu

Deprotection of 21 mg of the compound obtained by Example 80 (Process 2) was performed similarly to that in Example 28 (Process 3), and the obtained product was dissolved in 3 ml of DMF and neutralized with 5.2 μl of triethylamine under ice cooling. To the neutralized solution, 9 mg of 1-naphthalenesulfonyl chloride and 5.7 μl of triethylamine were added and the resultant mixture was stirred for 2 hr. The reaction mixture was treated similarly to that in Example 132 (Process 2) to give 6.7 mg of the title compound.

TLC: Rf 0.42 (chloroform:methanol=9:1)

Analytical HPLC: 22.40 min (For the condition, see: Example 35.)

FAB-MS: 652(M+1)

Example 142

1-Naphthoxyacetyl-Msa-(2S,3S)-AHPBA-Thz-NH-tAmyl

[Process 1] Boc-Thz-NH-tAmyl

In a methylene chloride solution containing 200 mg of Boc-Thz-OH, 100 μl of tert-amylamine and 196 mg of EDC hydrochloride were added and the resultant mixture was stirred for 14 hr. The reaction mixture was treated similarly to that in Example 28 (Process 2) to give 167 mg of the title compound.

TLC: Rf 0.76 (chloroform:methanol=20:1)

[Process 2] Boc-(2S,3S)-AHPBA-Thz-NH-tAmyl

Deprotection of 63 mg of the compound obtained by the process 1 was performed similarly to that in Example 28 (Process 3), and the obntained product was dissolved in 3 ml of DMF and neutralized with 29 μl of triethylamine under ice cooling. To the neutralized solution, 100 mg of Boc-(2S, 3S)-AHPBA-OH.DCHA, 93 mg of Bop reagent, and 29 μl of triethylamine were added and the resultant mixture was stirred for 2 hr. The reaction mixture was treated similarly to that in Example 132 (Process 1) to give 51 mg of the title compound.

TLC: Rf 0.71 (chloroform:methanol=9:1)

[Process 3] Boc-Msa-(2S,3S)-AHPBA-Thz-NH-tAmyl

Deprotection of 51 mg of the compound obtained by the process 2 was performed similarly to that in Example 28 (Process 3), and the obntained product was dissolved in 3 ml of DMF and neutralized with 14.8 μl of triethylamine under ice cooling. To the neutralized solution, 29 mg of Boc-Msa-OH, 47 mg of Bop reagent, and 29.6 μl of triethylamine were added and the resultant mixture was stirred for 2 hr. The reaction mixture was treated similarly to that in Example 132 (Process 1) to give 47 mg of the title compound.

TLC: Rf 0.64 (chloroform:methanol=9:1)

[Process 1] 1-Naphthoxyacetyl-Msa-(2S,3S)-AHPBA-Thz-NH-tAmyl

Deprotection of 47 mg of the compound obtained by the process 3 was performed similarly to that in Example 28 (Process 3), and the obntained product was dissolved in 3 ml of DMF and neutralized with 10.4 μl of triethylamine under ice cooling. To the neutralized solution, 15 mg of 1-naphthoxy acetic acid, 33 mg of Bop reagent, and 20.7 μl of triethylamine were added and the resultant mixture was stirred for 2 hr. The reaction mixture was treated similarly to that in Example 132 (Process 2) to give 6.7 mg of the title compound.

TLC: Rf 0.39 (chloroform:methanol=9:1)

Analytical HPLC: 28.66 min (For the condition, see: Example 35.)

FAB-MS: 713 (M+1)

Example 143

2-Biphenylcarbonyl-Msa-(2S,3S)-AHPBA-Thz-NH-tBu

Deprotection of 146 mg of the compound obtained by Example 100 (Process 1) was performed similarly to that in Example 28 (Process 3), and the obntained product was dissolved in 3 ml of DMF and neutralized with 33 μl of triethylamine under ice cooling. To the neutralized solution, 47 mg of 2-biphenylcarboxylic acid, 105 mg of Bop reagent, and 65.9 μl of triethylamine were added and the resultant mixture was stirred for 2 hr. The reaction mixture was treated similarly to that in Example 132 (Process 1) to give 102 mg of the crude compound. The crude compound was dissolved in methanol and subjected to a reversed-phase HPLC (water-acetonitrile system), fractionated, purified and lyophilized to give the title compound.

TLC: Rf 0.64 (chloroform:methanol=9:1)

Analytical HFLC: 23.30 min (For the condition, see: Example 35.)

FAB-MS: 696 (M+1)

Example 144

1-Nachthoxyacetyl-Msa-(2S,3S)-AHPBA-3Dic-NH-tBu

[Process 1] Boc-(DL)-3Dic-OH

In an ethanol solution containing 2.0 g of N-(tert-butoxycarbonyl)-DL-1,2,3,4-tetrahydroisoquinoline-3-carboxylic acid, 5% $Rh/Al_2O_3$ was added and the resultant mixture was stirred for 3 days in a hydrogen gas atmosphere (4.5 $kg/cm^2$). The reaction mixture was filtered and the filtrate was evaporated under reduced pressure. The resultant residue was crystallized by the treatment with ether-hexane to give 1.5 g of the title compound.

TLC: Rf 0.56 (chloroform:methanol:acetic acid 9:1:0.5)

[Process 2] Boc-(DL)-3Dic-NH-tBu

In a dichloromethane solution containing 0.2 g of the protected amino acid obtained by the process 1, 60 mg of tert-butylamine and 0.12 g of HOBt and 0.16 g of EDC hydrochloride were added under ice-cooling and the resultant mixture was stirred overnight at room temperature. The reaction mixture was evaporated under reduced pressure and the resultant residue was re-dissolved in ethyl acetate. The obtained solution was washed with 5% sodium hydrogencarbonate aqueous solution, 10% citric acid aqueous solution and saturated sodium chloride aqueous solution, successively, and dried over anhydrous sodium sulfate. The dried solution was evaporated under reduced pressure and crystallized from ether-hexane to give 0.21 g of the title compound.

TLC: Rf 0.88 (chloroform:methanol:acetic acid=9:1:0.5)

[Process 3] Boc-(2S,3S)-AHPBA-(DL)-3Dic-NH-tBu

Deprotection of 210 mg of the compound obtained by the process 2 was performed similarly to that in Example 28 (Process 3), and the obntained product was dissolved in dichloromethane and neutralized with 90 μl of triethylamine under ice cooling. To the neutralized solution, 0.18 g of Boc-(2S,3S)-AHPBA-OH and 0.33 g of Bop reagent were added and the resultant mixture was stirred overnight at room temperature. The reaction mixture was treated similarly to that in the process 2 to give 150 mg of the title compound.

TLC: Rf 0.63 (chloroform:methanol=40:1)

[Process 4] Boc-Msa-(2S,3S)-AHPBA-(DL)-3Dic-NH-tBu

Deprotection of 150 mg of the compound obtained by the process 3 was performed similarly to that in Example 28 (Process 3), and the obntained product was dissolved in DMF and neutralized with 40 μl of triethylamine under ice cooling. To the neutralized solution, 72 mg of Boc-Msa-OH and 146 mg of Bop reagent were added and the resultant mixture was stirred overnight at room temperature. The reaction mixture was treated similarly to that in the process 2 to give 0.11 g of the title compound.

TLC: Rf 0.76 (chloroform:methanol:acetic acid=9:1:0.5)

[Process 5] 1-Naphthoxyacetyl-Msa-(2S,3S)-AHPBA-3Dic-NH-tBu

Deprotection of 110 mg of the compound obtained by the process 4 was performed similarly to that in Example 125 (Process 2), and the obntained product was dissolved in DMF and neutralized with 20 μl of triethylamine under ice cooling. To the neutralized solution, 30 mg of 1-naphthoxyacetic acid and 60 mg of Bop reagent were added and the resultant mixture was stirred overnight at room temperature. The reaction mixture was treated similarly to that in Example 122 to give 8 mg of the title compound.

FAB-MS: 749 (M+1)

Example 145

1-Naphthoxyacetyl-Msa-(2S,3S)-AHPBA-1Dic-NH-tBu

[Process 1] Boc-(DL)-1Dic-OH

In an acetic acid solution containing 2.0 g of isoquinoline-1-carboxylic acid, 5% $Rh/Al_2O_3$ was added and the resultant mixture was stirred for 3 days in a hydrogen gas atmosphere (4.5 $kg/cm^2$). The reaction mixture was filtered and the filtrate was evaporated under reduced pressure. The resultant residue was tert-butoxycarbonylated, dissolved in ethanol, and the resultant mixture was stirred with 5% $Rh/Al_2O_3$ for 3 days in a hydrogen gas atmosphere (4.5 $kg/cm^2$). The reaction mixture was treated similarly to that in Example 144 (Process 1) to give 0.8 g of the title compound.

TLC: Rf 0.71 (chloroform:methanol:acetic acid 9:1:0.5)

[Process 2] Boc-(DL)-1Dic-NH-tBu

In a dichloromethane solution containing 0.29 g of the protected amino acid obtained by the process 1, 90 mg of tert-butylamine and 0.17 g of HOBt and 0.23 g of EDC hydrochloride were added under ice cooling and the resultant mixture was stirred overnight at room temperature. The reaction mixture was treated similarly to that in Example 144 (Process 2) to give 0.13 g of the title compound.

TLC: Rf 0.76 (chloroform:methanol:acetic acid=9:1:0.5)

[Process 3] Boc-(2S,3S)-AHPBA-(DL)-1Dic-NH-tBu

Deprotection of 130 mg of the compound obtained by the process 2 was performed similarly to that in Example 28 (Process 3), and the obntained product was dissolved in dichloromethane and neutralized with 50 μl of triethylamine under ice cooling. To the neutralized solution, 0.1 g of Boc-(2S,3S)-AHPBA-OH and 0.18 g of Bop reagent were added and the resultant mixture was stirred overnight at room temperature. The reaction mixture was treated similarly to that in Example 144 (Process 2)to give 90 mg of the title compound.

TLC: Rf 0.68 (chloroform:methanol=40:1)

[Process 4] Boc-Msa-(2S,3S)-AHPBA-(DL)-1Dic-NH-tBu

Deprotection of 90 mg of the compound obtained by the process 3 was performed similarly to that in Example 28

(Process 3), and the obntained product was dissolved in DMF and neutralized with 20 μl of triethylamine under ice cooling. To the neutralized solution, 42 mg of Boc-Msa-OH and 80 mg of Bop reagent were added and the resultant mixture was stirred overnight at room temperature. The reaction mixture was treated similarly to that in Example 144 (Process 2) to give 90 mg of the title compound.

TLC: Rf 0.83 (chloroform:methanol:acetic acid=9:1:0.5)

[Process 5] 1-Naphthoxyacetyl-Msa-(2S,3S)-AHPBA-1Dic-NH-tBu

Deprotection of 90 mg of the compound obtained by the process 4 was performed similarly to that in Example 125 (Process 2), and the obntained product was dissolved in DMF and neutralized with 35 μl of triethylamine under ice cooling. To the neutralized solution, 30 mg go 1-naphthoxyacetic acid and 60 mg of Bop reagent were added and the resultant mixture was stirred overnight at room temperature. The reaction mixture was treated similarly to that in Example 122 to give 3 mg of the title compound.

FAB-MS: 749 (M+1)

Example 146

1-Naphthoxyacetyl-Msa-(2S,3S)-AHPBA-Oic-NH-tBu

[Process 1] Boc-Oic-OH

In an acetic acid solution containing 2.0 g of L-indoline-2-carboxylic acid, 5% Rh/Al$_2$O$_3$ was added and the resultant mixture was stirred for 3 days in a hydrogen gas atmosphere (4.5 kg/cm$^2$). The reaction mixture was filtered and the filtrate was evaporated under reduced pressure. The resultant residue was tert-butoxycarbonylated to give 0.6 g of the title compound.

[Process 2] Boc-Oic-NH-tBu

In a dichloromethane solution containing the protected amino acid obtained by the process 1, tert-butylamine, HOBt and EDC hydrochloride were added under ice cooling and the resultant mixture was stirred overnight at room temperature. The reaction mixture was treated similarly to that in Example 144 (Process 2) to give the title compound.

TLC: Rf 0.89 (chloroform:methanol=9:1)

[Process 3] Boc-(2S,3S)-AHPBA-Oic-NH-tBu

Deprotection of 63 mg of the compound obtained by the process 2 was performed similarly to that in Example 28 (Process 3), and the obntained product was dissolved in dichloromethane and neutralized with 20 μl of triethylamine under ice cooling. To the neutralized solution, 86 mg of Boc-(2S,3S)-AHPBA-OH and 93 mg of Bop reagent were added and the resultant mixture was stirred overnight at room temperature. The reaction mixture was treated similarly to that in Example 144 (Process 2) to give 10 mg of the title compound.

TLC: Rf 0.35 (hexane:ether 2:1)

[Process 4] Boc-Msa-(2S,3S)-AHPBA-Oic-NH-tBu

Deprotection of 10 mg of the compound obtained by the process 3 was performed similarly to that in Example 28 (Process 3), and the obntained product was dissolved in DMF and neutralized with 3 μl of triethylamine under ice cooling. To the neutralized solution, 10 mg of Boc-Msa-OH and 12 mg of Bop reagent were added under ice cooling and the resultant mixture was stirred overnight at room temperature. The reaction mixture was treated similarly to that in Example 46 to give 20 mg of the title compound.

TLC: Rf 0.76 (chloroform:methanol=9:1)

[Process 5] 1-Naphthoxyacetyl-Msa-(2S,3S)-AHPBA-Oic-NH-tBu

Deprotection of 20 mg of the compound obtained by the process 4 was performed similarly to that in Example 125 (Process 2), and the obntained product was dissolved in DMF and neutralized with 3 μl of triethylamine under ice cooling. To the neutralized solution, 4 mg of 1-naphthoxyacetic acid and 11 mg of Bop reagent were added and the resultant mixture was stirred overnight at room temperature. The reaction mixture was treated similarly to that in Example 122 to give 1 mg of the title compound. Analytical HPLC: 27.47 min (For the condition, see: Example 35.)

FAB-MS: 735 (M+1)

Example 147

1-Naphthoxyacetyl-Msa-(2S,3S)-AHPBA-Pro-NH-Ph(o-OH)

[Process 1] Boc-Pro-NH-Ph(o-OH)

In a dichloromethane solution containing 1.07 g of Boc-Pro-OH, 0.55 g of o-aminophenol, 0.84 g of HOBt and 1.15 g of EDC hydrochloride were added under ice cooling and the resultant mixture was stirred overnight at room temperature. The reaction mixture was treated similarly to that in Example 144 (Process 2) to give 0.25 g of the title compound.

TLC: Rf 0.60 (chloroform:methanol=9:1)

[Process 2] Boc-(2S,3S)-AHPBA-Pro-NH-Ph(o-OH)

Deprotection of 100 mg of the compound obtained by the process 1 was performed similarly to that in Example 28 (Process 3), and the obtained product was dissolved in dichloromethane and neutralized with 50 μl of triethylamine under ice cooling. To the neutralized solution, 155 mg g of Boc-(2S,3S)-AHPBA-OH and 175 mg of Bop reagent were added and the resultant mixture was stirred overnight at room temperature. The reaction mixture was treated similarly to that in Example 55 (Process 3) to give 70 mg of the title compound.

TLC: Rf 0.51 (chloroform:methanol=9:1)

[Process 3] Boc-Msa-(2S,3S)-AHPBA-Pro-NH-Ph(o-OH)

Deprotection of 50 mg of the compound obtained by the process 2 was performed similarly to that in Example 28 (Process 3), and the obntained product was dissolved in DMF and neutralized with 14 μl of triethylamine under ice cooling. To the neutralized solution, 27 mg of Boc-Msa-OH and 53 mg of Bop reagent were added and the resultant mixture was stirred overnight at room temperature. The reaction mixture was treated similarly to that in Example 93 (Process 3) to give 20 mg of the title compound.

TLC: Rf 0.53 (chloroform:methanol=9:1)

[Process 4] 1-Naphthoxyacetyl-Msa-(2S,3S)-AHPBA-Pro-NH-Ph(o-OH)

Deprotection of 20 mg of the compound obtained by the process 3 was performed similarly to that in Example 125

(Process 2), and the obntained product was dissolved in DMF and neutralized with 4.2 µl of triethylamine under ice cooling. To the neutralized solution, 6 mg of 1-naphthoxyacetic acid and 18 mg of Bop reagent were added and the resultant mixture was stirred overnight at room temperature. The reaction mixture was treated similarly to that in Example 122 to give 6 mg of the title compound. Analytical HPLC: 25.83 min (For the condition, see: Example 35.)

FAB-MS: 717 (M+1)

Example 148

1-Naphthoxyacetyl-Msa-(2S,3S2-AHPBA-Pro-NH-Ph(m-OH)

[Process 1] Boc-Pro-NH-Ph(m-OH)

From 1.07 g of Boc-Pro-OH, and 0.55 g of m-aminophenol, 0.13 g of the title compound was synthesized by the similar method to Example 147 (Process 1).

TLC: Rf 0.54 (chloroform:methanol=9:1)

[Process 2] Boc-(2S,3S)-AHPBA-Pro-NH-Ph(m-OH)

From 0.13 g of the protected amino acid obtained by the process 1, 114 mg of the title compound was systhesized by the similar method to Example 147 (Process 2).

TLC: Rf 0.38 (chloroform:methanol=9:1)

[Process 3] Boc-Msa-(2S,3S)-AHPBA-Pro-NH-Ph(m-OH)

From 50 mg of the protected peptide obtained by the process 2, 60 mg of the title compound was synthesized by the similar method to Example 147 (Process 3)

TLC: Rf 0.45 (chloroform:methanol=9:1)

[Process 4] 1-Naphthoxyacetyl-Msa-(2S,3S)-AHPBA-Pro-NH-Ph(m-OH)

From 60 mg of the protected peptide obtained by the process 3, 5 mg of the title compound was synthesized by the similar method to Example 147 (Process 3).

Analytical HPLC: 24.23 min (For the condition, see: Example 35.)

FAB-MS: 717 (M+1)

Example 149

1-Naphthoxyacetyl-Msa-(2S,3S)-AHPBA-Pro-NH-Ph(p-OH)

[Process 1] Boc-Pro-NH-Ph(p-OH)

From 1.07 g of Boc-Pro-OH and 0.55 g of p-aminophenol, 0.13 g of the title compound was synthesized by the similar method to Example 147 (Process 1)

TLC: Rf 0.72 (chloroform:methanol:$H_2O$=8:3:1, lower layer)

[Process 2] Boc-(2S,3S)-AHPBA-Pro-NH-Ph(p-OH)

From 0.1 g of the protected amino acid obtained by the process 1, 151 mg of the title compound was synthesized by the similar method to Example 147 (Process 2)

TLC: Rf 0.50 (chloroform:methanol=9:1)

[Process 3] Boc-Msa-(2S,3S)-AHPBA-Pro-NH-Ph(p-OH)

From 50 mg of the protected peptide obtained by the process 2, 10 mg of the title compound was synthesized by the similar method to Example 147 (Process 3)

TLC: Rf 0.45 (chloroform:methanol=9:1)

[Process 4] 1-Naphthoxyacetyl-Msa-(2S,3S)-AHPBA-Pro-NH-Ph(p-OH)

From 10 mg of the protected peptide obtained by the process 3, 1 mg of the title compound was synthesized by the similar method to Example 147 (Process 4).

Analytical HPLC: 24.83 min (For the condition, see: Example 35.)

FAB-MS: 717 (M+1)

Example 150

1-Naphthoxyacetyl-Msa-(2S,3S)-AHPBA-Hyp-NH-tBu

[Process 1] Boc-Hyp-NH-tBu

In a dichloromethane solution containing 5.1 g of N-Boc-hydroxyproline (Boc-Hyp-OH), 0.35 g of tert-butylamine, 7.4 g of HOBt and 6.0 g of EDC hydrochloride were added under ice cooling and the resultant mixture was stirred overnight at room temperature. The reaction mixture was treated similarly to that in Example 144 (Process 2) to give 2.59 g of the title compound.

TLC: Rf 0.67 (chloroform:methanol=9:1)

[Process 2] Boc-(2S,3S)-AHPBA-Hyp-NH-tBu

Deprotection of 170 mg of the compound obtained by the process 1 was performed similarly to that in Example 125 (Process 2), and the obntained product was dissolved in dichloromethane and neutralized with 50 µl of triethylamine under ice cooling. To the neutralized solution, 138 mg of Boc-(2S,3S)-AHPBA-OH and 200 mg of Bop reagent were added and the resultant mixture was stirred overnight at room temperature. The reaction mixture was treated similarly to that in Example 144 (Process 2) to give 0.13 g of the title compound.

TLC: Rf 0.41 (chloroform:methanol=9:1)

[Process 3] Boc-Msa-(2S,3S)-AHPBA-Hyp-NH-tBu

Deprotection of 100 mg of the compound obtained by the process 2 was performed similarly to that in Example 125 (Process 2), and the obntained product was dissolved in DMF and neutralized with 30 µl of triethylamine under ice cooling. To the neutralized solution, 59 mg of Boc-Msa-OH and 116 mg of Bop reagent were added and the resultant mixture was stirred overnight at room temperature. The reaction mixture was treated similarly to that in Example 93 (Process 3) to give 33 mg of the title compound.

TLC: Rf 0.18 (chloroform:methanol=9:1)

[Process 4] 1-Naphthoxyacetyl-Msa-(2S,3S)-AHPBA-Hyp-NH-tBu

Deprotection of 20 mg of the compound obtained by the process 3 was performed similarly to that in Example 125 (Process 2), and the obntained product was dissolved in DMF and neutralized with 4 µl of triethylamine under ice cooling. To the neutralized solution, 6 mg of 1-naphthoxyacetic acid and 18 mg of Bop reagent were added and the resultant mixture was stirred overnight at room temperature. The reaction mixture was treated similarly to that in Example 122 to give 1 mg of the title compound.

Analytical HPLC: 26.27 min (For the condition, see: Example 35.)

FAB-MS: 697 (M+1)

Example 151

1-Naphthoxyacetyl-Msa-(2S,3S)-AHPBA-Hyp(Me)-NH-tBu

[Process 1] Boc-Hyp(Me)-NH-tBu

In a THF solution containing 0.6 g of the protected amino acid obtained by the Example 150, (Process 1), 94 mg of sodium hydride (60% in oil) was added under ice cooling and the resultant mixture was stirred for 1 hr at room temperature. Further, 2.0 ml of methyl iodide was added and the obtained reaction mixture was stirred for 3 hr at from temperature. To the reaction mixture, 5% potassium hydrogensulfate aqueous solution was added and extracted with ethyl acetate. The organic layer was washed with water and saturated sodium chloride aqueous solutions successively and dried over anhydrous sodium sulfate. The dried solution was evaporated under reduced pressure and treated with hexane to crystallize 0.4 g of the title compound.

TLC: Rf 0.74 (chloroform:methanol=9:1)

[Process 2] Boc-(2S,3S)-AHPBA-Hyp(Me)-NH-tBu

From 0.1 g of the protected amino acid obtained by the process 1, 0.14 g of the title compound was synthesized by the similar method to Example 150 (Process 2).

TLC: Rf 0.62 (chloroform:methanol=9:1)

[Process 3] Boc-Msa-(2S,3S)-AHPBA-Hyp(Me)-NH-tBu

From 0.14 g of the protected peptide obtained by the process 2, 0.14 g of the title compound was synthesized by the similar method to Example 150 (Process 3).

TLC: Rf 0.76 (chloroform:methanol=9:1)

[Process 4] 1-Naphthoxyacetyl-Msa-(2S,3S)-AHPBA-Hyp(Me)-NH-tBu

From 20 mg of the protected peptide obtained by the process 3, 11 mg of the title compound was synthesized by the similar method to Example 150 (Process 4).

Analytical HPLC: 26.43 min (For the condition, see: Example 35.)

FAB-MS: 711 (M+1)

Example 152

1-Naphthoxyacetyl-Msa-(2S,3S)-AHPBA-Hyp(Et)-NH-tBu

[Process 1] Boc-Hyp(Et)-NH-tBu

In a THF solution containing 1.0 g of the protected amino acid obtained by the Example 150 (Process 1), 160 mg of sodium hydride (60% in oil) was added under ice cooling and the resultant mixture was stirred for 1 hr at room temperature. Further, 1 ml of ethyl bromide was added and stirred for 3 hr at room temperature. the obtained reaction mixture was treated similarly to that in Example 151 (Process 1) to give 0.8 g of the title compound.

TLC: Rf 0.78 (chloroform:methanol=9:1)

[Process 2] Boc-(2S,3S)-AHPBA-Hyp(Et)-NH-tBu

From 0.8 g of the protected amino acid obtained by the process 1, 80 mg of the title compound was synthesized by the similar method to Example 150 (Process 2).

TLC: Rf 0.70 (chloroform:methanol=9:1)

[Process 3] Boc-Msa-(2S,3S)-AHPBA-Hyp(Et)-NH-tBu

From 80 mg of the protected peptide obtained by the process 2, 87 mg of the title compound was synthesized by the similar method to Example 150 (Process 3).

TLC: Rf 0.76 (chloroform:methanol=9:1)

[Process 4] 1-Naphthoxyacetyl-Msa-(2S,3S)-AHPBA-Hyp(Et)-NH-tBu

From 20 mg of the protected peptide obtained by the process 3, 2 mg of the title compound was synthesized by the similar method to Example 150 (Process 4).

Analytical HPLC: 27.42 min (For the condition, see: Example 35.)

FAB-MS: 725 (M+1)

Example 153

1-Naphthoxyacetyl-Msa-(2S,3S)-AHPBA-Hyp(Allyl)-NH-tBu

[Process 1] Boc-Hyo(Allyl)-NH-tBu

In a THF solution containing 1.0 g of the protected amino acid obtained by the Example 150 (Process 1), 160 mg of sodium hydride (60% in oil) was added under ice cooling and the resultant mixture was stirred for 1 hr at room temperature. Further, 0.5 ml of allyl bromide was added and stirred for 3 hr at room temperature. the obtained reaction mixture was treated similarly to that in Example 151 (Process 1) to give 0.95 g of the title compound.

TLC: Rf 0.87 (chloroform:methanol=9:1)

[Process 2] Boc-(2S,3S)-AHPBA-Hyo(Allyl)-NH-tBu

From 0.13 g of the protected amino acid obtained by the process 1, 156 mg of the title compound was synthesized by the similar method to Example 150 (Process 2).

TLC: Rf 0.82 (chloroform:methanol=9:1)

[Process 3] Boc-Msa-(2S,3S)-AHPBA-Hyp(Allyl)-NH-tBu

From 50 mg of the protected peptide obtained by the process 2, 41 mg of the title compound was synthesized by the similar method to Example 150 (Process 3).

TLC: Rf 0.59 (chloroform:methanol=9:1)

[Process 4] 1-Naphthoxyacetyl-Msa-(2S,3S)-AHPBA-Hyp(Allyl)-NH-tBu

From 21 mg of the protected peptide obtained by the process 3, 4 mg of the title compound was synthesized by the similar method to Example 150 (Process 4).

Analytical HPLC: 28.27 min (For the condition, see: Example 35.)

FAB-MS: 737 (M+1)

Example 154

1-Naphthoxyacetyl-Mtv-(2S,3S)-AHPBA-Thz-NH-tBu

[Process 1] N-Boc-β-(methylthio)valine [Boc-Mtv-OH]

In 70 ml of a mixture of 1N-NaOH-ethanol (1:1) solution containing 1.04 g of L-penicillamine, 0.48 ml of methyl iodide was added under ice cooling and the obtained reaction mixture was stirred overnight at room temperature. The reaction mixture was evaporated under reduced pressure and the resultant residue was redissolved in ethyl acetate, washed with 5% sodium hydrogensulfite aqueous solution and saturated sodium chloride aqueous solution, successively, and dried over anhydrous sodium sulfate. The dried solution was evaporated under reduced pressure. The obtained residue was tert-butoxycarbonylated and 2.83 g of the title compound was obtained as its DCHA salt.

TLC: Rf 0.68 (chloroform:methanol:$H_2O$=8:3:1, lower layer)

[Process 2] Boc-Mtv-(2S,3S)-AHPBA-Thz-NH-tBu

Deprotection of 50 mg of the compound obtained by Example 82 (Process 2) was performed similarly to that in Exarmple 125 (Process 2), and the obtained product was dissolved in DMF and neutralized with 14 μl of triethylamine under ice cooling. To the neutralized solution, 45 mg of the protected amino acid DCHA salt obtained by the process 1 and 53 mg of Bop reagent were added and the resultant mixture was stirred overnight at room temperature. The reaction mixture was treated similarly to that in Example 144 (Process 2) to give 30 mg of the title compound.

TLC: Rf 0.86 (chloroform:methanol=9:1)

[Process 3] 1-Naphthoxyacetyl-Mtv-AHPBA-Thz-NH-tBu

Deprotection of 30 mg of the compound obtained by the process 2 was performed similarly to that in Example 125 (Process 2), and the obtained product was dissolved in DMF and neutralized with 7 μl of triethylamine under ice cooling. To the neutralized solution, 10 mg of 1-naphthoxyacetic acid and 26 mg of Bop reagent were added and the resultant mixture was stirred overnight at room temperature. The reaction mixture was treated similarly to that in Example 122 to give 1 mg of the title compound.

Analytical HPLC: 33.23 min (For the condition, see: Example 35.)

FAB-MS: 695 (M+1)

Example 155

1-Naphtboxyacetyl-Msv-(2S,3S)-AHPBA-Thz-NH-tBu

[Process 1] Boc-β-(methanesulfonyl)valine [Boc-Msv-OH]

In a chloroform solution containing 0.44 g of the protected amino acid obtained by the Example 154, (Process 1), 0.52 g of m-chloroperbenzoic acid was added under ice cooling and the reaction mixture was stirred for 2 hr at room temperature. The reaction mixture was mixed with methyl sulfide and filtered. DCHA was added to the filtrate, and the solution was evaporated under reduced pressure and crystallized by the addition of ether-hexane. The obtained solid was recrystallized from ether-hexane to give 0.23 g of the title compound as its DCHA salt.

TLC: Rf 0.33 (chloroform:methanol=9:1)

[Process 2] Boc-Msv-(2S,3S)-AHPBA-Thz-NH-tBu

Deprotection of 50 mg of the compound obtained by Example 82 (Process 2) was performed similarly to that in Example 125 (Process 2), and the obtained product was dissolved in DMF and neutralized with 14 μl of triethylamine, 30 mg of the protected amino acid obtained by the process 1 and 53 mg of Bop reagent were added and the resultant mixture was stirred overnight at room temperature. The reaction mixture was treated similarly to that in Example 144 (Process 2) to give 20 mg of the title compound.

TLC: Rf 0.50 (chloroform:methanol=9:1)

[Process 3] 1-Naphthoxyacetyl-Msv-(2S,3S)-AHPBA-Thz-NH-tBu

Deprotection of 20 mg of the compound obtained by the process 2 was performed similarly to that in Example 125 (Process 2), and the obtained product was dissolved in DMF and neutralized with 4 μl of triethylamine under ice cooling. To the neutralized solution, 6 mg of 1-naphthoxyacetic acid and 18 mg of Bop reagent were added under ice cooling and the resultant mixture was stirred overnight at room temperature. The reaction mixture was treated similarly to that in Example 122 to give 0.3 mg of the title compound.

Analytical HPLC: 28.96 min (ror the condition, see: Example 35.)

FAB-MS: 727 (M+1)

Example 156

1-Naphthoxyacetyl-Msa-(2S,3S)-AHPBA-Thz-NH—CH($C_6H_5$)$CH_2$OH

[Process 1] N-Boc-Phenylglycinol [Boc-Phgol]

In a THF solution containing 0.30 g of lithium borohydride, 1.30 g of N-(tert-butoxycarbonyl) phenylglycine methyl ester was added under ice cooling. To the resultant solution, methanol was added dropwise under ice cooling and stirred overnight at room temperature. Water was added to the reaction mixture, extracted with ethyl acetate. The organic layer was washed with water and saturated sodium chloride aqueous solution, successively, and dried over anhydrous sodium sulfate. The dried solution was evaporated under reduced pressure and the obtained residue was subjected to a silica gel column chromatography (hexane:ether=1:1) to give 0.41 g of the title compound.

TLC: Rf 0.11 (hexane:ether=1:1)

[Process 2] Boc-Thz-Phgol

Deprotection of 240 mg of the compound obtained by the process 1 was performed similarly to that in Example 125 (Process 2), and the obtained product was dissolved in dichloromethane and 0.14 ml of triethylamine, 0.23 g of Boc-Thz-OH, 0.17 g of HOBt and 0.23 g of EDC hydrochloride were added under ice cooling and the resultant mixture was stirred overnight at room temperature. The reaction mixture was treated similarly to that in Example 144 (Process 2) to give 0.15 g of the title compound.

TLC: Rf 0.53 (chloroform:methanol=9:1)

[Process 3] Boc-(2S,3S)-AHPBA-Thz-Phgol

Deprotection of 35 mg of the compound obtained by the process 2 was performed similarly to that in Example 125 (Process 2), and the obtained product was dissolved in DMF and neutralized with 14 a 1 of triethylamine under ice cooling. To the neutralized solution, 30 mg of Boc-(2S,3S)-AHPBA-OH, 53 mg of Bop reagent were added and the resultant mixture was stirred overnight at room temperature. The reaction mixture was treated similarly to that in Example 144 (Process 2) to give 40 mg of the title compound.

TLC: Rf 0.48 (chloroform:methanol=9:1)

[Process 4] Boc-Msa-(2S,3S)-AHPBA-Thz-Phgol

Deprotection of 40 mg of the compound obtained by the process 3 was performed similarly to that in Example 125 (Process 2), and the obtained product was dissolved in DMF and neutralized with 11 µl of triethylamine under ice cooling. To the neutralized solution, 20 mg of Boc-Msa-OH, 40 mg of Bop reagent were added and the resultant mixture was stirred overnight at room temperature. The reaction mixture was treated similarly to that in Example 93 (Process 3) to give 10 mg of the title compound.

TLC: Rf 0.43 (chloroform:methanol=9:1)

[Process 5] 1-Naphthoxyacetyl-Msa-(2S,3S)-AHPBA-Thz-NH—CH($C_6H_5$)$CH_2$OH

Deprotection of 10 mg of the compound obtained by the process 4 was performed similarly to that in Example 125 (Process 2), and the obtained product was dissolved in DMF and neutralized with 1.5 µl of triethylamine under ice cooling. To the neutralized solution, 3 mg of 1-naphthoxyacetic acid and 12 mg of Bop reagent were added and the resultant mixture was stirred overnight at room temperature. The reaction mixture was treated similarly to that in Example 122 to give 0.3 mg of the title compound.

Analytical HPLC: 26.03 min (For the condition, see: Example 35.)

FAB-MS: 763 (M+1)

Example 157

1-Naphthoxyacetyl-Msa-(2S,3S)-AHPBA-Thz-Phr-$NH_2$

[Process 1] Boc-Phz-$NH_2$

In a dichloromethane solution containing 4.3 g of N-(tert-butoxycarbonyl)phenylglycine, 5 ml of ammonia water, 1.5 g of HOBt and 2.3 g of EDC hydrochloride were added under ice cooling and the resultant mixture was stirred overnight at room temperature. The reaction mixture was treated similarly to that in Example 144 (Process 2) to give 0.42 g of the title compound.

TLC: Rf 0.73 (chloroform:methanol=5:1)

[Process 2] Boc-Thz-Phz-$NH_2$

Deprotection of 250 mg of the compound obtained by the process 1 was performed similarly to that in Example 28 (Process 3), and the obtained product was dissolved in dichloromethane and 0.14 ml of triethylamine, 0.23 g of Boc-Thz-OH, 0.17 g of HOBt and 0.23 g of EDC hydrochloride were added and the resultant mixture was stirred overnight at room temperature. The reaction mixture was treated similarly to that in Example 144 (Process 2) to give 0.316 g of the title compound.

TLC: Rf 0.61 (chloroform:methanol=9:1)

[Process 3] Boc-(2S,3S)-AHPBA-Thz-Ph-$NH_2$

Deprotection of 37 mg of the compound obtained by the process 2 was performed similarly to that in Example 28 (Process 3), and the obtained product was dissolved in DMF and neutralized with 14 µl of triethylamine under ice cooling. To the neutralized solution, 30 mg of Boc-(2S,3S)-AHPBA-OH, 53 mg of Bop reagent were added and the resultant mixture was stirred overnight at room temperature. The reaction mixture was treated similarly to that in Example 144 (Process 2) to give 30 mg of the title compound.

TLC: Rf 0.58 (chloroform:methanol=9:1)

[Process 4] Boc-Msa-(2S,3S)-AHPBA-Thz-Phg-$NH_2$

Deprotection of 30 mg of the compound obtained by the process 3 was performed similarly to that in Example 125 (Process 2), and the obtained product was dissolved in DMF and neutralized with 8.4 µl of triethylamine under ice cooling. To the neutralized solution, 16 mg of Boc-Msa-OH, 32 mg of Bop reagent were added and the resultant mixture was stirred overnight at room temperature. The reaction mixture was treated similarly to that in Example 144 (Process 2) to give 30 mg of the title compound.

TLC: Rf 0.47 (chloroform:methanol=9:1)

[Process 5] 1-Naphthoxyacetyl-Msa-(2S,3S)-AHPBA-Thz-Phg-$NH_2$

Deprotection of 30 mg of the compound obtained by the process 4 was performed similarly to that in Example 125 (Process 3), and the obtained product was dissolved in DMF and neutralized with 6 µl of triethylamine under ice cooling. To the neutralized solution, 9 mg of 1-naphthoxyacetic acid and 23 mg of Bop reagent were added and the resultant mixture was stirred overnight at room temperature. The reaction mixture was treated similarly to that in Example 122 to give 2 mg of the title compound.

Analytical HPLC: 23.79 min (For the condition, see: Example 35.)

FAB-MS: 776 (M+1)

Example 158

1-Naphthoxyacetyl-Msa-(2S,3S)-AHPBA-Thz-NH-chex-ol

[Process 1] Boc-Thz-NH-chex-ol

In a dichloromethane solution containing 0.23 g of Boc-Thz-OH, 0.12 g of trans-4-aminocyclohexanol, 0.17 g of HOBt and 0.23 g of EDC hydrochloride were added under ice cooling and the resultant mixture was stirred overnight at room temperature. The reaction mixture was treated similarly to that in Example 144 (Process 2) to give 0.12 g of the title compound.

TLC: Rf 0.38 (chloroform:methanol=9:1)

[Process 2] Boc-(2S,3S)-AHPBA-Thz-NH-chex-ol

Deprotection of 100 mg of the compound obtained by the process 1 was performed similarly to that in Example 28

(Process 3), and the obtained product was dissolved in DMF and neutralized with 56 µl of triethylamine. To the neutralized solution, 190 mg of Boc-(2S,3S)-AHPBA-OH and 221 mg of Bop reagent were added and the resultant mixture was stirred overnight at room temperature. The reaction mixture was treated similarly to that in Example 144 (Process 2) to give 120 mg of the title compound.

TLC: Rf 0.48 (chloroform:methanol=9:1)

[Process 3] Boc-Msa-(2S,3S)-AHPBA-Thz-NH-chex-ol

Deprotection of 50 mg of the compound obtained by the process 2 was performed similarly to that in Example 125 (Process 2), and the obtained product was dissolved in DMF and neutralized with 14 µl of triethylamine under ice cooling. To the neutralized solution, 27 mg of Boc-Msa-OH and 53 mg of Bop reagent were added and the resultant mixture was stirred overnight at room temperature. The reaction mixture was treated similarly to that in Example 93 (Process 3) to give 10 mg of the title compound.

TLC: Rf 0.56 (chloroform:methanol=9:1)

[Process 4] 1-Naphthoxyacetyl-Msa-(2S,3S)-AHPBA-Thz-NH-chex-OH

Deprotection of 10 mg of the compound obtained by the process 3 was performed similarly to that in Example 125 (Process 2), and the obtained product was dissolved in DMF and neutralized with 2 µl of triethylamine under ice cooling. To the neutralized solution, 3 mg of 1-naphthoxyacetic acid and 12 mg of Bop reagent were added and the resultant mixture was stirred overnight at room temperature. The reaction mixture was treated similarly to that in Example 122 to give 2 mg of the title compound. Analytical HPLC: 25.58 min (For the condition, see: Example 35)

FAB-MS: 741 (M+1)

Example 159

1-Naphthoxyacetyl-Msa-(2S,3S)-AHPBA-Thz-Pip-O—CH$_3$

[Process 1] Boc-Thz-(DL)-Pip-O—CH$_3$

In a dichloromethane solution containing 0.20 g of hydrochloride of methyl (DL)-pipecolinate, 0.17 ml of triethylamine, 0.28 g of Boc-Thz-OH, 0.20 g of HOBt and 0.28 g of EDC hydrochloride were added under ice cooling and the resultant mixture was stirred overnight at room temperature. The reaction mixture was treated similarly to that in Example 139 (Process 2) to give 0.34 g of the title compound as oil.

TLC: Rf 0.83 (chloroform:methanol=9:1)

[Process 2] Boc-(2S,3S)-AHPBA-(DL)-Pip-O—CH$_3$

Deprotection of 100 mg of the compound obtained by the process 1 was performed similarly to that in Example 28 (Process 3), and the obtained product was dissolved in DMF and neutralized with 24 µl of triethylamine under ice cooling. To the neutralized solution, 50 mg of Boc-(2S,3S)-AHPBA-OH and 88 mg of Bop reagent were added and the resultant mixture was stirred overnight at room temperature. The reaction mixture was treated similarly to that in Example 144 (Process 2) to give 40 mg of the title compound.

TLC: Rf 0.58 (chloroform:methanol=9:1)

[Process 3] Boc-Msa-(2S,3S)-AHPBA-Thz-(DL)-Pip-O—CH$_3$

Deprotection of 40 mg of the compound obtained by the process 2 was performed similarly to that in Example 125 (Process 2), and the obtained product was dissolved in DMF and neutralized with 11 µl of triethylamine under ice cooling. To the neutralized solution, 20 mg of Boc-Msa-OH and 40 mg of Bop reagent were added and the resultant mixture was stirred overnight at room temperature. The reaction mixture was treated similarly to that in Example 144 (Process 2) to give 40 mg of the title compound.

TLC: Rf 0.47 (chloroform:methanol=9:1)

[Process 4] 1-Naphthoxyacetyl-Msa-(2S,3S)-AHPBA-Thz-Pi-O—CH$_3$

Deprotection of 20 mg of the compound obtained by the process 3 was performed similarly to that in Example 125 (Process 2), and the obtained product was dissolved in DMF and neutralized with 3 µl of triethylamine under ice cooling. To the neutralized solution, 4 mg of 1-naphthoxyacetic acid and 10 mg of Bop reagent were added and the resultant mixture was stirred overnight at room temperature. The reaction mixture was treated similarly to that in Example 122 to give 2 mg of 1-naphthoxyacetyl-Msa-(2S,3S)-AHPBA-Thz-(D)-Pip-O—CH$_3$ and 1 mg of 1-naphthoxyacetyl-Msa-(2S,3S)-AHPBA-Thz-(L)-Pip-O—CH$_3$.

Analytical HPLC: 21.31, 27.22 min (For the condition, see: Example 35)

FAB-MS: 769 (M+1)

Example 160

1-Naphthoxyacetyl-Phg-(2S,3S)-AHPBA-Thz-NH-tBu

[Process 1] Boc-Phg-(2S,3S)-AHPBA-Thz-NH-tBu

Deprotection of 38 mg of the compound obtained by Example 82 (Process 2) was performed similarly to that in Example 125 (Process 2), and the obtained product was dissolved in DMF and 11 µl of triethylamine, 36 mg of Boc-Phg-OH and 44 mg of Bop reagent were added under ice cooling and the resultant mixture was stirred overnight at room temperature. The reaction mixture was treated similarly to that in Example 93 (Process 3) to give 10 mg of the title compound.

TLC: Rf 0.90 (chloroform:methanol=9:1)

[Process 2] 1-Naphthoxyacetyl-Phg-(2S,3S)-AHPBA-Thz-NH-tBu

Deprotection of 10 mg of the compound obtained by the process 1 was performed similarly to that in Example 125 (Process 2), and the obtained product was dissolved in DMF and neutralized with 37 g l of triethylamine under ice cooling. To the neutralized solution, 3 mg of 1-naphthoxyacetic acid and 12 mg of Bop reagent were added and the resultant mixture was stirred overnight at room temperature. The reaction mixture was treated similarly to that in Example 122 to give 0.4 mg of the title compound. Analytical HPLC: 26.12 min (For the condition, see: Example 35).

FAB-MS: 683 (M+1)

Example 161

1-Naphthoxyacetyl-Ile-(2S,3S)-AHPBA-Thz-NH-tBu

[Process 1] Boc-Ile-(2S,3S)-AHPBA-Thz-NH-tBu

Deprotection of 100 mg of the compound obtained by Example 82 (Process 2) was performed similarly to that in Example 125 (Process 2), and the obtained product was dissolved in DMF and 29 μl of triethylamine, 50 mg of Boc-Ile-OH and 106 mg of Bop reagent were added under ice cooling and the resultant mixture was stirred overnight at room temperature. The reaction mixture was treated similarly to that in Example 93 (Process 3) to give 10 mg of the title compound.

TLC: Rf 0.90 (chloroform:methanol=9:1)

[Process 2] 1-Naphthoxyacetyl-Ile-(2S,3S)-AHPBA-Thz-NH-tBu

Deprotection of 10 mg of the compound obtained by the process 1 was performed similarly to that in Example 125 (Process 2), and the obtained product was dissolved in DMF and neutralized with 37 μl of triethylamine under ice cooling. To the neutralized solution, 3 mg of 1-naphthoxyacetic acid and 12 mg of Bop reagent were added and the resultant mixture was stirred overnight at room temperature. The reaction mixture was treated similarly to that in Example 122 to give 3 mg of the title compound.

Analytical HPLC: 31.15 min (For the condition, see: Example 35).

FAB-MS: 669 (M+1)

Example 162

1-Naphthoxyacetyl-Mta-(2S,3S)-AHPBA-Thz-NH-tBu

[Process 1] Boc-Mta-(2S,3S)-AHPBA-Thz-NH-tBu

Deprotection of 100 mg of the compound obtained by Example 82 (Process 2) was performed similarly to that in Example 125 (Process 2), and the obtained product was dissolved in DMF and 29 μl of triethylamine, 50 mg of Boc-Ile-OH and 106 mg of Bop reagent were added under ice cooling and the resultant mixture was stirred overnight at room temperature. The reaction mixture was treated similarly to that in Example 93 (Process 3) to give 6.5 mg of the title compound.

TLC: Rf 0.90 (chloroform:methanol=9:1)

[Process 2] 1-Naphthoxyacetyl-Mta-(2S,3S)-AHPBA-Thz-NH-tBu

Deprotection of 6.5 mg of the compound obtained by the process 1 was performed similarly to that in Example 125 (Process 2), and the obtained product was dissolved in DMF and neutralized with 30 ul of triethylamine under ice cooling. To the neutralized solution, 3 mg of 1-naphthoxyacetic acid and 12 mg of Bop reagent were added and the resultant mixture was stirred overnight at room temperature. The reaction mixture was treated similarly to that in Example 122 to give 0.7 mg of the title compound.

Analytical HPLC: 30.54 min (For the condition, see: Example 35).

FAB-MS: 667 (M+1)

Example 163

1-Naphthoxyacetyl-Thr(Me)-(2S,3S)-AHPBA-Thz-NH-tBu

[Process 1] Boc-Thr(Me)-OH

In a THF solution containing 0.8 g of Boc-Thr-OH, 100 mg of sodium hydride (60% in oil) was added under ice cooling and the resultant mixture was stirred for 30 min at room temperature. Further, 2.8 ml of methyl iodide was added and the obtained reaction mixture was stirred overnight at room temperature. The reaction mixture was evaporated under reduced pressure and the resultant residue was redissolved in ethyl acetate, washed with 5% sodium hydrogensulfite aqueous solution, water and saturated sodium chloride aqueous solution, successively, and dried over anhydrous sodium sulfate. The dried solution was evaporated under reduced pressure, dissolved in methanol, mixed with DCHA and reevaporated. Ether-hexane was added to the residue to give 0.55 g of the title compound as its DCHA salt.

TLC: Rf 0.63 (chloroform:methanol=9:1)

[Process 2] Boc-Thr(Me)-(2S,3S)-AHPBA-Thz-NH-tBu

Deprotection of 100 mg of the compound obtained by Example 82 (Process 2) was performed similarly to that in Example 125 (Process 2), and the obtained product was dissolved in DMF, and 29 μl of trlethylamine, 50 mg of Boc-Thr(Me)-OH and 106 mg of Bop reagent were added and the resultant mixture was stirred overnight at room temperature. The reaction mixture was treated similarly to that in Example 93 (Process 3) to give 27.1 mg of the title compound.

TLC: Rf 0.50 (chloroform:methanol=9:1)

[Process 3] 1-Naphthoxyacetyl-Thr(Me)-(2S,3S)-AHPBA-Thz-NH-tBu

Deprotection of 27.1 mg of the compound obtained by the process 2 was performed similarly to that in Example 125 (Process 2), and the obtained product was dissolved in DMF and neutralized with 50 μl of triethylamine under ice cooling. To the neutralized solution, 18 mg of 1-naphthoxyacetic acid and 30 mg of Bop reagent were added and the resultant mixture was stirred overnight at room temperature. The reaction mixture was treated similarly to that in Example 122 to give 3 mg of the title compound.

Analytical HPLC: 29.20 min (For the condition, see: Example 35).

FAB-MS: 665 (M+1)

Example 164

Benzyloxycarbonyl-Asn-(2S,3S)-AHPBA-Pdp-NH-tBu

[Process 1] Benzyloxycarbonyl-Pdp-NH-tBu

In a dichloromethane solution containing 100 mg of 1-(Benzyloxycarbonyl)-4-phenyl-2,5-dihydropyrrole-2-carboxylic acid [$C_6H_5$—$CH_2O$—CO-Pdp-OH], 43 μl of triethylamine, 86 mg of 2-chloro-1,3-dimethylimidazolinium hexafluorophosphate and 64 μl of tert-butylamine were added under ice cooling and the resultant mixture was stirred for 14 hr. The reaction mixture was treated similarly to that in Example 28 (Process 2) to give 66 mg of the title compound.

TLC: Rf 0.62 (chloroform:methanol=40:1)

[Process 2] Boc-(2S,3S)-AHPBA-Pdp-NH-tBu

To 66 mg of the protected peptide obtained by the process 1, 3 ml of 30% HBr in acetic acid was added in the presence of 30 μl of anisole and the mixture was stirred for 2 hr at room temperature. The reaction mixture was evaporated under reduced pressure and the resultant residue was redissolved in 3 ml of DMF, and neutralized with 24 μl of triethylamine under ice cooling. To the neutralized solution, 81 mg of Boc-(2S,3S)-AHPBA-OH.DCHA salt, 75 mg of Bop reagent and 24 μl of triethylamine were added and the resultant mixture was stirred overnight. The reaction mixture was treated similarly to that in Example 30 (Process 4) to give 25 mg of the title compound.

TLC: Rf 0.71 (chloroform:methanol=9:1)

[Process 3] Benzyloxycarbonyl-Asn-(2S,3S)-AHPBA-Pdp-NH-tBu

Deprotection of 25 mg of the compound obtained by the process 2 was performed similarly to that in Example 28 (Process 3), and the obtained product was dissolved in 3 ml of DMF and neutralized with 7 μl of triethylamine under ice cooling. To the neutralized solution, 8 mg of benzyloxycarbonyl-Asn-ONp, 11 mg of HOBt and 8 μl of N-methylmorpholine were added and the resultant mixture was stirred for 14 hr. The reaction mixture was treated similarly to that in Example 101 (Process 2) to give 9.7 mg of the title compound.

Analytical HPLC: 25.30 min (For the condition, see: Example 35).

FAB-MS: 670 (M+1)

Example 165

1-Naphthoxyacetyl-Nva-(2S,3S)-AHPBA-Thz-NH-tBu

[Process 1] Boc-Nva-(2S,3S)-AHPBA-Thz-NH-tBu

Deprotection of 32 mg of the compound obtained by Example 82 (Process 2) was performed similarly to that in Example 28 (Process 3), and the obtained product was dissolved in 3 ml of DMF, and neutralized with 9.6 μl of triethylamine under ice cooling. To the neutralized solution, 15 mg of N-Boc-norvaline ( Boc-Nva-OH), 30 mg of Bop reagent and 19.2 μl of triethylamine were added and the resultant mixture was stirred 2 hr. The reaction mixture was treated similarly to that in Example 132 (Process 1) to give 25 mg of the title compound.

TLC: Rf 0.93 (chloroform:methanol=9:1)

[Process 2] 1-Naphthoxyacetyl-Nva-(2S,3S)-AHPBA-Thz-NH-tBu

Deprotection of 25 mg of the compound obtained by the process 1 was performed similarly to that in Example 28 (Process 3), and the obtained product was dissolved in 3 ml of DMF and neutralized with 7.5 μl of triethylamine under ice cooling. To the neutralized solution, 11 mg of 1-naphthoxyacetic acid, 24 mg of Bop reagent and 14.9 μl of triethylamine were added and the resultant mixture was stirred for 2 hr. The reaction mixture was treated similarly to that in Example 137 (Process 5) to give the title compound.

TLC: Rf 0.90 (chloroform:methanol=9:1)

Analytical HPLC: 31.20 min (For the condition, see: Example 35).

FAB-MS: 649 (M+1)

Example 166 m-Isopropyloxyphenoxyacetyl-Msa-(2S,3S)-AHPBA-Dtc-NH-tBu

[Process 1] m-Isopropyloxyphenol [m-(iPro)-Ph-OH]

In 10 ml of THF, 1.5 g of resorcinol was dissolved and 2.24 ml of DBU was added under ice cooling. The resultant mixture was stirred for 10 min at room temperture. To the mixture, 1.92 ml of isopropyl bromide was added and refluxed for 2 hr. The reaction mixture was neutralized with acetic acid and evaporated under reduced pressure. The evaporated residue was redissolved in ethyl acetate and washed with 5% aqueous citric acid solution and saturated aqueous sodium chloride solution, successively, and dried over anhydrous sodium sulfate. The dried solution was evaporated under reduced pressure and the residue was subjected to a silica gel column chromatography (chloroform:methanol=40:1) to give 466 mg of the title compound.

TLC: Rf 0.78 (choroform:methanol=9:1)

[Process 2] m-(iPro)-Ph-O—$CH_2$—$CO_2C_2H_5$

In 5 ml of THF, 466 mg of the product obtained by the process 1 and 0.67 ml methanol solution of sodium metanolate was added under ice cooling followed by stirring for 10 min. To the reaction mixture, 375 μl of ethyl bromoacetate was added and the mixture was refluxed for 2 hr. The reaction mixture was neutralized with acetic acid and evaporated under reduced pressure. The obtained residue was redissolved in ethyl acetate and washed with 5% aqueous citric acid solution and saturated aqueous sodium chloride solution, successively, and dried over anhydrous sodium sulfate. The dried solution was evaporated under reduced pressure and the residue was subjected to a silica gel column chromatography (chloroform) to give 366 mg of the title compound.

TLC: Rf 0.94 (choroform:methanol=9:1)

[Process 3] m-(iPro)-Ph-O—$CH_2$—$CO_2H$

In 4 ml of methanol, 366 mg of the compound obtained by the process 2, 764 μl of 4N-NaOH aqueous solution was added under ice cooling and the resultant solution was stirred for 60 min at room temperature. The reaction mixture was neutralized with acetic acid and evaporated under reduced pressure. The resultant residue was redissolved in ethyl acetate and washed with 5% aqueous citric acid solution and saturated aqueous sodium chloride solution, successively, and dried over anhydrous sodium sulfate. The dried solution was evaporated under reduced pressure and the residue was crystallized by an addition of ether to give 310 mg of the title compound.

TLC: Rf 0.19 (choroform:methanol=9:1)

[Process 4] m-(iPro)-Ph-O—$CH_2$—CO-Msa-(2S,3S)-AHPBA-Dtc-NH-tBu

Deprotection of 105 mg of the compound obtained by Example 105 (Process 1) was performed similarly to that in Example 28 (Process 3), and the obtained product was dissolved in 3 ml of DMF and neutralized with 24 μl of triethylamine under ice cooling. To the neutralized solution, 38 mg of m-(iPro)-Ph-O—$CH_2$—$CO_2H$, 80 mg of Bop reagent and 48 μl of triethylamine were added and the resultant mixture was stirred for 2 hr. The reaction mixture was treated similarly to that in Example 98 to give 5.1 mg of the title compound.

Analytical HPLC: 29.51 min (For the condition, see: Example 35).

FAB-MS: 735 (M+1)

Example 167 m-(Piper-CO-)Ph-O—$CH_2$—CO-Msa-(2S,3S)-AHPBA-Thz-NH-tBu

[Process 1] m-(Piperidinocarbonyl)phenol [m-(Piper-CO)-Ph-OH]

In 15 ml of DMF, 700 mg of m-hydroxybenzoic acid was dissolved, and 2.84 ml of piperidine, 3.80 g of Bop reagent and 70 mg of 4-dimethylaminopyridine were added under ice cooling, and the resultant mixture was stirred for 15 hr. The reaction mixture was evaporated under reduced pressure and the residue was redissolved in ethyl acetate. The ethyl acetate solution was washed with 5% citric acid aqueous solution and saturated sodium chloride aqueous solution, successively, and dried over anhydrous sodium sulfate. The dried solution was evaporated under reduced pressure and subjected to a silica gel column chromatography (chloroform) to give 267 mg of the title compound.

TLC: Rf 0.83 (chloroform:methanol:acetic acid=9:1:0.5)

[Process 2] m-(Piper-CO)-Ph-O—$CH_2$—$CO_2C_2H_5$

In 5 ml of THF, 267 mg of the compound obtained by the process 1 was dissolved and 316 μl of DBU was added under ice cooling. The resultant mixture was stirred for 10 min. To the mixture, 173 μl of ethyl bromoacetate was added and refluxed for 2 hr. The reaction mixture was neutralized with acetic acid and treated similarly to that in the process 1 to give 112 mg of the title compound.

TLC: Rf 0.69 (choroform:methanol=20:1)

[Process 3] m-(Piper-CO)-Ph-O—$CH_2$—$CO_2H$

In 3 ml of methanol, 110 mg of the product obtained by the process 2 was dissolved and 303 μl of 4N-NaOH aqueous solution was added under ice cooling. The resultant solution was stirred for 60 min at room temperature. The reaction mixture was evaporated under reduced pressure, redissolved in ethyl acetate, washed with 5% aqueous citric acid solution and saturated aqueous sodium chloride solution and dried over anhydrous sodium sulfate. The dried solution was evaporated under reduced pressure and crystallized from ether to give 92 mg of the title compound.

TLC: Rf 0.23 (choroform:methanol:water=8:3:1, lower layer)

[Process 4] m-(Piper-CO)-Ph-O—$CH_2$—CO-Msa-(2S,3S)-AHPBA-Thz-NH-tBu

Deprotection of 42 mg of the compound obtained by Example 100 (Process 1) was performed similarly to that in Example 28 (Process 3), and the obtained product was dissolved in 3 ml of DMF and neutralized with 9.1 μl of triethylamine under ice cooling. To the neutralized solution, 18 mg of m-(piperidinocarbonyl)-phenoxyacetic acid, 29 mg of Bop reagent and 18.2 μl of triethylamine were added and the resultant mixture was stirred for 2 hr. The reaction mixture was treated similarly to that in Example 98 to give 20.4 mg of the title compound.

TLC: Rf 0.17 (chloroform:methanol=20:1)

Analytical HPLC: 23.31 min (For the condition, see: Example 35).

FAB-MS: 760 (M+1)

Example 168 m-(Morph-CO)-Ph-O—$CH_2$—CO-Msa-(2S,3S)-AHPBA-Thz-NH-tBu

[Process 1] m-(Morpholinocarbonyl)phenol [m-(Morph-CO)-Ph-OH]

In 15 ml of DMF, 700 mg of m-hydroxybenzoic acid was dissolved, and 2.50 ml of morpholine, 3.04 g of Bop reagent were added under ice cooling, and the resultant mixture was stirred for 3 hr. The reaction mixture was treated similarly to that in Example 28 (Process 2) to give 1.10 g of the title compound.

TLC: Rf 0.34 (chloroform:methanol=20:1)

[Process 2] m-(Morph-CO)-Ph-O—$CH_2$—$CO_2C_2H_5$

In THF, 500 mg of the compound obtained by the process 1 was dissolved and 531 μl of methanol solution of sodium methanolate was added under ice cooling. The resultant mixture was stirred for 10 min. To the mixture, 295 μl of ethyl bromoacetate was added and refluxed for 2 hr. The reaction mixture was treated similarly to that in Example 167 (Precess 2) except for the chromatography solvent (chloroform:methanol=40:1) to give 243 mg of the title compound.

TLC: Rf 0.82 (choroform:methanol=9:1)

[Process 3] m-(Morph-CO)-Ph-O—$CH_2$—$CO_2H$

In methanol, 243 mg of the product obtained by the process 2 was dissolved and 621 μl of 4N-NaOH aqueous solution was added under ice cooling. The resultant solution was stirred for 60 min at room temperature. The reaction mixture was treated similarly to that in Example 167 (Process 3) to give 56 mg of the title compound.

TLC: Rf 0.82 (choroform:methanol=9:1)

[Process 4] m-(Morph-CO)-Ph-O—$CH_2$—CO-Msa-(2S,3S)-AHPBA-Thz-NH-tBu

Deprotection of 28 mg of the compound obtained by Example 100 (Process 1) was performed similarly to that in Example 28 (Process 3), and the obtained product was dissolved in 3 ml of DMF and neutralized with 6.1 μl of triethylamine under ice cooling. To the neutralized solution, 12 mg of m-(Morph-CO)-Ph-O—$CH_2$—$CO_2H$, 20 mg of Bop reagent and 12.1 μl of triethylamine were added and the resultant mixture was stirred for 2 hr. The reaction mixture was treated similarly to that in Example 132 (Process 2) to give 12.1 mg of the title compound.

TLC: Rf 0.30 (chloroform:methanol=20:1)

Analytical HPLC: 19.10 min (For the condition, see: Example 35).

FAB-MS: 762 (M+1)

Example 169 m-(iPrO)-Ph-O—$CH_2$—CO-Asn-(2S,3S)-AHPBA-Dtc-NH-tBu

Deprotection of 32 mg of the compound obtained by Example 106 (Process 1) was performed similarly to that in Example 28 (Process 3), and the obtained product was dissolved in 3 ml of DMF and neutralized with 7.3 μl of triethylamine under ice cooling. To the neutralized solution, 11 mg of m-isopropyloxyphenoxyacetic acid obtained in Example 166 (Process 3), 24 mg of Bop reagent and 14.6 μl of triethylamine were added and the resultant mixture was stirred for 2 hr. The reaction mixture was treated similarly to that in Example 132 (Process 2) to give 7.8 mg of the title compound.

Analytical HPLC: 26.68 min (For the condition, see: Example 35).

FAB-MS: 700 (M+1)

Example 170

1-Naphthoxyacetyl-Alg-(2S,3S)-AHPBA-Thz-NH-tBu

[Process 1] Boc-Alg-(2S,3S)-AHPBA-Thz-NH-tBu

Deprotection of 58 mg of the compound obtained by Example 82 (Process 2) was performed similarly to that in Example 28 (Process 3), and the obtained product was dissolved in 3 ml o f DMF and neutralized with 17.3 µl of triethylamine under ice cooling. To the neutralized solution, 54 mg of Boc-L-allylglycine.DCHA, 61 mg of Bop reagent and 19 µl of triethylamine were added and the resultant mixture was stirred for 2 hr. The reaction mixture was treated similarly to that in Example 139 (Process 2) to give 76 mg of the title compound.

TLC: Rf 0.66 (chloroform:methanol=20:1)

[Process 2] 1-Naphthoxyacetyl-Alg-(2S,3S)-AHPBA-Thz-NH-tBu

Deprotection of 76 mg of the compound obtained by the process 1 was performed similarly to that in Example 30 (Process 2), and the obtained product was dissolved in 3 ml of DMF and neutralized with 18.8 µl of triethylamine under ice cooling. To the neutralized solution, 30 mg of 1-naphthoxyacetic acid, 66 mg of Bop reagent and 39.4 µl of triethylamine were added and the resultant mixture was stirred for 2 hr. The reaction mixture was treated similarly to that in Example 132 (Process 1) to give 39 mg of a crude product. In methanol, 19 mg of the product was dissolved, fractionated by reversed-phase HPLC and lyophilized to give 7.7 mg of the title compound.

TLC: Rf 0.53 (chloroform:methanol=20:1)

Analytical HPLC: 31.26 min (For the condition, see: Example 35).

FAB-MS: 647 (M+1)

Example 171

2,3-diMe-Ph-O—CH$_2$—CO-Asn-(2S,3S)-AHPBA-Dtc-NH-tBu

[Process 1] 2,3-diMe-Ph-O—CH$_2$—CO$_2$C$_2$H$_5$

To a THF solution of 500 mg of 2,3-dimethylphenol(2,3-diMe-Ph-OH), 672 µl of DBU was added under ice cooling. The resultant mixture was stirred for 10 min at room temperture. To the mixture, 50 µl of ethyl bromoacetate was added and refluxed for 2 hr. The reaction mixture was treated similarly to that in Example 167 (Process 2) to give 156 mg of the title compound.

TLC: Rf 0.89 (choroform:methanol=20:1)

[Process 2] 2,3-diMe-Ph-O—CH$_2$—CO$_2$H

In a methanol solution containing the compound obtained by the process 1, 375 µl of 4N-NaOH aqueous solution was added under ice cooling and the resultant mixture was stirred for 60 min at room temperature and treated similarly to that in Example 166 (Process 3)to give 126 mg of the title compound.

TLC: Rf 0.20 (choroform:methanol=9:1)

[Process 3] 2,3-diMe-Ph-O—CH$_2$—CO-Asn-(2S,3S)-AHPBA-Dtc-NH-tBu

Deprotection of 33 mg of the compound obtained by Example 106 (Process 1) was performed similarly to that in Example 28 (Process 3), and the obtained product was dissolved in 3 ml of DMF and neutralized with 10.4 µl of triethylamine under ice cooling. To the neutralized solution, 14 mg of 2,3-dimethylphenoxyacetic acid, 33 mg of Bop reagent and 20.7 µl of triethylamine were added and obtained mixture was stirred for 2 hr. The reaction mixture was treated similarly to that in Example 132 (Process 2) to give 6.1 mg of the title compound.

TLC: Rf 0.43 (choroform:methanol=9:1)

Analytical HPLC: 26.55 min (For the condition, see: Example 35).

FAB-MS: 671 (M+1)

Example 172

1-Naphthoxyacetyl-Msa-(2S,3S)-AHPBA-Thz-Gly-NH$_2$

[Process 1] Boc-Thz-Gly-NH

Deprotection of 500 mg of Boc-Gly-NH$_2$ was performed similarly to that in Example 28 (Process 3), and the obtained product was dissolved in dichloromethane, and 0.39 ml of tri-ethylamine, 0.67 g of Boc-Thz-OH, 0.47 g of HOBt and 0.64 g of EDC hydrochloride were added under ice cooling and the mixture was stirred overnight at room temperature. The reaction mixture was treated similarly to that in Example 139 (Process 2) to give 0.54 g of the title compound as oil.

TLC: Rf 0.63 (chloroform:methanol=9:1)

[Process 2] Boc-(2S,3S)-AHPBA-Thz-Gly-NH$_2$

Deprotection of 540 mg of the compound obtained by the process 1 was performed similarly to that in Example 125 (Process 2) and the obtained product was dissolved in DMF. To the solution, 90 ul of triethylamine, 100 mg of Boc-(2S,3S)-AHPBA-OH and 160 mg of Bop reagent were added under ice cooling and the mixture was stirred overnight at room temperature. The reaction mixture was treated similarly to that in Example 93 (Process 3) to give 13.5 mg of title compound.

TLC: Rf 0.48 (choroform:methanol=9:1)

[Process 3] Boc-Msa-(2S,3S)-AHPBA-Thz-Gly-NH$_2$

Deprotection of 13.5 mg of the compound obtained by the process 2 was performed similarly to that in Example 125 (Process 2), and the obtained product was dissolved in DMF. To the solution, 5 µl of triethylamine, 13 mg of Boc-Msa-OH and 21 mg of Bop reagent were added under ice cooling and the mixture was stirred overnight at room temperature. The reaction mixture was treated similarly to that in Example 93 (Process 3) to give 20 mg of title compound.

TLC: Rf 0.15 (choroform:methanol=9:1)

[Process 4] 1-Naphthoxyacetyl-Msa-(2S,3S)-AHPBA-Thz-Gly-NH$_2$

Deprotection of 20 mg of the compound obtained by the process 3 was performed similarly to that in Example 125 (Process 2), and the obtained product was dissolved in DMF and neutralized with 6 µl of triethylamine under ice cooling. To the neutralized solution, 9 mg of 1-naphthoxyacetic acid and 21 mg of Bop reagent were added and the mixture was stirred overnight at room temperature. The reaction mixture was treated similarly to that in Example 122 to give 3 mg of the title compound.

Analytical HPLC: 20.06 min (For the condition, see: Example 35).

FAB-MS: 700 (M+1)

Example 173

1-Naphthoxyacetyl-Msa-(2S,3S)-AHPBA-Thz-GABA-NH$_2$

[Process 1] Boc-Thz-GABA-NH$_2$

Deprotection of 400 mg of 4-N-t-butoxycarbonylaminobutanamide [Boc-GABA-NH$_2$] was performed similarly to that in Example 125 (Process 2), and the obtained product was dissolved in dichloromethane, and 0.28 ml of tri-ethylamine, 0.47 g of Boc-Thz-OH, 1.06 g of Bop reagent were added under ice cooling and the mixture was stirred overnight at room temperature. The reaction mixture was treated similarly to that in Example 144 (Process 2) to give 27 mg of the title compound.

TLC: Rf 0.56 (chloroform:methanol=9:1)

[Process 2] Boc-(2S,3S)-AHPBA-Thz-GABA-NH$_2$

Deprotection of 95 mg of the compound obtained by the process 1 was performed similarly to that in Example 125 (Process 2), and the obtained product was dissolved in DMF. To the solution, 42 µl of triethylamine, 89 mg of Boc-(2S,3S)-AHPBA-OH and 146 mg of Bop reagent was added under ice cooling and the mixture was stirred overnight at room temperature. The reaction mixture was treated similarly to that in Example 93 (Process 3) to give 62 mg of title compound.

TLC: Rf 0.30 (choroform:methanol=9:1)

[Process 3] Boc-Msa-(2S,3S)-AHPBA-Thz-GABA-NH$_2$

Deprotection of 62 mg of the compound obtained by the process 2 was performed similarly to that in Example 125 (Process 2), and the obtained product was dissolved in DMF. To the solution, 17.5 µl of triethylamine, 37 mg of Boc-Msa-OH and 61 mg of Bop reagent were added under ice cooling and the mixture was stirred overnight at room temperature. The reaction mixture was treated similarly to that in Example 144 (Process 2) to give 30 mg of the title compound.

TLC: Rf 0.18 (choroform:methanol=9:1)

[Process 4] 1-Naphthoxyacetyl-Msa-(2S,3S)-AHPBA-Thz-GABA-NH$_2$

Deprotection of 30 mg of the compound obtained by the process 3 was performed similarly to that in Example 125 (Process 2), and the obtained product was dissolved in DMF and neutralized with 6.6 µl of triethylamine under ice cooling. To the neutralized solution, 9.5 mg of 1-naphthoxyacetic acid and 23 mg of Bop reagent were added and the mixture was stirred overnight at room temperature. The reaction mixture was treated similarly to that in Example 122 to give 2 mg of the title compound.

Analytical HPLC: 20.58 min (For the condition, see: Example 35).

FAB-MS: 728 (M+1)

Example 174

1-Naphthoxyacetyl-Msa-(2S,3S)-AHPBA-Thz-BAIB-NH$_2$

[Process 1] Boc-Thz-BAIB-NH$_2$

Deprotection of 400 mg of 3-N-t-butoxycarbonylamino-2-methylpropanamide (Boc-BAIB-NH$_2$] was performed similarly to that in Example 125 (Process 2), and the obtained product was dissolved in dichloromethane, and 0.29 ml of triethylamine, 0.47 g of Boc-Thz-OH, 1.06 g of Bop reagent were added under ice cooling and the mixture was stirred overnight at room temperature. The reaction mixture was treated similarly to that in Example 93 (Process 3) to give 0.52 g of the title compound.

TLC: Rf 0.83 (chloroform:methanol=9:1)

[Process 2] Boc-(2S,3S)-AHPBA-Thz-BAIB-NH$_2$

Deprotection of 130 mg of the compound obtained by the process 1 was performed similarly to that in Example 125 (Process 2), and the obtained product was dissolved in DMF. To the solution, 56 µl of triethylamine, 180 mg of Boc-(2S,3S)-AHPBA-OH and 194 mg of Bop reagent were added under ice cooling and the mixture was stirred overnight at room temperature. The reaction mixture was treated similarly to that in Example 144 (Process 2) to give 40 mg of the title compound.

TLC: Rf 0.48 (choroform:methanol=9:1)

[Process 3] Boc-Msa-(2S,3S)-AHPBA-Thz-BAIB-NH$_2$

Deprotection of 40 mg of the compound obtained by the process 2 was performed similarly to that in Example 125 (Process 2), and the obtained product was dissolved in DMF. To the solution, 11 µl of triethylamine, 24 mg of Boc-Msa-OH and 39 mg of Bop reagent were added under ice cooling and the mixture was stirred overnight at room temperature. The reaction mixture was treated similarly to that in Example 93 (Process 3) to give 30 mg of the title compound.

TLC: Rf 0.52 (choroform:methanol=9:1)

[Process 4] 1-Naphthoxyacetyl-Msa-(2S,3S)-AHPBA-Thz-BAIB-NH$_2$

Deprotection of 30 mg of the compound obtained by the process 3 was performed similarly to that in Example 125 (Process 2), and the obtained product was dissolved in DMF and neutralized with 6.6 µl of triethylamine under ice cooling. To the neutralized solution, 10 mg of 1-naphthoxyacetic acid and 25 mg of Bop reagent were added and the mixture was stirred overnight at room temperature. The reaction mixture was treated similarly to that in Example 122 to give 5 mg of the title compound.

Analytical HPLC: 21.27 min (For the condition, see: Example 35).

FAB-MS: 728 (M+1)

Example 175

1-Naphthoxyacetyl-Msa-(2S,3S)-AHPBA-Thz-BANB-NH$_2$

[Process 1] Boc-Thz-BANB-NH$_2$

Deprotection of 400 mg of 3-N-t-butoxycarbonylaminobutanamide [Boc-BANB-NH$_2$] was performed similarly to that in Example 125 (Process 2), and the obtained product was dissolved in dichloromethane, and 0.29 ml of triethylamine, 0.47 g of Boc-Thz-OH, 1.06 g of Bop reagent were added under ice cooling and the mixture was stirred overnight at room temperature. The reaction mixture was treated similarly to that in Example 93 (Process 3) to give 0.38 g of the title compound.

TLC: Rf 0.67 (chloroform:methanol=9:1)

[Process 21 Boc-(2S,3S)-AHPBA-Thz-BANB-NH$_2$

Deprotection of 130 mg of the compound obtained by the process 1 was performed similarly to that in Example 125 (Process 2), and the obtained product was dissolved in DMF. To the solution, 77 µl of triethylamine, 162 mg of Boc-(2S,3S)-AHPBA-OH and 270 mg of Bop reagent were added under ice cooling and the mixture was stirred overnight at room temperature. The reaction mixture was tested similarly to that in Example 144 (Process 2) to give 60 mg of the title compound.

TLC: Rf 0.48 (choroform:methanol=9:1)

[Process 3] Boc-Msa-(2S,3S)-AHPBA-Thz-BANB-NH$_2$

Deprotection of 60 mg of the compound obtained by the process 2 was performed similarly to that in Example 125 (Process 2), and the obtained product was dissolved in DMF. To the solution, 17 μl of triethylamine, 36 mg of Boc-Msa-OH and 58 mg of Bop reagent were added under ice cooling and the mixture was stirred overnight at room temperature. The reaction mixture was treated similarly to that in Example 93 (Process 3) to give 30 mg of the title compound.

TLC: Rf 0.51 (choroform:methanol=9:1)

[Process 4] 1-Naphthoxyacetyl-Msa-(2S,3S)-AHPBA-Thz-BANB-NH$_2$

Deprotection of 30 mg of the compound obtained by the process 3 was performed similarly to that in Example 125 (Process 2), and the obtained product was dissolved in DMF and neutralized with 6.6 μl of triethylamine under ice cooling. To the neutralized solution, 10 mg of 1-naphthoxyacetic acid and 25 mg of Bop reagent were added and the mixture was stirred overnight at room temperature. The reaction mixture was treated similarly to that in Example 122 to give 3 mg of the title compound.

Analytical HPLC: 20.74 min (For the condition, see: Example 35).

FAB-MS: 728 (M+1)

Example 176

Benzyloxycarbonyl-Asn-(2S3S)-AHPBA-Pro-NHsBu

[Process 1] Boc-Pro-NH—CH(CH$_3$)(C$_2$H$_5$) [Boc-Pro-NH-sBu]

In dichloromethane solution containing 0.1 g of sec-butylamine, 0.5 g of Boc-Pro-OH, 0.2 g of HOBt and 0.3 g of EDC hydrochloride were added under ice cooling and the mixture was stirred overnight at room temperature. The reaction mixture was treated similarly to that in Example 144 (Process 2) to give 0.4 g of the title compound.

TLC: Rf 0.84 (choroform:methanol=9:1)

[Process 2] Boc-(2S,3S)-AHPBA-Pro-NH-sBu

Deprotection of 57 mg of the compound obtained by the process 1 was performed similarly to that in Example 125 (Process 2), and the obtained product was dissolved in dichloromethane. To the solution, 29 μl of triethylamine, 100 mg of Boc-(2S,3S)-AHPBA-OH and 112 mg of Bop reagent were added under ice cooling and the mixture was stirred overnight at room temperature. The reaction mixture was treated similarly to that in Example 144 (Process 2) to give 0.12 g of the title compound.

TLC: Rf 0.46 (choroform:methanol=9:1)

[Process 3] Benzyloxycarbonyl-Asn-(2S,3S)-AHPBA-Pro-NH-sBu

Deprotection of 60 mg of the compound obtained by the process 2 was performed similarly to that in Example 125 (Process 2), and the obtained product was dissolved in dichloromethane. To the solution, 19 μl of triethylamine and 52 mg of benzyloxycarbonyl-Asn-ONp were added under ice cooling and the mixture was stirred overnight at room temperature. The reaction mixture was treated similarly to that in Example 122 to give 2 mg of the title compound.

Analytical HPLC: 20.14 min (For the condition, see: Example 35).

FAB-MS: 596 (M+1)

Example 177

Benzyloxycarbonyl-Asn-(2S,3S)-AHPBA-Dtc-NH$_2$

[Process 1] Boc-Dtc-NH$_2$

A THF solution containing 0.2 g of Boc-Dtc-OH was chilled to −15° C. and 108 μl of triethylamine and 101 μl of isobutyl chloroformate were added. Further 15 min later, 2 ml of ammonia water (28%) was added and the mixture was stirred overnight. The reaction mixture was evaporated under reduced pressure and the residue was redissolved in ethyl acetate, washed with 5% aqueous sodium hydrogencarabonate solution, 10% aqueous citric acid solution and saturated aqueous sodium chloride solution, successively, and dried over anhydrous sodium sulfate. The dried solution was evaporated under reduced pressure to give 0.12 g of the title compound as oil.

TLC: Rf 0.48 (chloroform:methanol=9:1)

[Process 2] Boc-(2S,3S)-AHPBA-Dtc-NH$_2$

Deprotection of 120 mg of the compound obtained by the process 1 was performed similarly to that in Example 125 (Process 2), and the obtained product was dissolved in dichloromethane. To the solution, 64.4 μl of triethylamine, 219 mg of Boc-(2S,3S)-AHPBA-OH and 224 mg of Bop reagent were added under ice cooling and the mixture was stirred overnight at room temperature. The reaction mixture was treated similarly to that in Example 144 (Process 2) to give 170 mg of the title compound.

TLC: Rf 0.61 (choroform:methanol=9:1)

[Process 3] Benzyloxycarbonyl-Asn-(2S,3S)-AHPBA-Dtc-NH$_2$

Deprotection of 44 mg of the compound obtained by the process 2 was performed similarly to that in Example 125 (Process 2), and the obtained product was dissolved in DMF. To the solution, 14 μl of triethylamine and 78 mg of benzyloxycarbonyl-Asn-ONp were added under ice cooling and the mixture was stirred overnight at room temperature. The reaction mixture was treated similarly to that in Example 122 to give 1 mg of the title compound.

Analytical HPLC: 21.90 min (For the condition, see: Example 35).

FAB-MS: 586 (M+1)

Example 179

1-Naphthoxyacetyl-Val-(2S,3S)-AHPBA-Thz-NH-tBu

[Process 1] Boc-Val-(2S,3S)-AHPBA-Thz-NH-tBu

Deprotection of 45 mg of the compound obtained by Example 82 (Process 2) was performed similarly to that in Example 125 (Process 2), and the obtained product was dissolved in DMF. To the solution, 14 μl of triethylamine, 22 mg of Boc-Val-OH and 53 mg of Bop reagent were added under ice cooling and the mixture was stirred overnight at room temperature. The reaction mixture was treated similarly to that in Example 93 (Process 3) to give 40 mg of the title compound.

TLC: Rf 0.69 (choroform:methanol=9:1)

[Process 2] 1-Naphthoxyacetyl-Val-(2S,3S)-AHPBA-Thz-NH-tBu

Deprotection of 40 mg of the compound obtained by the process 1 was performed similarly to that in Example 125 (Process 2), and the obtained product was dissolved in DMF. The solution was neutralized with 10 μl of triethylamine under ice cooling. To the neutralized solution, 14 mg of 1-naphthoxyacetic acid and 37 mg of Bop reagent were added and the mixture was stirred overnight at room temperature. The reaction mixture was treated similarly to that in Example 122 to give 2 mg of the title compound.

Analytical HPLC: 30.54 min (For the condition, see: Example 35).

FAB-MS: 649 (M+1)

Example 180

1-NaPhthoxyacetyl-Prg-(2S,3S)-AHPBA-Thz-NH-tBu

[Process 1] N-(t-butoxycarbonyl)propargyrglycine [Boc-Prg-OH]

In a THF solution containing 1.0 g of diethyl N-benzyloxycarbonylaminomalonate, 0.17 g of sodium hydride (60% in oil) was added under ice cooling and the mixture was stirred for 30 min. The reaction mixture was evaporated under reduced pressure and redissolved in dimethylsulfoxide (DMSO). To the solution, 0.36 ml of propargyl bromide was added and the mixture was stirred overnight. The reaction mixture was mixed with water and extracted with ether. The ether layer was washed with saturated aqueous sodium chloride and dried over sodium sulfate. The dried solution was evaporated under reduced pressure and the residue was hydrolyzed with 2N-NaOH for 5 hr, followed by t-butoxycarbonylation with (Boc)₂O to give 0.6 g of the title compound.

TLC: Rf 0.37 (chloroform:methanol=5:1)

[Process 2] Boc-Prg-(2S,3S)-AHPBA-Thz-NH-tBu

Deprotection of 55 mg of the compound obtained by Example 82 (Process 2) was performed similarly to that in Example 125 (Process 2), and the obtained product was dissolved in DMF. To the solution, 20 μl of triethylamine, 55 mg of Boc-Prg-OH and 76 mg of Bop reagent were added under ice cooling and the mixture was stirred overnight at room temperature. The reaction mixture was treated similarly to that in Example 93 (Process 3) to give 80 mg of the title compound.

TLC: Rf 0.76 (choroform:methanol=9:1)

[Process 3] 1-Naphthoxyacetyl-Prg-(2S,3S)-AHPBA-Thz-NH-tBu

Deprotection of 80 mg of the compound obtained by the process 2 was performed similarly to that in Example 125 (Process 2), and the obtained product was dissolved in DMF. The solution was neutralized with 19.6 μl of triethylamine under ice cooling. To the neutralized solution, 28 mg of 1-naphthoxyacetic acid and 74 mg of Bop reagent were added and the mixture was stirred overnight at room temperature. The reaction mixture was treated similarly to that in Example 122 to give 1 mg of the title compound.

Analytical HPLC: 29.74 min (For the condition, see: Example 35).

FAB-MS: 645 (M+1)

Example 181

1-Naphthoxyacetyl-Aca-(2S,3S)-AHPBA-Thz-NH-tBu

[Process 1] 2-(N-t-butoxycarbonylamino)-4-oxopentanoic acid [Boc-Aca-OH]

In a THF solution containing 1 g of diethyl N-benzyloxycarbonylaminomalonate, 0.17 g of sodium hydride was added under ice cooling and the mixture was stirred for 30 min. The reaction mixture was evaporated under reduced pressure and redissolved in DMSO. To the solution, 0.26 ml of bromoacetone was added under ice cooling and the mixture was stirred overnight. The reaction mixture was treated similarly to that in Example 180 (Process 1) to give 294 mg of the title compound.

TLC: Rf 0.24 (chloroform:methanol=5:1)

[Process 2] Boc-Aca-(2S,3S)-AHPBA-Thz-NH-tBu

Deprotection of 63 mg of the compound obtained by Example 82 (Process 2) was performed similarly to that in Example 125 (Process 2), and the obtained product was dissolved in DMF. To the solution, 31 μl of triethylamine, 90 mg of Boc-Aca-OH and 117 mg of Bop reagent were added under ice cooling and the mixture was stirred overnight at room temperature. The reaction mixture was treated similarly to that in Example 30 (Process 4) to give 40 mg of the title compound.

TLC: Rf 0.74 (choroform:methanol=9:1)

[Process 3] 1-Naphthoxyacetyl-Aca-(2S,3S)-AHPBA-Thz-NH-tBu

Deprotection of 40 mg of the compound obtained by the process 2 was performed similarly to that in Example 125 (Process 2), and the obtained product was dissolved in DMF. The solution was neutralized with 9.7 μl of triethylamine under ice cooling. To the neutralized solution, 14 mg of 1-naphthoxyacetic acid and 37 mg of Bop reagent were added and the mixture was stirred overnight at room temperature. The reaction mixture was treated similarly to that in Example 122 to give 1 mg of the title compound.

Analytical HPLC: 25.79 min (For the condition, see: Example 35).

FAB-MS: 663 (M+1)

Example 182

Benzyloxycarbonyl-Asn-(2S,3S)-AHPBA-Dmp-NH-tBu

[Process 1] Boc-Dmp-NH-tBu

In dichloromethane solution containing 95 mg of tert-butylamine, 280 mg of 1-t-butoxycarbonyl-3,3-dimethylpyrrolidine-2-carboxylic acid [Boc-Dmp-OH] and 320 mg of 2-chloro-1,3-dimethylimidazolinium hexafluorophosphate were added under ice cooling and the mixture was stirred overnight at room temperature. The reaction mixture was treated similarly to that in Example 28 (Process 3) to give 90 mg of the title compound.

TLC: Rf 0.86 (chloroform:methanol=20:1)

[Process 2] Boc-(2S,3S)-AHPBA-Dmp-NH-tBu

Deprotection of 90 mg of the compound obtained by the process 1 was performed similarly to that in Example 125

(Process 2), and the obtained product was dissolved in dichloromethane. To the solution, 89 mg of Boc-(2S,3S)-AHPBA-OH and 159 mg of Bop reagent were added under ice cooling and the mixture was stirred overnight at room temperature. The reaction mixture was treated similarly to that in Example 144 (Process 2) to give 82 mg of the title compound.

TLC: Rf 0.78 (chloroform:methanol=9:1)

[Process 3] Benzyloxycarbonyl-Asn-(2S,3S)-AHPBA-Dmp-NH-tBu

Deprotection of 65 mg of the compound obtained by the process 2 was performed similarly to that in Example 125 (Process 2), and the obtained product was dissolved in DMF. To the solution was added with 19 µl of triethylamine, 80 mg of benzyloxycarbonyl-Asn-ONp, 32 mg of HOBT and 23 µl of N-methylmorpholine under ice cooling, and the mixture was stirred overnight at room temperature. The reaction mixture was treated similarly to that in Example 132 (Process 2) to give a crude title compound. The crude solid was dissolved in methanol and subjected to a reversed-phase HPLC (water-acetonitrile system), fractionated, purified and lyophilized to give 10.3 mg of the title compound.

Analytical HPLC: 23.06 min (For the condition, see: Example 35).

FAB-MS: 624 (M+1)

Example 183

1-Naphthoxyacetyl-Msa-(2S,3S)-AHPBA-Dmp-NH-tBu

[Process 1] Boc-Msa-(2S,3S)-AHPBA-Dmp-NH-tBu

Deprotection of 82 mg of the compound obtained by Example 182 (Process 2) was performed similarly to that in Example 125 (Process 2), and the obtained product was dissolved in DMF. To the solution, 81 mg of Boc-Msa-OH and 134 mg of Bop reagent were added under ice cooling and the mixture was stirred overnight at room temperature. The reaction mixture was treated similarly to that in Example 144 (Process 2) to give 78 mg of the title compound.

TLC: Rf 0.54 (chloroform:methanol=9:1)

[Process 2] 1-Naphthoxyacetyl-Msa-(2S,3S)-AHPBA-Dmp-NH-tBu

Deprotection of 78 mg of the compound obtained by the process 1 was performed similarly to that in Example 125 (Process 2), and the obtained product was dissolved in DMF. The solution was neutralized with 15.4 µl of triethylamine under ice cooling. To the neutralized solution, 23 mg of 1-naphthoxyacetic acid and 54 mg of Bop reagent were added and the mixture was stirred overnight at room temperature. The reaction mixture was treated similarly to that in Example 122 to give 3 mg of the title compound.

Analytical HPLC: 29.27 min (For the condition, see: Example 35).

FAB-MS: 709 (M+1)

Example 184

Benzyloxycarbonyl-Asn-(2S,3S)-AHPBA-Php-NH-tBu

[Process 1] Boc-Php-NH-tBu

In dichloromethane solution containing 50 mg of tert-butylamine, 200 mg of 1-t-butoxycarbonyl 3-phenylpyrrolidine-2-carboxylic acid (Boc-Php-OH) and 140 mg of 2-chloro-1,3-dimethylimidazolinium hexafluorophosphate were added under ice cooling and the mixture was stirred overnight at room temperature. The reaction mixture was treated similarly to that in Example 139 (Process 2) to give 190 mg of the title compound.

TLC: Rf 0.83 (chloroform:methanol=20:1)

[Process 2] Boc-(2S,3S)-AHPBA-Php-NH-tBu

Deprotection of 190 mg of the compound obtained by the process 1 was performed similarly to that in Example 125 (Process 2), and the obtained product was dissolved in dichloromethane. To the solution, 37 µl of triethylamine, 261 mg of Boc-(2S,3S)-AHPBA-OH and 292 mg of Bop reagent were added under ice cooling and the mixture was stirred overnight at room temperature. The reaction mixture was treated similarly to that in Example 132 (Process 1) to give 100 mg of the title compound.

TLC: Rf 0.78 (chloroform:methanol=9:1)

[Process 3] Benzyloxycarbonyl-Asn-(2S,3S)-AHPBA-Php-NH-tBu

Deprotection of 100 mg of the compound obtained by the process 2 was performed similarly to that in Example 125 (Process 2), and the obtained product was dissolved in DMF. To the solution were added 26.6 Il of triethylamine and 77 mg of benzyloxycarbonyl-Asn-ONp under ice cooling and the mixture was stirred overnight at room temperature. The reaction mixture was treated similarly to that in Example 122 to give 2 mg of the title compound.

Analytical HPLC: 25.62 min (For the condition, see: Example 35).

FAB-MS: 672 (M+1)

Example 185

Benzyloxycarbonyl-Asn-(2S,3S)-AHPBA-Cpp-NH-tBu

[Process 1] Boc-Cpp-NH-tBu

In dichloromethane solution containing 25 mg of tert-butylamine, 100 mg of cis-1-t-butoxycarbonyl-4-phenylpyrrolidine-2-carboxylic acid (Boc-Cpp-OH), 50 mg of HOBt and 79 mg of EDC hydrochloride were added under ice cooling and the mixture was stirred overnight at room temperature. The reaction mixture was treated similarly to that in Example 144 (Process 2) to give 90 mg of the title compound.

TLC: Rf 0.86 (chloroform:methanol=20:1)

[Process 2] Boc-(2S,3S)-AHPBA-Cpp-NH-tBu

Deprotection of 35 mg of the compound obtained by the process 1 was performed similarly to that in Example 125 (Process 2), and the obtained product was dissolved in dichloromethane. To the solution, 14 µl of triethylamine, 48 mg of Boc-(2S,3S)-AHPBA-OH and 53 mg of Bop reagent were added under ice cooling and the mixture was stirred overnight at room temperature. The reaction mixture was treated similarly to that in Example 144 (Process 2) to give 60 mg of the title compound.

TLC: Rf 0.78 (chloroform:methanol=9:1)

[Process 3] Benzyloxycarbonyl-Asn-(2S,3S)-AHPBA-Cpp-NH-tBu

Deprotection of 30 mg of the compound obtained by the process 2 was performed similarly to that in Example 125

(Process 2), and the obtained product was dissolved in DMF. To the solution were added 8.4 µl of triethylamine and 23 mg of benzyloxycarbonyl-Asn-ONp under ice cooling and the mixture was treated similarly to that in Example 122 to give 2 mg of the title compound.

Analytical HPLC: 26.23 min (For the condition, see: Example 35).

FAB-MS: 672 (M=1)

Example 186

Benzyloxycarbonyl-Asn-(2S,3S)-AHPBA-Tcp-NH-tBu

[Process 1] Boc-Tcp-NH-tBu

In dichloromethane solution containing 25 mg of tert-butylamine, 100 mg of trans-1-t-butoxycarbonyl-4-cyclohexylpyrrolidine-2-car boxylic acid (Boc-Tcp-OH), 63 mg of HOBt and 84 mg of EDC hydrochloride were added under ice cooling and the mixture was stirred overnight at room temperature. The reaction mixture was treated similarly to that in Example 144 (Process 2) to give 160 mg of the title compound.

TLC: Rf 0.90 (chloroform:methanol=9:1)

[Process 2] Boc-(2S,3S)-AHPBA-Tcp-NH-tBu

Deprotection of 35 mg of the compound obtained by the process 1 was performed similarly to that in Example 125 (Process 2) and the obtained product was dissolved in dichloromethane. To the solution, 14 µl of triethylamine, 49 mg of Boc-(2S,3S)-AHPBA-OH and 53 mg of Bop reagent were added under ice cooling and the mixture was stirred overnight at room temperature. The reaction mixture was treated similarly to that in Example 93 (Process 3) to give 40 mg of the title compound.

TLC: af 0.52 (chloroform:methanol=9:1)

[Process 3] Benzyloxycarbonyl-Asn-(2S,3S)-AHPBA-Tcp-NH-tBu

Deprotection of 40 mg of the compound obtained by the process 2 was performed similarly to that in Example 125 (Process 2), and the obtained product was dissolved in DMF. To the solution were added 11.2 µl of triethylamine and 32 mg of benzyloxycarbonyl-Asn-ONp under ice cooling and the mixture was stirred overnight at room temperature. The reaction mixture was treated similarly to that in Example 122 to give 3 mg of the title compound.

Analytical HPLC: 30.16 min (For the condition, see: Example 35).

FAB-MS: 678 (M+1)

Example 187

Benzyloxycarbonyt-Asn-(2S,3S)-AHPBA-Ccp-NH-tBu

[Process 1] Boc-Ccp-NH-tBu

In a dichloromethane solution containing 25 mg of tert-butylamine, 110 mg of cis-1-t-butoxycarbonyl-4-cyclohexylpyrrolidine-2-carboxylic acid (Boc-Ccp-OH), 63 mg of HOBt and 84 mg of EDC hydrochloride were added under ice cooling and the mixture was stirred overnight at room temperature. The reaction mixture was treated similarly to that in Example 144 (Process 2) to give 170 mg of the title compound.

TLC: Rf 0.87 (chloroform:methanol=9:1)

[Process 2] Boc-(2S,3S)-AHPBA-Ccp-NH-tBu

Deprotection of 35 mg of the compound obtained by the process 1 was performed similarly to that in Example 125 (Process 2), and the obtained product was dissolved in dichloromethane. To the solution, 14 µl of triethylamine, 48 mg of Boc-(2S,3S)-AHPBA-OH and 53 mg of Bop reagent were added under ice cooling and the mixture was stirred overnight at room temperature. The reaction mixture was treated similarly to that in Example 93 (Process 3) to give 20 mg of the title compound.

TLC: Rf 0.78 (chloroform:methanol=9:1)

[Process 3] Benzyloxycarbonyl-Asn-(2S,3S)-AHPBA-Ccp-NH-tBu

Deprotection of 20 mg of the compound obtained by the process 2 was performed similarly to that in Example 125 (Process 2), and the obtained product was dissolved in DMF. To the solution were added 5.6 µl of triethylamine and 16 mg of benzyloxycarbonyl-Asn-ONp under ice cooling and the mixture was stirred overnight at room temperature. The reaction mixture was treated similarly to that that in Example 122 to give 2 mg of the title compound.

Analytical HPLC: 29.94 min (For the condition, see: Example 35).

FAB-MS: 678 (M+1)

Example 188

Benzyloxycarbonyl-Asn-(2S,3S)-AHPBA-Dmp-NH$_2$

The title compound was obtained by a similar method to that of Example 177.

Analytical HPLC: 22.00 min (For the condition, see: Example 35).

FAB-MS: 568 (M+1)

Example 189

Inhibitory Assay Using Chemically Synthesized HIV Protease

The HIV protease was chemically synthesized by replacement of two cysteine residues in the natural sequence [Science, 230, 949 (1985)] with alanine residues. The reaction mixture contained 100 mM MES buffer (pH 5.5), 40 mM of substrate (Ac-Arg-Ala-Ser-Gln-Asn-Tyr-Pro-Val-Val-NH, trifluoroacetate), inhibitors at varying concentrations dissolved in DMSO and 9.2 µg of the HIV protease in a total volume of 15 µl. Incubation was carried out at 37° C. for 60 min. The reaction was started by the addition of the enzyme and terminated by 15 µl of acetonitrile. The amount of a fragment peptide produced was measured by reversed-phase HPLC analysis using an internal standerd. The HPLC condition was as followes.

Column: VYDAC 218 TP 54, C18

Solvent A: 0.1% trifluoroacetic acid aqueous solution

Solvent B: acetonitrile

Gradient: B was increased in 1.0%/min from 100% of A,

The residual enzymic activity in the presence of 5 µM (final concentration) of the inhibitor obtained in Example 32 was 4.0%. In addition, the inhibitor showed 60 nM of $IC_{50}$ and 10 nM of Ki.

The residual activities in the presence of various inhibitors were determined by similar methods and the results are shown in Tables 1–7.

Example 190

Inhibitors Activity Assay Using Recombinant HIV Protease

The inhibitory assay using recombinant HIV protease with the natural amino acid sequence expressed by *Escherichia coli* [Biochemistry, 29, 264 (1990)] was performed by a similar condition to that in Example 189, except for the amount of the enzyme used (2.0 µg). The residual enzymic activity in the presence of 5 µM (final concentration) of the inhibitor obtained in Example 32 was 11.0%.

Example 191

Pharmaceutical Preparation (1) The peptide derivative obtained in Example 32 (10 mg), 200 mg of lactose and 10 mg of magnesium stearate were thoroughly mixed and filled in a hard capsule for oral preparation.

(2) The peptide derivative obtained in Example 32 (5 mg), vegetable oil and saline solution for injection were mixed to make an ampule preparation of 2 ml volume.

Example 192

5Isoquinoline-O—CH$_2$CO-Asn-(2S,3S)-AHPBA-Thz-NH-tBu

The title compound, which may be prepared from the protected peptide obtained in Example 101 (Process 1) and the carboxylic acid obtained in Example 115 (Process 1) by a similar method to that in Example 123 (Process 2), is expected to show high inhibitory activity against the HIV protease [cf. Example 101 in Table 4 and Example 115 in Table 4].

Example 193

5Isoquinoline-O—CH$_2$—CO-Mta-(2S,3S)-AHPBA-Thz-NH-tBu

[Process 1] 5-Isoquinolyloxyacetic acid

To an ice-cooled solution of 29.0 g of 5-hydroxyisoquinoline in 300 ml of DMF, 11.0 g of sodium methylate was added portionwise. After stirring for 30 min, 17.9 ml of methyl chloroacetate was added dropwise, and the resultant mixture was stirred at room temperature overnight and concentrated under reduced pressure. To the residue, 300 ml of toluene and 300 ml of water were added, and the whole mixture was filtered. The aqueous layer was extracted with 50 ml of toluene, and the combined toluene solution was treated with 2 g of charcoal and evaporated to give methyl 5-isoquinolyloxyacetate. The ester was dissolved in 100 ml of methanol, reacted with 80 ml of 3 N sodium hydroxide aqueous solution for 30 min. The reaction mixture was concentrated under reduced pressure, diluted with 80 ml of water and 160 ml of acetone, and neutralized with 20 ml of concentrated hydrochloric acid. The precipitates formed were filtered, washed with 80 ml of 50% aqueous acetone, and dried to give 34.5 g (85% yield) of the title compound.

[Process 2] 5Isoguinoline-O—CH$_2$—CO-Mta-(2S.3S)AHPBA-Thz-NH-tBu

To a suspension of 2.29 g of the compound obtained by Example 162 (Process 1) in 13 ml of dichloromethane, 13 ml of 4 N-HCl in dioxane was added dropwise under ice-cooling and the resultant mixture was stirred at room temperature for 2 hr. The reaction mixture was neutralized with 95 ml of 5% sodium hydrogencarbonate aqueous solution and extracted with dichloromethane (50 ml+20 ml). The combined dichloromethane solution was dried over anhydrous magnesium sulfate and evaporated under reduced pressure. The residue was dissolved in 5 ml of DMF, and the resultant solution was added to a mixture of 1.09 g of the carboxylic acid obtained by Process 1 and 0.69 g of HOBt in 7 ml of DMF. To the whole mixture, a solution of 1.11 g of DCC in 3 ml of DMF was added under ice-cooling, and the resultant mixture was stirred at room temperature overnight. To the reaction mixture, 30 ml of ethyl acetate and 45 ml of 10% citric acid aqueous solution were added and the mixture was stirred at room temperature for 1 hr, and filtered. The filtrate was neutralized with 30 ml of 5% sodium hydrogencarbonate aqueous solution, and the aqueous layer was extracted with 15 ml of ethyl acetate. The combined ethyl acetate solution was washed with 3% potassium carbonate aqueous solution and 5% sodium chloride aqueous solution successively, dried over anhydrous magnesium sulfate, and evaporated under reduced pressure. The residue was subjected to a silca gel column chromatography (heptane:ethyl acetate=1:3, then ethanol:ethyl acetate=1:20). The subsequent recrystallization from ethanol gave 2.93 g of the title compound.

TLC: Rf (Ethyl acetate:Hexane=3:2)

Analytical HPLC: 14.9 min (For the condition, see: Example 35)

FAB-MS: 668 (M+1)

Melting Range: 173–176° C.

$^{13}$CNMR (DMSO-d6): 15.0, 28.4, 33.0, 33.2, 36.0, 49.3, 50.3, 51.2, 53.4, 62.3, 67.2, 71.5, 109.9, 114.7, 119.9, 125.9, 127.3, 127.7, 127.9, 129.0, 129.4, 139.1, 142.6, 151.8, 152.2, 167.0, 168.8, 169.4, 169.9

Example 194

5Isoquinoline-O—CH$_2$—CO-Val-(2S 3S)-AHPBA-Pro-NH-tBu

[Process 1] H-(2S,3S)-AHPBA-Pro-NH-tBu

Deprotection of 12.5 g of the compound obtained by Example 55 (Process 2) was performed similarly to that in Example 28 (Process 3). The subsequent aqueous work-up and recrystallization from toluene gave 5.80 g of the title compound.

[Process 2] Boc-Val-(2S,3S)-AHPBA-Pro-NH-tBu

To a solution of 1.00 g of the compound obtained by the process 1 in 15 ml of DMF, 0.63 g of Boc-Val-OH, 0.39 g of HOBt, and 0.61 g of EDC hydrochloride were added, and the resultant mixture was stirred overnight. The product was precipitated by addition of 5% citric acid aqueous solution, and the precipitates were washed with 3% potassium carbonate aqueous solution, water, and methanol successively to give 1.42 g of the title compound.

[Process 3] 5Isoquinoline-O—CH$_2$—CO-Val-(2S, 3S)-AHPBA-Pro-NH-tBu

Deprotection of 500 mg of the compound obtained by the process 2 was performed similarly to that in Example 28 (Process 3) and the obtained product was dissolved in 6 ml of DMF and neutralized with 127 µl of triethylamine. To this, 186 mg of 5-isoquinolyloxyacetic acid obtained by Example 193 (Process 1), 124 mg of HOBt, and 192 mg of EDC hydrochloride were added and the resultant solution was stirred overnight. The reaction mixture was concentrated under reduced pressure, and the residue was dissolved in dichloromethane, washed with 3% potassium carbonate aqueous solution and 5% sodium chloride aqueous solution successively, dried over magnesium sulfate, and concentrated under reduced pressure. The subsequent silica-gel column chromatography gave 490 mg of the title compound.

TLC: Rf 0.56 (Chloroform:Methanol=9:1)

FAB-MS: 632 (M+1)

Example 195

3Pyridine-O—CH$_2$—CO-Val-(2S,3S)-AHPBA-Thz-NHtBu

[Process 1] H-Val-(2S,3S)-AHPBA-Thz-NH-tBu

Deprotection of 2.0 g of the compound obtained by Example 179 (Process 1) was performed similarly to that in Example 28 (Process 3) and the crude title compound was obtained as its hydrochloride.

[Process 2] 3Pyridine-O—CH$_2$—CO-Val-(2S,3S)-AHPBA-Thz-NH-tBu

To a solution of 0.50 g of the hydrochloride obtained by process 1 in 4 ml of DMF, 0.14 ml of triethylamine, 0.17 g of 3-pyridyloxyacetic acid, 0.15 g of HOBt, and 0.21 g of EDC hydrochloride were added and the resultant solution was stirred overnight. The usual aqueous work-up gave 0.51 g of the crude title compound. The crude product was recrystallized from ethyl acetate.

TLC: Rf 0.34 (Chloroform:Methanol=9:1)

Analytical HPLC: 15.6 min (The condition was as follows)

Column: YMC AM-302 (4.6×150 mm)

Solvent A: 0.1% trifluoroacetic acid aqueous solution

Solvent B: acetonitrile

Gradient: 100% A to 100% B over 30 min

Flow Pate: 1.0 ml/min

FAB-MS: 601 (M+1)

Example 196

5Isoquinoline-O—CH$_2$—CO-Val-(2S,3S)-AHPBA-ThzNH-tBu

The title compound was prepared by the similar method to Example 194 (Process 2) using 5-isoquinolyloxyacetic acid instead of 3-pyridyloxyacetic acid.

Analytical HPLC: 15.4 min (For the condition, see: Example 35)

FAB-MS: 650 (M+1)

```
                         SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION: 1..9
          (D) OTHER INFORMATION: /note= "PEPTIDE SUBSTRATE"

(xi) SEQUENCE DESCRIPTION: SEQ ID NO:1:

Arg Ala Ser Gln Asn Tyr Pro Val Val
1               5

(2) INFORMATION FOR SEQ ID NO:2:

(i) SEQUENCE CHARACTERISTICS:
          (A) LENGTH: 5 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
```

(B) LOCATION: 1..5
            (D) OTHER INFORMATION: /note= "WHEREIN XAA IS DEFINED IN
                TABLE 8"

(xi) SEQUENCE DESCRIPTION: SEQ ID NO:2:

Asn Xaa Pro Ile Val
1               5

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "WHEREIN XAA IS DEFINED IN
            TABLE 8"

(xi) SEQUENCE DESCRIPTION: SEQ ID NO:3:

Val Val Xaa Phe Val Val
1               5

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "WHEREIN XAA IS DEFINED IN
            TABLE 8"

(xi) SEQUENCE DESCRIPTION: SEQ ID NO:4:

Ser Xaa Pro Ile Val
1               5

(2) INFORMATION FOR SEQ ID NO:5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "WHEREIN XAA IS DEFINED IN
            TABLE 8"

(xi) SEQUENCE DESCRIPTION: SEQ ID NO:5:

Val Val Xaa Xaa Val Val
1               5

(2) INFORMATION FOR SEQ ID NO:6:

(i) SEQUENCE CHARACTERISTICS:

```
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /note= "WHEREIN XAA IS DEFINED IN
                TABLE 8"

(xi) SEQUENCE DESCRIPTION: SEQ ID NO:6:

Asn Xaa Pro Ile
1

(2) INFORMATION FOR SEQ ID NO:7:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /note= "WHEREIN XAA IS DEFINED IN
                TABLE 8"

(xi) SEQUENCE DESCRIPTION: SEQ ID NO:7:

Asn Xaa Pro Xaa
1

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "WHEREIN XAA IS DEFINED IN
                TABLE 8"

(xi) SEQUENCE DESCRIPTION: SEQ ID NO:8:

Gln Xaa Pro Ile Val
1               5

(2) INFORMATION FOR SEQ ID NO:9:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..5
            (D) OTHER INFORMATION: /note= "WHEREIN XAA IS DEFINED IN
                TABLE 8"
```

-continued (xi) SEQUENCE DESCRIPTION: SEQ ID NO:9:

Xaa Xaa Pro Ile Val
1               5

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "WHEREIN XAA IS DEFINED IN
            TABLE 8"

(xi) SEQUENCE DESCRIPTION: SEQ ID NO:10:

Asn Xaa Pro Val Val
1               5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "WHEREIN XAA IS DEFINED IN
            TABLE 8"

(xi) SEQUENCE DESCRIPTION: SEQ ID NO:11:

Asn Xaa Pro Leu Val
1               5

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "WHEREIN XAA IS DEFINED IN
            TABLE 8"

(xi) SEQUENCE DESCRIPTION: SEQ ID NO:12:

Xaa Pro Ile Val
1

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear

```
    (ii) MOLECULE TYPE: peptide (ix) FEATURE:
         (A) NAME/KEY: Peptide
         (B) LOCATION: 1..7
         (D) OTHER INFORMATION: /note= "WHEREIN XAA IS DEFINED IN
             TABLE 8"

(xi) SEQUENCE DESCRIPTION: SEQ ID NO:13:

Ser Phe Asn Xaa Pro Ile Val
1               5

(2) INFORMATION FOR SEQ ID NO:14:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..4
         (D) OTHER INFORMATION: /note= "WHEREIN XAA IS DEFINED IN
             TABLE 8"

(xi) SEQUENCE DESCRIPTION: SEQ ID NO:14:

Val Xaa Phe Val
1

(2) INFORMATION FOR SEQ ID NO:15:

(i) SEQUENCE CHARACTERISTICS:
         (A) LENGTH: 5 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..5
         (D) OTHER INFORMATION: /note= "WHEREIN XAA IS DEFINED IN
             TABLE 8"

(xi) SEQUENCE DESCRIPTION: SEQ ID NO:15:

His Xaa Pro Ile Val
1               5

(2) INFORMATION FOR SEQ ID NO:16:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /note= "WHEREIN XAA IS DEFINED IN
             TABLE 8"

(xi) SEQUENCE DESCRIPTION: SEQ ID NO:16:

Xaa Asn Xaa Pro Ile Val
1               5
```

```
(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "WHEREIN XAA IS DEFINED IN
            TABLE 8"

(xi) SEQUENCE DESCRIPTION: SEQ ID NO:17:

Leu Xaa Pro Ile Val
1               5

(2) INFORMATION FOR SEQ ID NO:18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "WHEREIN XAA IS DEFINED IN
            TABLE 8"

(xi) SEQUENCE DESCRIPTION: SEQ ID NO:18:

Asn Xaa Pro Gln Ile
1               5

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "WHEREIN XAA IS DEFINED IN
            TABLE 8"

(xi) SEQUENCE DESCRIPTION: SEQ ID NO:19:

Asn Xaa Pro Val
1

(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
```

-continued

```
            (A) NAME/KEY: Peptide
            (B) LOCATION: 1..5
            (D) OTHER INFORMATION: /note= "WHEREIN XAA IS DEFINED IN
                TABLE 8"

(xi) SEQUENCE DESCRIPTION: SEQ ID NO:20:

Ser Asn Xaa Pro Ile
1

(2) INFORMATION FOR SEQ ID NO:21:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /note= "WHEREIN XAA IS DEFINED IN
                TABLE 8"

(xi) SEQUENCE DESCRIPTION: SEQ ID NO:21:

Xaa Xaa Xaa Xaa
1

(2) INFORMATION FOR SEQ ID NO:22:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..4
            (D) OTHER INFORMATION: /note= "WHEREIN XAA IS DEFINED IN
                TABLE 8"

(xi) SEQUENCE DESCRIPTION: SEQ ID NO:22:

Xaa Xaa Xaa Gly
```

What is claimed is:

1. A pharmaceutical composition for inhibiting human immunodeficiency virus (HIV) replication which comprises a pharmaceutically acceptable carrier, and an effective protease inhibiting amount of an active ingredient for inhibiting HIV replication, wherein said ingredient is a compound represented by the formula (3') or a salt thereof, (3')

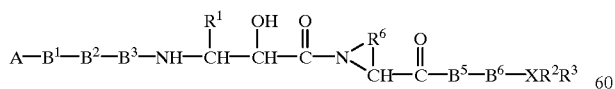

wherein:

A represents a hydrogen atom or a peptide N-terminal blocking group, wherein said blocking group is selected from the group consisting of aryloxyacetyl moieties, heteroaryloxyacetyl moieties, 3-phenylpropionyl, quinoline-2-carbonyl, tert-butoxycarbonyl and benzyloxycarbonyl, $B^1$, $B^2$, $B^3$, $B^5$ and $B^6$ independently represents a single bond or an amino acid residue and optionally the amino group of said amino acid is substituted with a hydrocarbon group having 12 or fewer carbon atoms, X represents a nitrogen atom, $R^1$ represents a benzyl group or a cyclohexylmethyl group, $R^2$ and $R^3$ each represent a hydrogen atom or a hydrocarbon group having 12 or fewer carbon atoms which may form a cyclic ring together with the nitrogen atom to which they are attached, wherein said hydrocarbon group may optionally be substituted with hydroxyl groups, and $R^6$ represents a bivalent hydrocarbon group which, together with the nitrogen atom and methine carbon to which it is attached, forms a ring system selected from pyrrolidine, thiazolidine, indoline, octahydroindole, piperidine, 1,2,3,4-tetrahydroisoquinoline or decahydroisoquinoline, wherein the ring system is optionally substituted with a hydroxyl group, a methoxy group, an ethoxy group, an allyloxy group, a benzyloxy group, a phenyl group, or methyl groups.

2. The pharmaceutical composition of claim 1 wherein $B^1$ and $B^2$ in formula (3') are both single bonds.

3. The pharmaceutical composition of claim 1 or 2, wherein $B^3$ in formula (3') represents the residue of valine, leucine, isoleucine, asparagine, glutamine, aspartic acid, glutamic acid, cyanoalanine, cyanomethylalanine, O-methylaspartic acid, O-methylglutamic acid, serine, O-methylserine, β-methylthioalanine, methionine, β-methanesulfonylalanine, β-(methanesulfonylmethyl)alanine, β-sulfonylalanine, β-sulfonylmethylalanine, β-sulfamoylalanine or β-sulfamoylmethylalanine.

4. The pharmaceutical composition of claim 1, 2, or 3, wherein an amino acid residue represented by following formula (11) in formula (3'), represents proline, 3,3-dimethylpyrrolidine-2-carboxylic acid, 1,3-thiazolidine-4-carboxylic acid or 5,5-dimethyl-1,3-thiazolidine-4-carboxylic acid residue

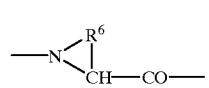

(11)

5. The pharmaceutical composition of claim 1, 2, or 3, wherein —$XR^2R^3$ in formula (3') represents an N-tertbutylamino group.

6. The pharmaceutical composition of claim 1, wherein $B^1$, $B^2$, $B^5$ and $B^6$ in formula (3') are all single bonds.

7. The pharmaceutical composition of claim 1, wherein said active ingredient is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-1,3-thiazolidine-4-carboxamide.

8. The pharmaceutical composition of claim 1, wherein said active ingredient is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-5,5-dimethyl-1,3-thiazolidine-4-carboxamide.

9. The pharmaceutical composition of claim 1, wherein said active ingredient is (R)-N-tert-butyl-3-((2S,3S)-2-hydroxy-3-N-((S)-3-methyl-2-N-(3-pyridyloxyacetyl)aminobutanoyl)amino-4-phenylbutanoyl)-1,3-thiazolidine-4-carboxamide.

10. The pharmaceutical composition of claim 1, wherein said active ingredient is (R)-N-tert-butyl-3-((2S,3S)-2-hydroxy-3-N-((R)-2-N-(5-isoquinolyloxyacetyl)amino-3-methylbutanoyl)amino-4-phenylbutanoyl)pyrrolidine-2-carboxamide.

11. A pharmaceutical composition for inhibiting human immunodeficiency virus (HIV) replication which comprises a pharmaceutically acceptable carrier, and an effective protease inhibiting amount of an active ingredient for inhibiting HIV replication, wherein said ingredient is a compound represented by formula (a) or a salt thereof,

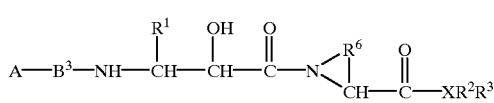

(a)

wherein:
A represents a hydrogen atom or a peptide N-terminal blocking group, wherein said blocking group is selected from the group consisting of aryloxyacetyl moieties, heteroaryloxyacetyl moieties, 3-phenylpropionyl, quinoline-2-carbonyl, tert-butoxycarbonyl and benzyloxycarbonyl, $B^3$ represents an amino acid residue and optionally the amino group of said amino acid is substituted with a hydrocarbon group having 12 or fewer carbon atoms, X represents a nitrogen atom, $R^1$ represents a benzyl group or a cyclohexylmethyl group, $R^2$ and $R^3$ each represent a hydrogen atom or a hydrocarbon group having 12 or fewer carbon atoms which may form a cyclic ring together with the nitrogen atom to which they are attached, wherein said hydrocarbon group may optionally be substituted with hydroxyl groups, and $R^6$ represents a bivalent hydrocarbon group which, together with the nitrogen atom and methine carbon to which it is attached, forms a ring system selected from pyrrolidine, thiazolidine, indoline, octahydroindole, piperidine, 1,2,3,4-tetrahydroisoquinoline or decahydroisoquinoline, wherein the ring, system is optionally substituted with a hydroxyl group, a methoxy group, an ethoxy group, an allyloxy group, a benzyloxy group, a phenyl group, or methyl groups.

12. The pharmaceutical composition of claim 1 or 11, wherein said active ingredient comprises 0.1 to 99.0% of said pharmaceutical composition.

13. The pharmaceutical composition of claim 1 or 11, wherein said pharmaceutically acceptable carrier is selected from the group consisting of oils, propyleneglycol, physiological saline, polyethylene glycol, ethanol, sesame oil, cremophor and isopropyl myristate.

14. A pharmaceutical composition comprising:
a retrovirus inhibitory effective amount of the compound, or salt thereof, of the formula:

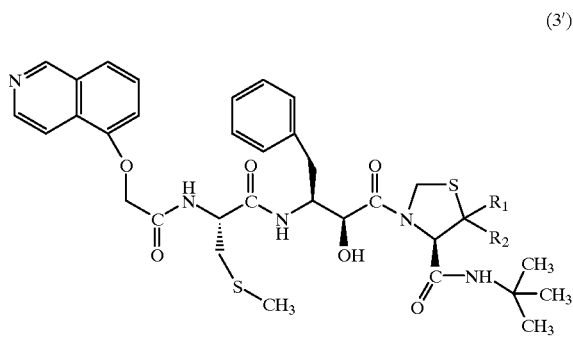

(3')

wherein $R_1$ and $R_2$ are the same and are $CH_3$ or H; and, a pharmaceutically acceptable carrier.

15. The composition of claim 14 wherein $R_1$ and $R_2$ are H.

16. The composition of claim 14 wherein $R_1$ and $R_2$ are $CH_3$.

17. The composition of claim 14, 15 or 16 wherein said retrovirus is HIV.

18. A method for inhibiting human immunodeficiency virus (HIV) replication which comprises contacting cells which are infected with HIV with an effective viral inhibiting amount of a compound represented by formula (3') or a salt thereof, (3')

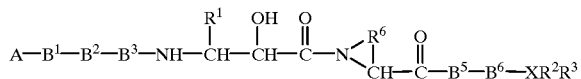

wherein:

A represents a hydrogen atom or a peptide N-terminal blocking group, wherein said blocking group is selected from the group consisting of aryloxyacetyl moieties, heteroaryloxyacetyl moieties, 3-phenylpropionyl, quinoline-2-carbonyl, tert-butoxycarbonyl and benzyloxycarbonyl, $B^1$, $B^2$, $B^3$, $B^5$ and $B^6$ independently represents a single bond or an amino acid residue and optionally the amino group of said amino acid is substituted with a hydrocarbon group having 12 or fewer carbon atoms, X represents a nitrogen atom, $R^1$ represents a benzyl group or a cyclohexylmethyl group, $R^2$ and $R^3$ each represent a hydrogen atom or a hydrocarbon group having 12 or fewer carbon atoms which may form a cyclic ring together with the nitrogen atom to which they are attached, wherein said hydrocarbon group may optionally be substituted with hydroxyl groups, and $R^6$ represents a bivalent hydrocarbon group which, together with the nitrogen atom and methine carbon to which it is attached, forms a ring system selected from pyrrolidine, thiazolidine, indoline, octahydroindole, piperidine, 1,2,3,4-tetrahydroisoquinoline or decahydroisoquinoline, wherein the ring system is optionally substituted with a hydroxyl group, a methoxy group, an ethoxy group, an allyloxy group, a benzyloxy group, a phenyl group, or methyl groups.

19. The method of claim 18, wherein said compound is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-1,3-thiazolidine-4-carboxamide.

20. The method of claim 18, wherein said compound is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-5,5-dimethyl-1,3-thiazolidine-4-carboxamide.

21. the method of claim 18, wherein said compound is (R)-N-tert-butyl-3-((2S,3S)-2-hydroxy-3-N-((S)-3-methyl-2-N-(3-pyridyloxyacetyl)aminobutanoyl)amino-4-phenylbutanoyl)-1,3-thiazolidine-4-carboxamide.

22. The method of claim 18, wherein said compound is (R)-N-tert-butyl-3-((2S,3S)-2-hydroxy-3-N-((R)-2-N-(5-isoquninolyloxyacetyl)amino-3-methylbutanoyl)amino-4-phenylbutanoyl)-pyrrolidine-2-carboxamide.

23. The method of claim 18 wherein HIV is inhibited in vivo.

24. A method of treating a patient suffering from acquired immune deficiency syndrome (AIDS) which comprises administering to said patient a therapeutically effective amount of a compound for mitigating human immunodeficiency virus (HIV) replication, said compound being represented by formula (3') or a salt thereof, (3')

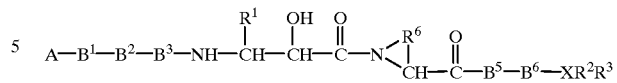

wherein:

A represents a hydrogen atom or a peptide N-terminal blocking group, wherein said blocking group is selected from the group consisting of aryloxyacetyl moieties, heteroaryloxyacetyl moieties, 3-phenylpropionyl, quinoline-2-carbonyl, tert-butoxycarbonyl and benzyloxycarbonyl, $B^1$, $B^2$, $B^3$, $B^5$ and $B^6$ independently represents a single bond or an amino acid residue and optionally the amino group of said amino acid is substituted with a hydrocarbon group having 12 or fewer carbon atoms, X represents a nitrogen atom, $R^1$ represents a benzyl group or a cyclohexylmethyl group, $R^2$ and $R^3$ each represent a hydrogen atom or a hydrocarbon group having 12 or fewer carbon atoms which may form a cyclic ring together with the nitrogen atom to which they are attached, wherein said hydrocarbon group may optionally be substituted with hydroxyl groups, and $R^6$ represents a bivalent hydrocarbon group which, together with the nitrogen atom and methine carbon to which it is attached, forms a ring system selected from pyrrolidine, thiazolidine, indoline, octahydroindole, piperidine, 1,2,3,4-tetrahydroisoquinoline or decahydroisoquinoline, wherein the ring system is optionally substituted with a hydroxyl group, a methoxy group, an ethoxy group, an allyloxy group, a benzyloxy group, a phenyl group, or methyl groups.

25. The method of claim 24, wherein said compound is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-1,3-thiazolidine-4-carboxamide.

26. The method of claim 24, wherein said compound is (R)-N-tert-butyl-3-((2S,3S)-2-hydroxy-3-N-((R)-2-N-(5-isoquinolyloxyacetyl)amino-3-methylthiopropanoyl)amino-4-phenylbutanoyl)-5,5-dimethyl-1,3-thiazolidine-4-carboxamide.

27. The method of claim 24, wherein said compound is (R)-N-tert-butyl-3-((2S,3S)-2-hydroxy-3-N-((S)-3-methyl-2-N-(3-pyridyloxyacetyl)aminobutanoyl)amino-4-phenylbutanoyl)-1,3-thiazolidine-4-carboxamide.

28. The method of claim 24, wherein said compound is (R)-N-tert-butyl-3-((2S,3S)-2-hydroxy-3-N-((R)-2-N-(5-isoquinolyloxyacetyl)amino-3-methylbutanoyl)amino-4-phenylbutanoyl)pyrrolidine-2-carboxamide.

29. The method of claim 24, wherein administration of said compound is intranasal, oral, parenteral, rectal or vaginal.

30. The method of claim 24, wherein said compound is administered in a dose of between 0.02 and 5 g per day.

31. A method for inhibiting retroviral replication comprising contacting cells that are infected with a retrovirus with an inhibitory effective amount of the compound or salt thereof, of the formula:

(3')

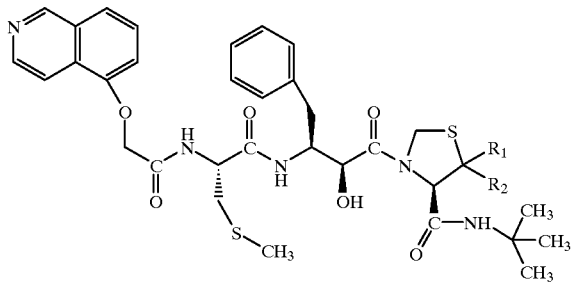

wherein $R_1$, $R_2$ are the same and are $CH_3$ or H.

32. The method of claim 31 wherein $R_1$ and $R_2$ are H.

33. The method of claim 32 wherein said retrovirus is HIV.

34. The method of claim 31 wherein $R_1$ and $R_2$ are $CH_3$.

35. The method of claim 34 wherein said retrovirus is HIV.

36. A method of treating HIV infection comprising administering to a human infected with the human immunodeficiency virus a therapeutically effective amount of the compound, or salt thereof, of the formula:

(3')

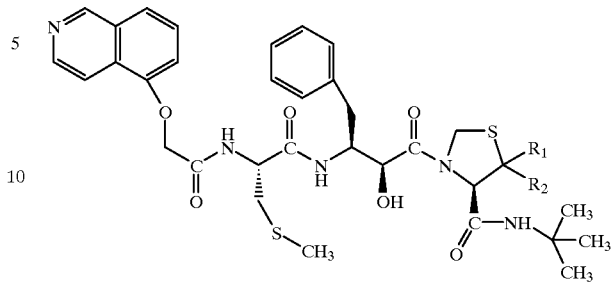

wherein $R_1$ $R_2$ are the same and are $CH_3$ or H.

37. The method of claim 37 wherein $R_1$ and $R_2$ are H.

38. The method of claim 37 wherein the mode of administration is intranasal, oral, parenteral, rectal or vaginal.

39. The method of claim 38 wherein said compound is administered such that plasma of said human attains a concentration of said compound between about 0.01 μM and about 100 μM.

40. The method of claim 36 wherein $R_1$ and $R_2$ are $CH_3$.

41. The method of claim 40 wherein the mode of administration is intranasal, oral, parenteral, rectal or vaginal.

42. The method of claim 41 wherein said compound is administered such that plasma of said human attains a concentration of said compound between about 0.01 μM and about 100 μM.

* * * * *

UNITED STATES PATENT AND TRADEMARK OFFICE
CERTIFICATE OF CORRECTION

PATENT NO. : 6,313,094 B1
DATED : November 6, 2001
INVENTOR(S) : Mimoto et al.

It is certified that error appears in the above-identified patent and that said Letters Patent is hereby corrected as shown below:

<u>Title page,</u>
Under Item [*], Notice: please delete "This patent is subject to a terminal disclaimer."
Item [30], under Foreign Application Priority Data, please delete "3-167174" and substitute -- 3-169174 -- therefor.

<u>Column 119,</u>
Line 50, please delete "phenylbutanoyl)" and substitute -- phenylbutanoyl)- -- therefor.

<u>Column 120,</u>
Line 23, please delete the comma "," after "ring";

<u>Column 122,</u>
Line 66, please insert a comma -- , -- after "compound".

<u>Column 124,</u>
Line 17, the claim reference numeral "37" should read -- 36 --.

Signed and Sealed this

Thirteenth Day of August, 2002

*Attest:*

*Attesting Officer*

JAMES E. ROGAN
*Director of the United States Patent and Trademark Office*